US007914776B2

(12) United States Patent
Kumar

(10) Patent No.: US 7,914,776 B2
(45) Date of Patent: Mar. 29, 2011

(54) SOLID DISPERSIONS OF OPIOID ANTAGONISTS

(75) Inventor: Virendra Kumar, Berwyn, PA (US)

(73) Assignee: Adolor Corporation, Exton, PA (US)

( * ) Notice: Subject to any disclaimer, the term of this patent is extended or adjusted under 35 U.S.C. 154(b) by 767 days.

(21) Appl. No.: 11/543,619

(22) Filed: Oct. 5, 2006

(65) Prior Publication Data

US 2007/0082053 A1    Apr. 12, 2007

Related U.S. Application Data

(60) Provisional application No. 60/724,819, filed on Oct. 7, 2005.

(51) Int. Cl.
*A61K 31/785* (2006.01)
*C08F 20/00* (2006.01)
(52) U.S. Cl. ...................... 424/78.27; 424/423; 525/438
(58) Field of Classification Search ................ 424/78.27
See application file for complete search history.

(56) References Cited

U.S. PATENT DOCUMENTS

| | | | | |
|---|---|---|---|---|
| 4,115,400 | A | 9/1978 | Zimmerman | 260/326.5 B |
| 4,581,456 | A | 4/1986 | Barnett | 546/185 |
| 4,891,379 | A | 1/1990 | Zimmerman et al. | 514/315 |
| 5,136,040 | A | 8/1992 | Werner | 546/218 |
| 5,159,081 | A | 10/1992 | Cantrell et al. | 546/226 |
| 5,250,542 | A | 10/1993 | Cantrell et al. | 514/445 |
| 5,270,328 | A | 12/1993 | Cantrell et al. | 514/331 |
| 5,434,171 | A | 7/1995 | Frank et al. | 514/331 |
| 6,451,806 | B2 | 9/2002 | Farrar | 514/282 |
| 6,469,030 | B2 | 10/2002 | Farrar et al. | 514/331 |
| 7,276,252 | B2 * | 10/2007 | Payumo et al. | 424/472 |
| 2001/0036951 | A1 | 11/2001 | Farrar et al. | |
| 2001/0047005 | A1 * | 11/2001 | Farrar | 514/282 |
| 2004/0254208 | A1 | 12/2004 | Weber et al. | 514/282 |
| 2005/0124657 | A1 * | 6/2005 | Christ et al. | 514/317 |
| 2006/0258696 | A1 * | 11/2006 | Moss et al. | 514/283 |
| 2008/0194611 | A1 * | 8/2008 | Alverdy et al. | 514/282 |

OTHER PUBLICATIONS

Leuner et al. Improving Drug Solubility for Oral Delivery Using Solid Dispersions. 1999. (submitted in IDS).*
Leuner et al. "Improving Drug Solubility for Oral Delivery Using Solid Dispersions" European Journal of Phamaceutics and Biopharmaceutics 50 (2000) pp. 47-60.
Petit et al. "The Amorphous State" Polymorphism: in the Pharmaceutical Industry Edited by Rolf Hilfker Wiley-VCH Verlag GmbH & Co. KGaA (2006) pp. 259-285.
Foss et al. Alvimopan (ENTEREG) A Novel Opioid Antagonist, Achieves Active Systemic Concentrations, Am. Soc. For Clin. Pharma. And Therapeutics (2005) p. 74.
Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.
Bilsky, E.J., et al., "Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice," *J. Pharmacol. & Exp. Ther.*, 1996, 277(1), 484-490.
*Dorland's Illustrated Medical Dictionary*, 27$^{th}$ Ed., W.B. Saunders Co., 1988, p. 816.
*Dorland's Illustrated Medical Dictionary*, 27$^{th}$ Ed., W.B. Saunders Co., 1988, p. 375.
Dourish, C.T., et al., "Enhancement of morphine analgesia and prevention of morphine tolerance in the rat by the cholecystokinin antagonist L-364, 718," *Eur. J. Pharmacol.*, 1988, 147, 469-472.
Greene, T.W., et al., *Protective Groups in Organic Synthesis*, 2d Ed., Wiley & Sons, 1991, Index, 3 pages.
Livingston, E.H., et al., "Postoperative Ileus," *Digestive Diseases and Sciences*, 1990, 35(1), 121-132.
Mao, M.J., et al., "Oral administration of dextromethorphan prevents the development of morphine tolerance and dependence in rats," *Pain*, 1996, 67, 361-368.
Nichols, M.L., et al., "Enhancement of the antiallodynic and antinociceptive efficancy of spinal morphine by antisera to dynorphin A (1-13) or MK-801 in a nerve-ligation model of peripheral neuropathy," *Pain*, 1997, 69, 317-322.
Orchin, M., et al., *The Vocabulary of Organic Chemistry*, John Wiley & Sons, pp. v, 126-127, 1980.
*Physicians' Desk Reference*, Section 3, Product Category Index, 1999, 16 pages.
Resnick, J., et al., "Delayed gastric emptying and postoperative Ileus after nongastric abdominal surgery: Part II," *Am. J. of Gastroenterology*, 1997, 92(6), 934-940.
Resnick, J., et al., "Delayed gastric emptying and postoperative Ileus after nongastric abdominal surgery: Part I," *Am. J. of Gastroenterology*, 1997, 751-762.
Werner. J.A., et al., "Synthesis of *trans*-3,4-dimethyl-4-(3-hydroxypheny)piperidine opioid antagonists: application of the *Cis*-thermal elimination of carbonates to alkaloid synthesis," *J. of Organic Chemistry*, 1996, 61, 587-597.

* cited by examiner

*Primary Examiner* — Shanon A Foley
*Assistant Examiner* — Sarah Al-Awadi
(74) *Attorney, Agent, or Firm* — Feldman Gale, P.A.; Walter C. Frank

(57) ABSTRACT

Solid dispersions of stable, amorphous opioid antagonists, particularly [[2(S)-[[4(R)-(3-hydroxyphenyl)-3(R),4-dimethyl-piperidinyl]methyl]-1-oxo-3-phenylpropyl]amino] acetic acid, with improved water solubility and bioavailability are disclosed. Also disclosed are methods of preventing or treating a side effect associated with an opioid. In addition, methods of treating or preventing pain, ileus, and opioid bowel dysfunction are disclosed.

22 Claims, No Drawings

SOLID DISPERSIONS OF OPIOID ANTAGONISTS

CROSS REFERENCE TO RELATED APPLICATIONS

This application claims benefit of U.S. Application Ser. No. 60/724,819 filed Oct. 7, 2005, the entire disclosure of which is incorporated herein by reference.

FIELD OF THE INVENTION

The present invention relates to solid dispersions of opioid antagonists. More particularly, the present invention relates to solid dispersions of stable, amorphous opioid antagonists, particularly alvimopan, with improved water solubility and bioavailability, and methods of their use.

BACKGROUND OF THE INVENTION

[[2(S)-[[4(R)-(3-hydroxyphenyl)-3(R),4-dimethyl-piperidinyl]methyl]-1-oxo-3-phenylpropyl]amino]acetic acid dihydrate (USAN name alvimopan) is a peripherally-acting μ opioid antagonist that is used in the treatment of post operative ileus and opioid bowel dysfunction, as well as other indications. Alvimopan is a 3,4-disubstituted-4-aryl piperidine that is a zwitterion. It has an extremely low solubility in water and many common pharmaceutically-acceptable solvents. As a result, it has poor oral bioavailability.

[[2(S)-[[4(R)-(3-hydroxyphenyl)-3(R),4-dimethyl-piperidinyl]methyl]-1-oxo-3-phenylpropyl]amino]acetic acid may exist in different crystalline forms, including hydrate forms, solvate forms and anhydrous form, and as an amorphous material. Above a relative humidity of about 15%, it exists in its crystalline dihydrate form. Below a relative humidity of about 15%, it exists in its anhydrous form. Amorphous [[2(S)-[[4(R)-(3-hydroxyphenyl)-3(R),4-dimethyl-piperidinyl]methyl]-1-oxo-3-phenylpropyl]amino]acetic acid is hygroscopic and converts to its crystalline dihydrate form when it is stressed, for example, at 54% relative humidity for 12 days or 75% relative humidity in the temperature range of about 40° C. to about 80° C. for three days. Under ambient conditions, amorphous [[2(S)-[[4(R)-(3-hydroxyphenyl)-3(R),4-dimethyl-piperidinyl]methyl]-1-oxo-3-phenylpropyl]amino]acetic acid completely converts to its crystalline dihydrate form after 66 days.

The crystalline dihydrate form of [[2(S)-[[4(R)-(3-hydroxyphenyl)-3(R),4-dimethyl-piperidinyl]methyl]-1-oxo-3-phenylpropyl]amino]acetic acid (alvimopan) has a lower solubility in water than amorphous [[2(S)-[[4(R)-(3-hydroxyphenyl)-3(R),4-dimethyl-piperidinyl]methyl]-1-oxo-3-phenylpropyl]amino]acetic acid and hence lower bioavailability than the amorphous form. Accordingly, it would be desirable to develop a stable, amorphous form of [[2(S)-[[4(R)-(3-hydroxyphenyl)-3(R),4-dimethyl-piperidinyl]methyl]-1-oxo-3-phenylpropyl]amino]acetic acid and related 3,4-disubstituted 4-aryl piperidine derivatives. The present invention is directed to these and other important objectives.

SUMMARY OF THE INVENTION

In one embodiment, the present invention is directed to solid dispersions, comprising:
at least one pharmaceutically-acceptable excipient selected from the group consisting of hydroxypropyl methylcellulose (HPMC), polyvinylpyrrolidone homopolymer (PVP), polyvinylpyrrolidone copolymer, and mixtures thereof; and
at least one compound of formula I:

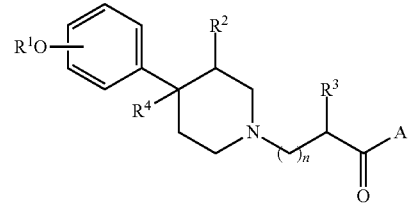

I wherein said compound is in a solid amorphous form;
wherein said amorphous form is stable; and
wherein:

$R^1$ is hydrogen or alkyl;

$R^2$ is hydrogen, alkyl, or alkenyl;

$R^3$ is hydrogen, alkyl, alkenyl, aryl, cycloalkyl, cycloalkenyl, cycloalkyl-substituted alkyl, cycloalkenyl-substituted alkyl, or aralkyl;

$R^4$ is hydrogen, alkyl, or alkenyl;

A is $OR^5$ or $NR^6R^7$;

$R^5$ is hydrogen, alkyl, alkenyl, cycloalkyl, cycloalkenyl, cycloalkyl-substituted alkyl, cycloalkenyl-substituted alkyl, or aralkyl;

$R^6$ is hydrogen or alkyl;

$R^7$ is hydrogen, alkyl, alkenyl, cycloalkyl, aryl, cycloalkyl-substituted alkyl, cycloalkenyl, cycloalkenyl-substituted alkyl, aralkyl, aralkyl, or alkylene substituted B or, together with the nitrogen atom to which they are attached, $R^6$ and $R^7$ form a heterocyclic ring;

B is

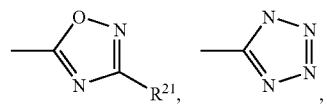

$C(=O)W$ or $NR^8R^9$;

$R^8$ is hydrogen or alkyl;

$R^9$ is hydrogen, alkyl, alkenyl, cycloalkyl-substituted alkyl, cycloalkyl, cycloalkenyl, cycloalkenyl-substituted alkyl, aryl or aralkyl or, together with the nitrogen atom to which they are attached, $R^8$ and $R^9$ form a heterocyclic ring;

W is $OR^{10}$, $NR^{11}R^{12}$, or OE;

$R^{10}$ is hydrogen, alkyl, alkenyl, cycloalkyl, cycloalkenyl, cycloalkyl-substituted alkyl, cycloalkenyl-substituted alkyl, or aralkyl;

$R^{11}$ is hydrogen or alkyl;

$R^{12}$ is hydrogen, alkyl, alkenyl, aryl, cycloalkyl, cycloalkenyl, cycloalkyl-substituted alkyl, cycloalkenyl-substituted alkyl, aralkyl or alkylene substituted $C(=O)Y$ or, together with the nitrogen atom to which they are attached, $R^{11}$ and $R^{12}$ form a heterocyclic ring;

E is

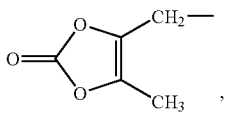

alkylene substituted (C=O)D, or —R$^{13}$OC(=O)R$^{14}$;

R$^{13}$ is alkyl-substituted alkylene;

R$^{14}$ is alkyl;

D is OR$^{15}$ or NR$^{16}$R$^{17}$;

R$^{15}$ is hydrogen, alkyl, alkenyl, cycloalkyl, cycloalkenyl, cycloalkyl-substituted alkyl, cycloalkenyl-substituted alkyl, or aralkyl;

R$^{16}$ is hydrogen, alkyl, alkenyl, aryl, aralkyl, cycloalkyl, cycloalkenyl, cycloalkyl-substituted alkyl, or cycloalkenyl-substituted alkyl;

R$^{17}$ is hydrogen or alkyl or, together with the nitrogen atom to which they are attached, R$^{16}$ and R$^{17}$ form a heterocyclic ring;

Y is OR$^{18}$ or NR$^{19}$R$^{20}$;

R$^{18}$ is hydrogen, alkyl, alkenyl, cycloalkyl, cycloalkenyl, cycloalkyl-substituted alkyl, cycloalkenyl-substituted alkyl, or aralkyl;

R$^{19}$ is hydrogen or alkyl;

R$^{20}$ is hydrogen, alkyl, alkenyl, aryl, cycloalkyl, cycloalkenyl, cycloalkyl-substituted alkyl, cycloalkenyl-substituted alkyl, or aralkyl or, together with the nitrogen atom to which they are attached, R$^{19}$ and R$^{20}$ form a heterocyclic ring;

R$^{21}$ is hydrogen or alkyl; and n is 0 to 4.

In certain preferred embodiments, the solid dispersions further comprise at least one opioid.

In yet other embodiments, the invention is directed to methods of preventing or treating a side effect associated with an opioid in a patient, including ileus, opioid bowel dysfunction, constipation, nausea, vomiting, or a combination thereof, comprising the step of:

administering to said patient an effective amount of the above-described solid dispersion.

In another embodiment, the invention is directed to methods of treating or preventing pain in a patient, comprising the step of:

administering to said patient in need thereof an effective amount of the above-described solid dispersion.

In other embodiments, the invention is directed to methods of treating or preventing ileus in a patient, comprising the step of:

administering to said patient in need thereof an effective amount of the above-described solid dispersion.

In yet other embodiments, the invention is directed to methods of treating or preventing opioid bowel dysfunction in a patient, comprising the step of:

administering to said patient in need thereof an effective amount of the above-described solid dispersion.

These and other aspects of the invention will become more apparent from the following detailed description.

DETAILED DESCRIPTION OF THE INVENTION

As employed above and throughout the disclosure, the following terms, unless otherwise indicated, shall be understood to have the following meanings.

As used herein, "solid dispersion" refers to at least a two-phase solid system of which one phase consists finely divided solid particles distributed throughout a bulk solid substance, the particles being the disperse or internal phase and the bulk substance the continuous or external phase.

As used herein, "amorphous" means non-crystalline; having no molecular lattice structure. As used herein, a solid dispersion of an amorphous compound of formula I may contain some minor amount of crystalline forms, for example, less than about 25% by weight, based on the total weight of the compound of formula I, of the crystalline form of the compound of formula I.

As used herein with respect to "amorphous form," "stable" refers to an amorphous material does not convert to a crystalline form for at least a minimum period of time under specified relative humidity and temperature conditions. With respect to the solid dispersions of the invention, minimally the compounds of formula I (and preferably the entire solid dispersion containing the compounds of formula I) maintain the amorphous form for greater than:

about 12 days at a relative humidity of about 54% and a temperature of about 10° C. to about 30° C.;

about 3 days at a relative humidity of about 75% and a temperature of about 40° C. to about 80° C.; or about 66 days under a relativity humidity of less than about 30% and a temperature of about 10° C. to about 30° C.

As used herein, "bioavailability" refers to the rate and extent to which a drug or other substance becomes available to the target tissue after administration. In the context of this invention, bioavailability refers to the degree to which the opioid antagonist becomes available to the opioid receptors in the central nervous system or peripheral thereto.

As used herein, "deliquesce" refers to the process by which a salt melts or becomes liquid by absorbing moisture from its surroundings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. "Branched" refers to an alkyl group in which a lower alkyl group, such as methyl, ethyl, or propyl, is attached to a linear alkyl chain. In certain preferred embodiments, the alkyl group is a $C_1$-$C_5$ alkyl group, i.e., a branched or linear alkyl group having from 1 to about 5 carbons. In other preferred embodiments, the alkyl group is a $C_1$-$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl, and decyl. "Lower alkyl" refers to an alkyl group having 1 to about 6 carbon atoms. Preferred alkyl groups include the lower alkyl groups of 1 to about 3 carbons. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkylene" refers to a bivalent alkyl radical having the general formula —$(CH_2)_n$—, where n is 1 to 10, and all combinations and subcombinations of ranges therein. The alkylene group may be straight, branched or cyclic. Non-limiting examples include methylene, methylene (—$CH_2$—), ethylene (—$CH_2CH_2$—), propylene (—$(CH_2)_3$—), trimethylene, pentamethylene, and hexamethylene. There may be optionally inserted along the alkylene group one or more oxygen, sulfur or optionally substituted nitrogen atoms, wherein the nitrogen substituent is alkyl as described previously. Alkylene groups can be optionally substituted. The term "lower alkylene" herein refers to those alkylene groups having from about 1 to about 6 carbon atoms. Preferred alkylene groups have from about 1 to about 4 carbons.

As used herein, "alkenyl" refers to a monovalent alkyl radical containing at least one carbon-carbon double bond and having from 2 to about 10 carbon atoms in the chain, and all combinations and subcombinations of ranges therein. Alkenyl groups can be optionally substituted. In certain preferred embodiments, the alkenyl group is a $C_2$-$C_{10}$ alkyl group, i.e., a branched or linear alkenyl group having from 2 to about 10 carbons. In other preferred embodiments, the alkenyl group is a $C_2$-$C_6$ alkenyl group, i.e., a branched or linear alkenyl group having from 2 to about 6 carbons. In still other preferred embodiments, the alkenyl group is a $C_3$-$C_{10}$ alkenyl group, i.e., a branched or linear alkenyl group having from about 3 to about 10 carbons. In yet other preferred embodiments, the alkenyl group is a $C_2$-$C_5$ alkenyl group, i.e., a branched or linear alkenyl group having from 2 to about 5 carbons. Exemplary alkenyl groups include, for example, vinyl, propenyl, butenyl, pentenyl hexenyl, heptenyl, octenyl, nonenyl and decenyl groups.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted in either the aryl or alkyl portions. Non-limiting examples include, for example, phenylmethyl (benzyl), diphenylmethyl, triphenylmethyl, phenylethyl, diphenylethyl and 3-(4-methylphenyl)propyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred, with from about 3 to about 8 carbon atoms being more preferred, with from about 3 to about 6 carbon atoms being even more preferred. Multi-ring structures may be bridged or fused ring structures. The cycloalkyl group may be optionally substituted with, for example, alkyl, preferably $C_1$-$C_3$ alkyl, alkoxy, preferably $C_1$-$C_3$ alkoxy, or halo. Non-limiting examples include, for example, cyclopropyl, cyclobutyl, cyclopentyl, cyclohexyl, cycloheptyl cyclooctyl, and adamantyl.

As used herein, "cycloalkyl-substituted alkyl" refers to a linear alkyl group, preferably a lower alkyl group, substituted at a terminal carbon with a cycloalkyl group, preferably a $C_3$-$C_8$ cycloalkyl group. Non-limiting examples include, for example, cyclopentylmethyl, cyclohexylethyl, cyclopentylethyl, cyclopentylpropyl, cyclopropylmethyl, and the like.

As used herein, "cycloalkenyl" refers to an olefinically unsaturated cycloalkyl group having from about 4 to about 10 carbons, and all combinations and subcombinations of ranges therein. In preferred embodiments, the cycloalkenyl group is a $C_5$-$C_8$ cycloalkenyl group, i.e., a cycloalkenyl group having from about 5 to about 8 carbons.

As used herein, "alkylcycloalkyl" refers to an optionally substituted ring system comprising a cycloalkyl group having one or more alkyl substituents. Non-limiting examples include, for example, alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Non-limiting examples include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydrocyclopenta[c]pyranyl, 1,2,3,4,-tetrahydroquinolyl, octahydro-[2]pyrindinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro [4.7] dodecane.

As used herein, the term "alkoxy" refers to an optionally substituted alkyl-O—group wherein alkyl is as previously defined. Non-limiting examples include, for example, include methoxy, ethoxy, n-propoxy, i-propoxy, n-butoxy, and heptoxy.

As used herein, the term "aryloxy" refers to an optionally substituted aryl-O— group wherein aryl is as previously defined. Non-limiting examples include, for example, phenoxy and naphthoxy.

As used herein, the term "aralkoxy" refers to an optionally substituted aralkyl-O— group wherein aralkyl is as previously defined. Non-limiting examples include, for example, benzyloxy, 1-phenylethoxy, 2-phenylethoxy, and 3-naphthylheptoxy.

As used herein, the term "aryloxyaryl" refers to an aryl group with an aryloxy substituent wherein aryloxy and aryl are as previously defined. Aryloxyaryl groups can be optionally substituted. Non-limiting examples include, for example, phenoxyphenyl, and naphthoxyphenyl.

As used herein, the term "heteroarylaryl" refers to an aryl group with a heteroaryl substituent wherein heteroaryl and aryl are as previously defined. Heteroarylaryl groups can be optionally substituted. Non-limiting examples include, for example, 3-pyridylphenyl, 2-quinolylnaphthalenyl, and 2-pyrrolylphenyl.

As used herein, the term "alkoxyaryl" refers to an aryl group bearing an alkoxy substituent wherein alkoxy and aryl are as previously defined. Alkoxyaryl groups can be optionally substituted. Non-limiting examples include, for example, para-anisyl, meta-t-butoxyphenyl, and methylendioxyphenyl.

As used herein, "carboxy" refers to a —C(=O)OH group.

As used herein, "alkanoyl" refers to a —C(=O)-alkyl group, wherein alkyl is as previously defined. Exemplary alkanoyl groups include acetyl (ethanoyl), n-propanoyl, n-butanoyl, 2-methylpropanoyl, n-pentanoyl, 2-methylbutanoyl, 3-methylbutanoyl, 2,2-dimethylpropanoyl, heptanoyl, decanoyl, and palmitoyl.

As used herein, "heterocyclic" refers to a monocyclic or multicyclic ring system carbocyclic radical containing from about 4 to about 10 members, and all combinations and subcombinations of ranges therein, wherein one or more of the members is an element other than carbon, for example, nitrogen, oxygen or sulfur. The heterocyclic group may be aromatic or nonaromatic. Non-limiting examples include, for example, pyrrole and piperidine groups.

As used herein, "halo" refers to fluoro, chloro, or bromo.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, "side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, ileus, opioid bowel dysfunction, constipation, nausea, vomiting, or a combination thereof.

As used herein, "ileus" refers to the obstruction of the bowel or gut, especially the colon. See, e.g., *Dorland's Illustrated Medical Dictionary*, p. 816, 27th ed. (W. B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W. B. Saunders Company, Philadelphia 1988). Ileus may be diagnosed by the disruption of normal coordinated movements of the gut, resulting in failure of the propulsion of intestinal contents. See, e.g., Resnick, *J. Am. J. of Gastroenterology*, 1992, 751 and Resnick, *J. Am. J. of Gastroenterology*, 1997, 92, 934. In some instances, particularly following surgery, including surgery of the abdomen, the bowel dysfunction may become quite severe, lasting for more than a week and affecting more than one portion of the gastrointestinal tract. This condition is often referred to as post-surgical (or post-operative) paralytic ileus and most frequently occurs after laparotomy (see Livingston, E. H. and Passaro, E. D. Jr., *Digestive Diseases and Sciences*, 1990, 35, 121). Similarly, post-partum ileus is a common problem for women in the period following childbirth, and is thought to be caused by similar fluctuations in natural opioid levels as a result of birthing stress.

As used herein, "opioid bowel dysfunction" or "OBD" refers to a reduction in frequency of bowel movements since beginning opioid therapy, generally less than about 3 spontaneous bowel movements per week along with one of more of difficulty in expelling stool, lumpy or hard stools, sensation of anorectal obstruction, or sensation of incomplete evacuation. Opioid bowel dysfunction may include the constellation of constipation, abdominal cramping, bloating, nausea, gastroesophageal reflux, and combinations thereof.

As used herein, "effective amount" refers to an amount of a compound as described herein that may be therapeutically effective to inhibit, prevent, or treat the symptoms of particular disease, disorder, or side effect. Such diseases, disorders and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount," when used in connection with opioids, for example, for the treatment of pain, refers to the treatment and/or prevention of the painful condition. The term "effective amount," when used in connection with peripheral μ opioid antagonists, refers to the treatment and/or prevention of side effects typically associated with opioids including, f6r example, such side effects as ileus, opioid bowel dysfunction, constipation, nausea, vomiting, or a combination thereof.

As used herein, "in combination with," "combination therapy" and "combination products" refer, in certain embodiments, to the concurrent administration to a patient of antiemetic agents and peripheral μ opioid antagonists, including, for example, the compounds of formula I, or to the concurrent administration to a patient of antiemetic agents, peripheral μ opioid antagonists, and opioids. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

Certain acidic or basic compounds of the present invention may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "prodrug" refers to compounds specifically designed to maximize the amount of active species that reaches the desired site of reaction that are of themselves typically inactive or minimally active for the activity desired, but through biotransformation are converted into biologically active metabolites.

As used herein, "stereoisomers" refers to compounds that have identical chemical constitution, but differ as regards the arrangement of the atoms or groups in space.

When any variable occurs more than one time in any constituent or in any formula, its definition in each occurrence is independent of its definition at every other occurrence. Combinations of substituents and/or variables are permissible only if such combinations result in stable compounds.

The piperidines derivatives useful in the solid dispersions of the invention as illustrated in formula I can occur as the trans and cis stereochemical isomers at the 3- and 4-positions of the piperidine ring. In the most preferred compounds of formula I, the $R^2$ substituent and the $R^4$ substituent are in the "trans" orientation on the piperidine.

In addition to the "cis" and trans" orientation of the $R^2$ substituent and the $R^4$ substituent of formula I, the absolute stereochemistry of the carbon atoms bearing $R^2$ substituent and the $R^4$ substituent of formula I is also defined as using the commonly employed "R" and "S" definitions (Orchin et al., *The Vocabulary of Organic Chemistry*, John Wiley and Sons, Inc., page 126, which is incorporated herein by reference). The preferred compounds of the present invention are those in which the configuration of both the $R^2$ substituent and the $R^4$ substituents of formula I on the piperidine ring are "R."

Furthermore, asymmetric carbon atoms may be introduced into the molecule depending on the structure of $R^4$. As such, these classes of compounds can exist as the individual "R" or "S" stereoisomers at these chiral centers, or the racemic mixture of the isomers, and all are contemplated as within the scope of the present invention. Preferably, a substantially pure stereoisomer of the compounds of this invention is used, i.e., an isomer in which the configuration at the chiral center is "R" or "S", i.e., those compounds in which the configuration at the three chiral centers I preferably 3R, 4R, S or 3R, 4R, R.

As used herein, "peripheral" or "peripherally-acting" refers to an agent that acts outside of the central nervous system.

As used herein, "centrally-acting" refers to an agent that acts within the central nervous system.

The solid dispersions of the present invention involve a peripheral opioid antagonist compound. The term "peripheral" designates that the compound acts primarily on physiological systems and components external to the central nervous system. In preferred form, the peripheral opioid antagonist compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5% and most preferably 0% of the pharmacological activity of the compounds employed in the present methods is exhibited in the CNS.

Furthermore, it is preferred in certain embodiments of the invention where the compound is administered to antagonize the peripheral side effects of an opioid that the compound does not substantially cross the blood-brain barrier and thereby decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following intravenous administration.

U.S. Pat. No. 6,45 1,806 and U.S. Pat. No. 6,469,030 disclose methods and compositions comprising opioids and opioid antagonists, including peripheral µ opioid antagonists, the disclosures of which are incorporated herein by reference in their entirety. The solid dispersions are useful, inter alia, for treating and/or preventing side effects associated with opioids including ileus, opioid bowel dysfunction, constipation, nausea, vomiting, or a combination thereof, for treating and/or preventing pain, for treating and/or preventing ileus, and for treating and/or preventing opioid bowel dysfunction.

Accordingly, in one embodiment, the present invention provides solid dispersions, comprising:

at least one pharmaceutically-acceptable excipient selected from the group consisting of hydroxypropyl methylcellulose (HPMC), polyvinylpyrrolidone homopolymer (PVP), polyvinylpyrrolidone copolymer (including poly(vinylpyrrolidone/vinyl acetate) (PVP/VAc)), and mixtures thereof; and at least one compound of formula I:

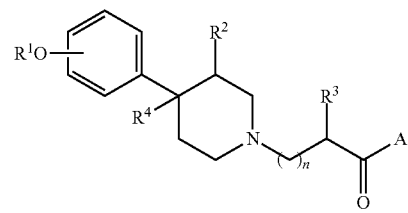

wherein said compound is in a solid amorphous form;
wherein said amorphous form is stable; and
wherein:
$R^1$ is hydrogen or alkyl;
$R^2$ is hydrogen, alkyl, or alkenyl;
$R^3$ is hydrogen, alkyl, alkenyl, aryl, cycloalkyl, cycloalkenyl, cycloalkyl-substituted alkyl, cycloalkenyl-substituted alkyl, or aralkyl;

R⁴ is hydrogen, alkyl, or alkenyl;

A is OR⁵ or NR⁶R⁷;

R⁵ is hydrogen, alkyl, alkenyl, cycloalkyl, cycloalkenyl, cycloalkyl-substituted alkyl, cycloalkenyl-substituted alkyl, or aralkyl;

R⁶ is hydrogen or alkyl;

R⁷ is hydrogen, alkyl, alkenyl, cycloalkyl, aryl, cycloalkyl-substituted alkyl, cycloalkenyl, cycloalkenyl-substituted alkyl, aralkyl, aralkyl, or alkylene substituted B or, together with the nitrogen atom to which they are attached, R⁶ and R⁷ form a heterocyclic ring;

B is

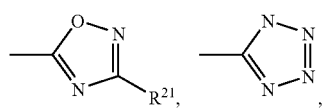

C(=O)W or NR⁸R⁹;

R⁸ is hydrogen or alkyl;

R⁹ is hydrogen, alkyl, alkenyl, cycloalkyl-substituted alkyl, cycloalkyl, cycloalkenyl, cycloalkenyl-substituted alkyl, aryl or aralkyl or, together with the nitrogen atom to which they are attached, R⁸ and R⁹ form a heterocyclic ring;

W is OR¹⁰, NR¹¹R¹², or OE;

R¹⁰ is hydrogen, alkyl, alkenyl, cycloalkyl, cycloalkenyl, cycloalkyl-substituted alkyl, cycloalkenyl-substituted alkyl, or aralkyl;

R¹¹ is hydrogen or alkyl;

R¹² is hydrogen, alkyl, alkenyl, aryl, cycloalkyl, cycloalkenyl, cycloalkyl-substituted alkyl, cycloalkenyl-substituted alkyl, aralkyl or alkylene substituted C(=O)Y or, together with the nitrogen atom to which they are attached, R¹¹ and R¹² form a heterocyclic ring;

E is

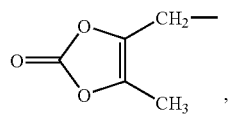

alkylene substituted (C=O)D, or —R¹³OC(=O)R¹⁴;

R¹³ is alkyl-substituted alkylene;

R¹⁴ is alkyl;

D is OR¹⁵ or NR¹⁶R¹⁷;

R¹⁵ is hydrogen, alkyl, alkenyl, cycloalkyl, cycloalkenyl, cycloalkyl-substituted alkyl, cycloalkenyl-substituted alkyl, or aralkyl;

R¹⁶ is hydrogen, alkyl, alkenyl, aryl, aralkyl, cycloalkyl, cycloalkenyl, cycloalkyl-substituted alkyl, or cycloalkenyl-substituted alkyl;

R¹⁷ is hydrogen or alkyl or, together with the nitrogen atom to which they are attached, R¹⁶ and R¹⁷ form a heterocyclic ring;

Y is OR¹⁸ or NR¹⁹R²⁰;

R¹⁸ is hydrogen, alkyl, alkenyl, cycloalkyl, cycloalkenyl, cycloalkyl-substituted alkyl, cycloalkenyl-substituted alkyl, or aralkyl;

R¹⁹ is hydrogen or alkyl;

R²⁰ is hydrogen, alkyl, alkenyl, aryl, cycloalkyl, cycloalkenyl, cycloalkyl-substituted alkyl, cycloalkenyl-substituted alkyl, or aralkyl or, together with the nitrogen atom to which they are attached, R¹⁹ and R²⁰ form a heterocyclic ring;

R²¹ is hydrogen or alkyl; and n is 0 to 4.

Suitable polyvinylpyrrolidones (PVP) are all types of PVP with Fikentscher K values of from 10 to 110, including K12 (about 2,000-3,000 Daltons), K17 (about 7,000-10,000 Daltons), K25 (about 28,000-34,000 Daltons), K29/32 (about 44,000-58,000) and K90 (about 1 million-1.5 million Daltons). K-value, short for Fikentschers K-value, is a measure of a polymer's average molecular weight. The test method used to calculate the K-value is determined by ISO 1628-2 (DIN 53726) (Determination of the viscosity of polymers in dilute solution using capillary viscometers). Mixtures of polyvinylpyrrolidone with polyvinyl acetate are also useful.

In preferred embodiments, the weight ratio of the compound of formula I to the pharmaceutically-acceptable excipient is about 5:95 to about 75:25, preferably at least about 10:90, more preferably at least about 15:85, even more preferably at least about 20:80, yet more preferably at least about 25:75, and yet even more preferably at least about 30:70.

In certain preferred embodiments, the compositions of the invention may include an opioid, provided that its inclusion does not interfere with the bioavailability of the compound of formula I. Suitable opioids include alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, and mixtures thereof. Preferred opioids include morphine, codeine, oxycodone, hydrocodone, dihydrocodeine, propoxyphene, fentanyl, and tramriadol.

The solid dispersions of the present invention may further include one or more other active ingredients conventionally employed in analgesic and/or cough-cold-antitussive combination products, provided that its inclusion does not interfere with the bioavailability of the compound of formula I. Such conventional ingredients include, for example, aspirin, acetaminophen, phenylpropanolamine, phenylephrine, chlorpheniramine, caffeine, and/or guaifenesin. Typical or conventional ingredients that may be included are described, for example, in the *Physicians' Desk Reference*, 1999, the disclosure of which is hereby incorporated herein by reference, in its entirety.

In addition, the solid dispersion of the invention may further include one or more compounds that may be designed to enhance the analgesic potency of the opioid and/or to reduce analgesic tolerance development, provided that its inclusion does not interfere with the bioavailability of the compound of formula I. Such compounds include, for example, dextromethorphan or other NMDA antagonists (Mao, M. J. et al., *Pain* 1996, 67, 361), L-364,718 and other CCK antagonists (Dourish, C. T. et al., *Eur. J. Pharmacol.*, 1988, 147, 469), NOS inhibitors (Bhargava, H. N. et al., *Neuropeptides*, 1996, 30, 219), PKC inhibitors (Bilsky, E. J. et al., *J. Pharmacol. Exp. Ther.* 1996, 277, 484), and dynorphin antagonists or antisera (Nichols, M. L. et al., *Pain*, 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

The solid dispersions of the present invention may be in a variety of solid dosage forms, including tablets, capsules, and lozenges.

Preferred 4-aryl-piperidine derivatives include, for example, the compounds disclosed in U.S. Pat. No. 5,250,542; U.S. Pat. No. 5,159,081; U.S. Pat. No. 5,270,328; and U.S. Pat. No. 5,434,171, U.S. Pat. No. 6,451,806 and U.S. Pat. No. 6,469,030, the disclosures of which are hereby incorporated herein by reference, in their entireties.

In preferred embodiments, the compound of formula I is a trans 3,4-isomer.

In certain embodiments employing compounds of formula I, it is preferred that
$R^1$ is hydrogen;
$R^2$ is alkyl;
n is 1 or 2;
$R^3$ is benzyl, phenyl, cyclohexyl, or cyclohexylmethyl; and
$R^4$ is alkyl.

In certain embodiments employing compounds of formula I, it is preferred that
A is $OR^5$; and
$R^5$ is hydrogen or alkyl.

In certain embodiments employing compounds of formula I, it is preferred that
A is $NR^6R^7$;
$R^6$ is hydrogen;
$R^7$ is alkylene substituted B; and
B is C(O)W.

In certain embodiments employing compounds of formula I, it is preferred that
$R^7$ is $(CH_2)_q$—B;
q is about 1 to about 3;
W is $OR^{10}$; and
$R^{10}$ is hydrogen, alkyl, phenyl-substituted alkyl, cycloalkyl or cycloalkyl-substituted alkyl.

In certain embodiments including compounds of formula I, it is preferred that
W is $NR^{11}R^{12}$
$R^{11}$ is hydrogen or alkyl; and
$R^{12}$ is hydrogen, alkyl or alkylene substituted C(=O)Y.

In certain embodiments employing compounds of formula I, it is preferred that
$R^{12}$ is $(CH_2)_mC(O)Y$;
m is 1 to 3;
Y is $OR^{18}$ or $NR^{19}R^{20}$; and
$R^{18}$, $R^{19}$ and $R^{20}$ are independently hydrogen or alkyl.

In certain embodiments employing compounds of formula I, it is preferred that
W is OE;
E is $CH_2C(=O)D$;
D is $OR^{15}$ or $NR^{16}R^{17}$;
$R^{15}$ is hydrogen or alkyl;
$R^{16}$ is methyl or benzyl; and
$R^{17}$ is hydrogen.

In certain embodiments employing compounds of formula I, it is preferred that
W is OE;
E is $R^{13}OC(=O)R^{14}$;
$R^{13}$ is —CH(CH$_3$)— or —CH(CH$_2$CH$_3$)—; and
$R^{14}$ is alkyl.

In certain embodiments employing compounds of formula I, it is preferred that the configuration at positions 3 and 4 of the piperidine ring is each R.

Preferred compounds of formula I include:
Q-CH$_2$CH(CH$_2$(C$_6$H$_5$))C(O)OH,
Q-CH$_2$CH$_2$CH(C$_6$H$_5$)C(O)NHCH$_2$C(O)OCH$_2$CH$_3$,
Q-CH$_2$CH$_2$CH(C$_6$H$_5$)C(O)NHCH$_2$C(O)OH,
Q-CH$_2$CH$_2$CH(C$_6$H$_5$)C(O)NHCH$_2$C(O)NHCH$_3$,
Q-CH$_2$CH$_2$CH(C$_6$H$_5$)C(O)NHCH$_2$C(O)NHCH$_2$CH$_3$,
G-NH(CH$_2$)$_2$C(O)NH$_2$,
G-NH(CH$_2$)$_2$C(O)NHCH$_3$,
G-NHCH$_2$C(O)NH$_2$,
G-NHCH$_2$C(O)NHCH$_3$,
G-NHCH$_2$C(O)NHCH$_2$CH$_3$,
G-NH(CH$_2$)$_3$C(O)OCH$_2$CH$_3$,
G-NH(CH$_2$)$_3$C(O)NHCH$_3$,
G-NH(CH$_2$)$_2$C(O)OH,
G-NH(CH$_2$)$_3$C(O)OH,
Q-CH$_2$CH(CH$_2$(C$_6$H$_{11}$))C(O)NHCH$_2$C(O)OH,
Q-CH$_2$CH(CH$_2$(C$_6$H$_{11}$))C(O)NH(CH$_2$)$_2$C(O)OH,
Q-CH$_2$CH(CH$_2$(C$_6$H$_{11}$))C(O)NH(CH$_2$)$_2$C(O)NH$_2$,
Z-NHCH$_2$C(O)OCH$_2$CH$_3$,
Z-NHCH$_2$C(O)OH,
Z-NHCH$_2$C(O)NH$_2$,
Z-NHCH$_2$C(O)N(CH$_3$)$_2$,
Z-NHCH$_2$C(O)NHCH(CH$_3$)$_2$,
Z-NHCH$_2$C(O)OCH$_2$CH(CH$_3$)$_2$,
Z-NH(CH$_2$)$_2$C(O)OCH$_2$(C$_6$H$_5$),
Z-NH(CH$_2$)$_2$C(O)OH,
Z-NH(CH$_2$)$_2$C(O)NHCH$_2$CH$_3$,
Z-NH(CH$_2$)$_3$C(O)NHCH$_3$,
Z-NHCH$_2$C(O)NHCH$_2$C(O)OH,
Z-NHCH$_2$C(O)OCH$_2$C(O)OCH$_3$,
Z-NHCH$_2$C(O)O(CH$_2$)$_4$CH$_3$,
Z-NHCH$_2$C(O)OCH$_2$C(O)NHCH$_3$,
Z-NHCH$_2$C(O)O-(4-methoxycyclohexyl),
Z-NHCH$_2$C(O)OCH$_2$C(O)NHCH$_2$(C$_6$H$_5$) and
Z-NHCH$_2$C(O)OCH(CH$_3$)OC(O)CH$_3$;
wherein:
Q represents

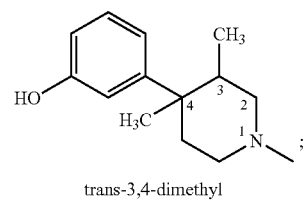

trans-3,4-dimethyl

G represents

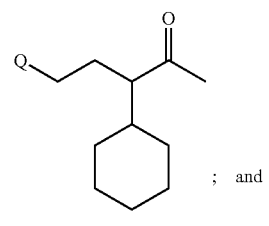

; and

Z represents

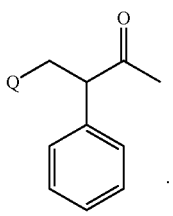

More preferred compounds of formula I include:
(3R,4R,S)-Z-NHCH$_2$C(O)OCH$_2$CH(CH$_3$)$_2$,
(+)-Z-NHCH$_2$C(O)OH,
(−)-Z-NHCH$_2$C(O)OH,
(3R,4R,R)-Z-NHCH$_2$C(O)-OCH$_2$CH(CH$_3$)$_2$,
(3S,4S,S)-Z-NHCH$_2$C(O)OCH$_2$CH(CH$_3$)$_2$,
(3S,4S,R)-Z-NHCH$_2$C(O)OCH$_2$CH(CH$_3$)$_2$,
(3R,4R)-Z-NHCH$_2$C(O)NHCH$_2$(C$_6$H$_5$) and
(3R,4R)-G-NH(CH$_2$)$_3$C(O)OH.
wherein Q, Z and G are as defined above.

Even more preferred compounds of formula I include (+)-Z-NHCH$_2$C(O)OH and (−)-Z-NHCH$_2$C(O)OH, wherein Z is as defined above. It is especially preferred when said compound is (+)-Z-NHCH$_2$C(O)OH.

Even more preferred compounds of formula I include Q-CH$_2$CH(CH$_2$(C$_6$H$_5$))C(O)OH, wherein Q is as defined above. It is especially preferred when said compound is (3R, 4R, S)-Q-CH$_2$CH(CH$_2$(C$_6$H$_5$))C(O)OH.

Compounds of formula I that act locally on the gut, have high potency, and are orally active are most preferred. A particularly preferred embodiment of the present invention is the compound (+)-Z-NHCH$_2$C(O)OH, i.e., the compound of the following formula (II):

II

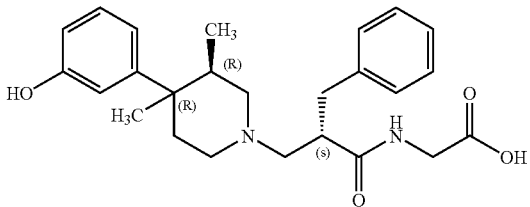

The compound of formula (II) has low solubility in water except at low or high pH conditions. Zwitterionic character may be inherent to the compound, and may impart desirable properties such as poor systemic absorption and sustained local effect on the gut following oral administration.

In especially preferred embodiments, the compound of a formula I is a substantially pure stereoisomer.

In yet another embodiment, the invention is directed to methods of preventing or treating a side effect associated with an opioid in a patient, comprising the step of:
administering to said patient in need thereof an effective amount of the above-described composition. The methods are useful in the prevention and treatment of ileus, opioid bowel dysfunction, constipation, nausea, vomiting, and combinations thereof, particularly postoperative ileus, postoperative nausea, or postoperative vomiting.

In other embodiments, the invention is directed to methods of preventing or treating pain in a patient, comprising the step of:
administering to said patient in need thereof an effective amount of the above-described composition. In preferred embodiments, the composition further comprises at least one opioid.

In other embodiments, the invention is directed to methods of preventing or treating ileus in a patient, comprising the step of:
administering to said patient in need thereof an effective amount of the above-described composition. In preferred embodiments, the composition further comprises at least one opioid.

In other embodiments, the invention is directed to methods of preventing or treating opioid bowel dysfumction in a patient, comprising the step of:
administering to said patient in need thereof an effective amount of the above-described composition. In preferred embodiments, the composition further comprises at least one opioid.

The present invention is directed to solid dispersions involving opioid compounds. As discussed above, such opioid compounds may be useful, for example, in the treatment and/or prevention of pain. However, as also discussed above, undesirable side effects including, for example, ileus, opioid bowel dysfunction constipation, nausea, vomiting, or a combination thereof, especially post-operative ileus, nausea and/or vomiting, as well as other side effects, may frequently occur in patients receiving opioid compounds. By virtue of the solid dispersions of the present invention, effective and desirable inhibition of undesirable side effects that may be associated with opioid compounds may be advantageously achieved. Accordingly, combination solid dispersions, where opioids are combined or co-administered with suitable peripheral μ opioid antagonist compounds, may afford an efficacy advantage over the compounds and agents alone.

In this connection, as discussed above, patients are often administered opioids for the treatment, for example, of painful conditions. However, as noted above, undesirable side effects such as, for example, ileus, opioid bowel dysfunction, constipation, nausea, vomiting, or a combination thereof, may result from opioid administration. These undesirable side effects may act as a limiting factor in connection with the amount of opioid that may be administered to the patient. That is, the amount of opioid capable of being administered to the patient may be limited due to the undesired occurrence of the aforementioned side effects. The limited amounts of opioid that may be administered to a patient may, in turn, result in a disadvantageously diminished degree of pain alleviation. The present combination methods and compositions may be used to advantageously increase the amount of opioid administered to a patient, thereby obtaining enhanced pain alleviation, while reducing, minimizing and/or avoiding undesirable side effects that may be associated with the opioid. The peripheral μ opioid antagonists employed in the methods and compositions of the present invention preferably have substantially no central nervous system activity and, accordingly, desirably do not affect the pain killing efficacy of the opioid.

While not intending to be bound by any theory or theories of operation, it is contemplated that opioid side effects, such as ileus, opioid bowel dysfunction, constipation, nausea, vomiting, or a combination thereof, may result from undesirable interaction of the opioid with peripheral μ receptors. Administration of a peripherally-acting μ opioid antagonist according to the methods of the present invention may block interaction of the opioid compounds with the μ receptors, thereby preventing and/or inhibiting the side effects, including ileus, opioid bowel dysfunction, constipation, nausea, vomiting, and combinations thereof, and including in particular post-operative or post-partum ileus, nausea and/or vomiting.

Other μ opioid antagonist compounds that may be employed in the methods and compositions of the present invention, in addition to those exemplified above, would be readily apparent to one of ordinary skill in the art, once armed with the teachings of the present disclosure.

The compounds employed in the methods of the present invention may exist in prodrug form. As used herein, "prodrug" is intended to include any covalently bonded carriers that release the active parent drug, for example, as according to formulas I, employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the solid dispersions of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The 4-aryl-piperidine derivatives of formula I of the present invention may be synthesized employing methods taught, for example, in U.S. Pat. No. 5,250,542, U.S. Pat. No. 5,434,171, U.S. Pat. No. 5,159,081, U.S. Pat. No. 5,270,328, U.S. Pat. No. 6,451,806, U.S. Pat. No. 6,469,030, and Werner, J. A., et al., *Journal of Organic Chemistry*, 61, 587-597 (1996), the disclosures of which are hereby incorporated herein by reference in their entireties. For example, the 3-substituted-4-methyl-4-(3-hydroxy- or alkanoyloxyphenyl)piperidine derivatives employed as starting materials in the synthesis of the present compounds may be prepared by the general procedure taught in U.S. Pat. No. 4,115,400 and U.S. Pat. No. 4,891,379, the disclosures of which are hereby incorporated herein by reference in their entireties. The starting material for the synthesis of compounds described herein, (3R,4R)-4-(3-hydroxypheny)-3,4-dimethylpiperidine, may be prepared by the procedures described in U.S. Pat. No. 4,581,456 and U.S. Pat. No. 5,136,040, the disclosures of which are hereby incorporated herein by reference, in their entirety, but adjusted as described such that the β-stereochemistry is preferred.

The first step of the process may involve the formation of the 3-alkoxyphenyllithium reagent by reacting 3-alkoxybromobenzene with an alkyllithium reagent. This reaction may be performed under inert conditions and in the presence of a suitable non-reactive solvent such as dry diethyl ether or preferably dry tetrahydrofuran. Preferred alkyllithium reagents used in this process are n-butyl lithium, and especially sec-butyl lithium. Generally, approximately an equimolar to slight excess of alkyllithium reagent may be added to the reaction mixture. The reaction may be conducted at a temperature of from about −20° C. and about −100° C., more preferably from about −50° C. to about −55° C.

Once the 3-alkoxyphenyllithium reagent has formed, approximately an equimolar quantity of a 1-alkyl-4-piperidone may be added to the mixture while maintaining the temperature between about −20° C. and about −100° C. The reaction is typically complete after about 1 to 24 hours. At this point, the reaction mixture may be allowed to gradually warm to room temperature. The product may be isolated by the addition to the reaction mixture of a saturated sodium chloride solution to quench any residual lithium reagent. The organic layer may be separated and further purified if desired to provide the appropriate 1-alkyl-4-(3-alkoxyphenyl)piperidinol derivative.

The dehydration of the 4-phenylpiperidinol prepared above may be accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid in toluene or benzene. This reaction may be typically conducted under reflux conditions, more generally from about 50° C. and 150° C. The product thus formed may be isolated by basifying an acidic aqueous solution of the salt form of the product and extracting the aqueous solution with a suitable water immiscible solvent. The resulting residue following evaporation can then be further purified if desired.

The 1-alkyl-4-methyl-4-(3-alkoxyphenyl)tetrahydropyridine derivatives may be prepared by a metalloenamine alkylation. This reaction is preferably conducted with n-butyl lithium in tetrahydrofuran (THF) under an inert atmosphere, such as nitrogen or argon. Generally, a slight excess of n-butyl lithium may be added to a stirring solution of the 1-alkyl-4-(3-alkoxyphenyl)-tetrahydropyridine in THF cooled to a temperature in the range of from about −50° C. to about 0° C., more preferably from about −20° C. to −10° C. This mixture may be stirred for approximately 10 to 30 minutes followed by the addition of approximately from 1.0 to 1.5 equivalents of methyl halide to the solution while maintaining the temperature of the reaction mixture below 0° C. After about 5 to 60 minutes, water may be added to the reaction mixture and the organic phase may be collected. The product can be purified according to standard procedures, but the crude product is preferably purified by either distilling it under vacuum or slurrying it in a mixture of hexane:ethyl acetate (65:35, v:v) and silica gel for about two hours. According to the latter procedure, the product may be then isolated by filtration followed by evaporating the filtrate under reduced pressure.

The next step in the process may involve the application of the Mannich reaction of aminomethylation to non-conjugated, endocyclic enamines. This reaction is preferably carried out by combining from about 1.2 to about 2.0 equivalents of aqueous formaldehyde and about 1.3 to 2.0 equivalents of a suitable secondary amine in a suitable solvent. While water may be the preferred solvent, other non-nucleophilic solvents, such as acetone and acetonitrile can also be employed in this reaction. The pH of this solution may be adjusted to approximately 3.0 to 4.0 with an acid that provides a non-nucleophilic anion. Examples of such acids include sulfuric acid, the sulfonic acids such as methanesulfonic acid and p-toluenesulfonic acid, phosphoric acid, and tetrafluoroboric acid, with sulfuric acid being preferred. To this solution may be added one equivalent of a 1-alkyl-4-methyl-4-(3-alkoxyphenyl)tetrahydropyridine, typically dissolved in aqueous sulfuric acid, and the pH of the solution may be readjusted with the non-nucleophilic acid or a suitable secondary amine. The pH is preferably maintained in the range of from about 1.0 to about 5.0, with a pH of about 3.0 to about 3.5 being more preferred during the reaction. The reaction is substantially complete after about 1 to 4 hours, more typically about 2 hours, when conducted at a temperature in the range of from about 50° C. to about 80° C., more preferably about 70° C. The reaction may then be cooled to approximately 30° C., and added to a sodium hydroxide solution. This solution may then be extracted with a water immiscible organic solvent, such as hexane or ethyl acetate, and the organic phase, following thorough washing with water to remove any residual formaldehyde, may be evaporated to dryness under reduced pressure.

The next step of the process may involve the catalytic hydrogenation of the prepared 1-alkyl-4-methyl-4-(3-alkoxyphenyl)-3-tetrahydropyridinemethanamine to the corresponding trans-1-alkyl-3,4-dimethyl-4-(3-alkoxyphenyl)piperidine. This reaction actually occurs in two steps. The first step is the hydrogenolysis reaction wherein the exo C-N bond is reductively cleaved to generate the 3-methyltetrahydropyridine. In the second step, the 2,3-double bond in the tetrahydropyridine ring is reduced to afford the desired piperidine ring.

Reduction of the enamine double bond introduced the crucial relative stereochemistry at the 3 and 4 carbon atoms of the piperidine ring. The reduction generally does not occur with complete stereoselectivity. The catalysts employed in the process may be chosen from among the various palladium and preferably platinum catalysts.

The catalytic hydrogenation step of the process is preferably conducted in an acidic reaction medium. Suitable solvents for use in the process include the alcohols, such as methanol or ethanol, as well as ethyl acetate, tetrahydrofuran, toluene, hexane, and the like.

Proper stereochemical outcome may be dependent on the quantity of catalyst employed. The quantity of catalyst required to produce the desired stereochemical result may be dependent upon the purity of the starting materials in regard to the presence or absence of various catalyst poisons.

The hydrogen pressure in the reaction vessel may not be critical but can be in the range of from about 5 psi to about 200 psi. Concentration of the starting material by volume is preferably about 20 mL of liquid per gram of starting material, although an increased or decreased concentration of the starting material can also be employed. Under the conditions specified herein, the length of time for the catalytic hydrogenation may not be critical because of the inability for over-reduction of the molecule. While the reaction can continue for up to about 24 hours or longer, it may not be necessary to continue the reduction conditions after the uptake of the theoretical two moles of hydrogen. The product may then be isolated by filtering the reaction mixture for example through infusorial earth, and evaporating the filtrate to dryness under reduced pressure. Further purification of the product thus isolated may not be necessary and preferably, the diastereomeric mixture may be carried directly on to the following reaction.

The alkyl substituent may be removed from the 1-position of the piperidine ring by standard dealkylation procedures. Preferably, a chloroformate derivative, especially the vinyl or phenyl derivatives, may be employed and removed with acid. Next, the prepared alkoxy compound may be dealkylated to the corresponding phenol. This reaction may be generally carried out by reacting the compound in a 48% aqueous hydrobromic acid solution. This reaction may be substantially complete after about 30 minutes to about 24 hours when conducted at a temperature of from about 50° C. to about 150° C., more preferably at the reflux temperature of the reaction mixture. The mixture may then be worked up by cooling the solution, followed by neutralization with base to an approximate pH of 8. This aqueous solution may be extracted with a water immiscible organic solvent. The residue following evaporation of the organic phase may then be used directly in the following step.

The compounds employed as starting materials to the compounds of the invention can also be prepared by brominating the 1-alkyl-4-methyl-4-(3-alkoxyphenyl)-3-tetrahydropyridinemethanamine at the 3-position, lithiating the bromo compound thus prepared, and reacting the lithiated intermediate with a methylhalide, such as methyl bromide to provide the corresponding 1-alkyl-3,4-dimethyl-4-(3-alkoxyphenyl)tetrahydropyridinemethanamine. This compound may then be reduced and converted to the starting material as indicated above.

As noted above, the compounds useful in the solid dispersions of the present invention can exist as the individual stereoisomers. Preferably, reaction conditions are adjusted as disclosed in U.S. Pat. No. 4,581,456 or as set forth in Example 1 of U.S. Pat. No. 5,250,542 to be substantially stereoselective and provide a racemic mixture of essentially two enantiomers. These enantiomers may then be resolved. A procedure which may be employed to prepare the resolved starting materials used in the synthesis of these compounds includes treating a racemic mixture of alkyl-3,4-dimethyl-4-(3-alkoxyphenyl)piperidine with either (+)- or (−)-ditoluoyl tartaric acid to provide the resolved intermediate. This compound may then be dealkylated at the position with vinyl chloroformate and finally converted to the desired 4-(3-hydroxyphenyl)piperidine isomer.

As will be understood by those skilled in the art, the individual enantiomers of the invention can also be isolated with either (+) or (−) dibenzoyl tartaric acid, as desired, from the corresponding racemic mixture of the compounds of the invention. Preferably, the (+)-trans enantiomer is obtained.

Although the (+)trans-3,4 stereoisomer is preferred, all of the possible stereoisomers of the compounds described herein are within the contemplated scope of the present invention. Racemic mixtures of the stereoisomers as well as the substantially pure stereoisomers are within the scope of the invention. The term "substantially pure," as used herein, refers to at least about 90 mole percent, more preferably at least about 95 mole percent and most preferably at least about 98 mole percent of the desired stereoisomer is present relative to other possible stereoisomers.

Intermediates can be prepared by reacting a 3,4-alkyl-substituted-4-(3-hydroxyphenyl)piperidine with a compound of the formula $LCH_2(CH_2)_{n-1}CHR^3C(O)E$ where L is a leaving group such as chlorine, bromine or iodine, E is a carboxylic acid, ester or amide and $R^3$ and n are as defined hereinabove. Preferably, L may be chlorine and the reaction is carried out in the presence of a base to alkylate the piperidine nitrogen. For example 4-chloro-2-cyclohexylbutanoic acid, ethyl ester can be contacted with (3R,4R)-4-(3-hydroxyphenyl)-3,4-dimethylpiperidine to provide 4-[(3R,4R)-4-(3-hydroxyphenyl)-3,4-dimethyl-1-piperidine]butanoic acid, ethyl ester. Although the ester of the carboxylic acid may be preferred, the free acid itself or an amide of the carboxylic acid may be used.

In alternative synthesis, the substituted piperidine can be contacted with a methylene alkyl ester to alkylate the piperidine nitrogen. For example, 2-methylene-3-phenylproponic acid, ethyl ester can be contacted with a desired piperidine to provide 2-benzyl-3-piperidinepropanoic acid ethyl ester.

Another synthetic route can involve the reaction of a substituted piperidine with a haloalkylnitrile. The nitrile group of the resulting piperidine alkylnitrile can be hydrolyzed to the corresponding carboxylic acid.

With each of the synthetic routes, the resulting ester or carboxylic acid can be reacted with an amine or alcohol to provide modified chemical structures. In the preparation of amides, the piperidine-carboxylic acid or piperidine-carboxylic acid ester may be reacted with an amine in the presence of a coupling agent such as dicyclohexylcarbodiimide, boric acid, borane-trimethylamine, and the like. Esters can be prepared by contacting the piperidine-carboxylic acid with the appropriate alcohol in the presence of a coupling agent such as p-toluenesulfonic acid, boron trifluoride etherate or N,N'-carbonyldiimidazole. Alternatively, the piperidine-carboxylic acid chloride can be prepared using a reagent such as thionyl chloride, phosphorus trichloride, phosphorus pentachloride and the like. This alkanoyl chloride can be reacted with the appropriate amine or alcohol to provide the corresponding amide or ester.

Amorphous forms of the compounds of formula I may be produced by conventional pharmaceutical processes, including melt quenching, freeze-drying (lyophilizing), spray-drying, milling, wet granulation, evaporation, and drying of solvated crystals. Lyophilization and evaporation are preferred techniques to prepare amorphous forms of the compounds of formula I. The existence of the amorphous form of the compounds of formula I may be determined by x-ray powder diffraction or by measuring for a glass transition temperature, for example, by differential scanning calorimetry, modulating differential scanning calorimetry, or dynamic mechanical analysis.

For example, amorphous alvimopan may be prepared by dissolving the drug compound in ethanol at a concentration of approximately 3 mg/mL. The solution may be filtered using a 0.2 μm nylon filter and rotary evaporated. Alternatively, an amorphous solid may be also generated by dissolving alvimopan into 1,4-dioxane:t-butanol:water (1:1:1) solvent mixtures followed by lyophilization. The solid material may be collected and preferably placed into a vacuum oven heated at ambient to about 100° C. for up to two days to remove any residual solvent. The resulting solids may be collected and stored.

As another example, amorphous alvimopan sodium salt may be prepared by dissolving alvimopan and the counter ion into ethanol or 1,4-dioxane:t-butanol:water (1:1:1) solvent mixtures with a counter ion:alvimopan ratio of 1:1 or 2:1. The solutions may be filtered using a 0.2 μm nylon filter and rotary evaporated or lyophilized. The solid material may be collected and placed into a vacuum oven heated at ambient, about 60° C., or about 100° C. for up to two days to remove any residual solvent. The resulting solids may be collected and stored.

Solid dispersions of the compounds of formula I may be produced by conventional pharmaceutical processes. For example, solid dispersions of alvimopan with HPMC, mannitol, PVP, or PVP/VAc may be prepared by dissolving the components in ethanol or 1,4-dioxane:t-butanol:water (1:1:1) solvent mixtures with a drug:excipient weight fraction of 70:30. The solutions may be filtered using a 0.2 μm nylon filter and rotary evaporated or lyophilized. The solid material may be collected and preferably placed into a vacuum oven heated at ambient to about 100° C. for up to two days to remove any residual solvent. The resulting solids may be collected and stored.

The amount of active compound(s) in such therapeutically useful compositions is preferably such that a suitable dosage will be obtained. Preferred compositions or preparations according to the present invention may be prepared so that a dosage unit form contains from about 0.1 to about 1000 mg of active compound.

Under ordinary conditions of storage and use, these preparations may contain a preservative to prevent the growth of microorganisms.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, parenteral administration will require a lower dosage than oral administration.

The combination products of this invention, such as solid dispersions comprising opioids in combination with a peripheral μ opioid antagonist compound, such as the compounds of formula I, may be in any solid dosage form, such as those described herein, and can also be administered in various ways, as described herein. In a preferred embodiment, the combination products of the invention are formulated together, in a single dosage form (that is, combined together in one dispersion, etc.). When the combination products are not formulated together in a single dosage form, the opioid compounds and the peripheral μ opioid antagonist compounds may be administered at the same time or simultaneously (that is, together), or in any order. When not administered at the same time or simultaneously, that is, when administered sequentially, preferably the administration of a peripheral μ opioid antagonist and opioid occurs less than about one hour apart, more preferably less than about 30 minutes apart, even more preferably less than about 15 minutes apart, and still more preferably less than about 5 minutes apart.

Although it is preferable that the peripheral μ opioid antagonists and opioids are administered in the same fashion (that is, for example, both orally), if desired, they may each be administered in different fashions (that is, for example, the opioid component of the combination product may be administered intravenously, and peripheral μ opioid antagonist component may be administered orally). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where an opioid compounds is combined with a peripheral μ opioid antagonist, for example, typically a daily dosage may range from about 0.01 to about 100 milligrams of the opioid (and all combinations and subcombinations of ranges therein) and about 0.001 to about 100 milligrams of the peripheral μ opioid antagonist (and all combinations and subcombinations of ranges therein) per kilogram of patient body weight. Preferably, the a daily dosage may be about 0.1 to about 10 milligrams of the opioid and about 0.01 to about 10 milligrams of the peripheral μ opioid antagonist per kilogram of patient body weight. Even more preferably, the daily dosage may be about 1.0 milligrams of the opioid and about 0.1 milligrams of the peripheral μ opioid antagonist per kilogram of patient body weight. With regard to a typical dosage form of this type of combination product, the opioid compounds (e.g., morphine) generally may be present in an amount of about 15 to about 200 milligrams and the peripheral μ opioid antagonists in an amount of about 0.1 to about 4 milligrams.

Compounds of formula I for use in the solid dispersions of the present invention have been characterized in opioid receptor binding assays showing preferential binding to μ opioid receptors. Studies in isolated tissues (guinea pig and mouse vas deferens) have shown that these compounds may act as antagonists with no measurable agonist activity. Studies in animals have demonstrated that the present compounds may reverse constipation in morphine-dependent mice when administered orally or parenterally at very low doses, and do not block the analgesic actions of morphine unless given in hundred-fold or higher doses. Collectively, the data indicate that the compounds described herein may have a very high degree of peripheral selectivity.

EXAMPLES

The present invention will now be illustrated by reference to the following specific, non-limiting examples. The examples are not intended to limit the scope of the present invention.

Materials

Alvimopan was prepared in accordance with the method below. Polyvinylpyrrolidone (PVP, average molecular weight 1,300,00 g/mol), poly(1-vinylpyrrolidone-co-vinyl acetate) (PVPVAc, average molecular weight 50,000), hydroxypropylmethyl cellulose (HPMC, average molecular weight 50,000), mannitol, solvents, and all other materials were commercially available. PVP/VAc is a random copolymer containing vinyl pyrrolidone and vinyl acetate at a molar ratio of 60:40.

Methods

Synthesis of Alvimopan

Alvimopan was prepared in accordance with the following synthetic procedure.

Synthesis of 1-bromo-3-(1-methylethoxy)benzene (Compound 1)

| Reagent | MW | Amount (kg) | Kilomoles | Molar Ratio |
|---|---|---|---|---|
| 3-Bromophenol | 173.01 | 80.0 | 0.4624 | 1.00 |
| 2-Bromopropane | 123.0 | 85.6 | 0.6959 | 1.51 |
| Potassium carbonate, ground | 138.2 | 96.0 | 0.6946 | 1.50 |
| Ethanol 1X* | 46.07 | 144 | — | — |
| Water | 18.02 | 739 | — | — |
| Hydrochloric acid, 31% | 36.46 | 6.6 | — | — |
| Sodium hydroxide, 50% w/w | 40.0 | 44.4 | — | — |
| Heptanes | 100.2 | 185 | — | — |

*Ethanol 1X was denatured with 0.5% toluene.

A reactor was charged with ground potassium carbonate (96.0 kg) and ethanol 1× (134 kg). The reaction mixture was adjusted to 20° C. to 25° C.

With agitation, 3-bromophenol (80.0 kg) was charged to the reactor while maintaining the temperature between 20° C. to 35° C. The transfer equipment was rinsed forward with ethanol 1× (5 kg). The temperature was adjusted to 20° C. to 25° C. 2-Bromopropane (85.6 kg) was charged to the reactor. The transfer equipment was rinsed forward with ethanol 1× (5 kg). Water (20 L) was charged to the reactor.

The solution in the reactor was heated to 60° C. to 65° C. and maintained in that range for a minimum of 16 hours. The mixture was cooled to 45° C. to 50° C. and the mixture was verified for 3-bromophenol. The mixture was warmed to 60° C. to 65° C. while awaiting the results. The mixture was cooled to 45° C. to 50° C. once more.

Water (303 L) was charged to the reactor. The reaction mixture was reduced to a concentrate volume of 400 L via atmospheric distillation. The concentrated mixture was cooled to 20° C. to 25° C.

Heptanes (185 kg) were charged to the reactor and then stirred at a temperature of 20° C. to 25° C. for a minimum of 20 minutes.

The biphasic solution was separated and the organic layer was washed with a solution of water (45 L) and hydrochloric acid, 31% (6.6 kg). The organic layer was washed with water (56 L) followed by a solution of water (49 L) and sodium hydroxide, 50% (4.4 kg). The organic layer was washed one final time with water (56 L).

The organic solution was dried via azeotropic distillation until no more water was collected. The reaction mixture was then reduced to a concentrate volume of 150 to 170 L via atmospheric distillation and cooled to 20 to 25° C. The solution was packaged for use in the next step. The packaged product (Compound 1) was sampled, tested: HPLC purity not less than 98% a/a and HPLC assay not less than 55% w/w.

Synthesis of cis-(±)-1,3-dimethyl-4-[3-(1-methylethoxy)phenyl]-4-piperidinol (Compound 2)

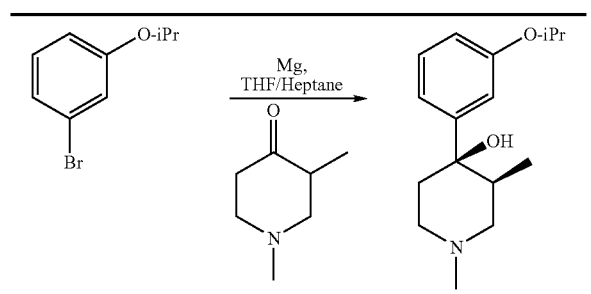

| Reagent | MW | Amount (kg) | Kilomoles | Molar Ratio |
|---|---|---|---|---|
| Compound 1 | 215.1 | 27.9 | 0.07514* | 1.21 |
| Magnesium turnings | 24.3 | 2.1 | 0.08642 | 1.39 |
| 1,3-Dimethyl-4-piperidone | 127.2 | 7.9 | 0.06211 | 1.00 |
| Tetrahydrofuran | 72.01 | 162 | — | — |
| Ammonium chloride | 53.5 | 6.6 | — | — |
| Water | 18.02 | 56 | — | — |
| Hyflo supercel | — | 4 | — | — |
| Heptanes | 100.2 | 86.5 | — | — |

*Calculated as per assay of reagent

The tetrahydrofuran to be used was sampled for water content prior to use in the lot.

A reactor was charged with tetrahydrofuran (18 kg) and heated to reflux without agitation. The solvent was maintained at reflux for 1 hour and cooled to 30° C. or less. A KF analysis was performed to ensure that the amount of water in the reactor meets the specifications. The THF was drained to waste and the reactor was dried.

Magnesium (2.1 kg) was charged to the reactor, followed by tetrahydrofuran (80 kg). With agitation, the reaction mixture was reduced to a concentrate volume of 40 to 44 L via atmospheric distillation. The concentrate was cooled to 40 to 45° C.

A portable agitation stainless steel tank was charged with tetrahydrofuran (18 kg) and agitated for a minimum of 20 minutes. A KF analysis was performed to ensure that the amount of water in the reactor meets the specifications. The THF was drained to waste.

The tank was charged with 1-bromo-3-(1-methylethoxy)benzene (27.9 kg) and tetrahydrofuran (31 kg). The solution was agitated at room temperature for a minimum of 20 minutes.

A 2.5 kg portion of the mixture in the tank was transferred into the reactor starting at a temperature of 40° C. to 45° C. With agitation, the mixture was maintained at 40° C. to 60° C. for a minimum of 30 minutes.

A second 2.5 kg portion of the mixture in the tank was transferred into the reactor starting at a temperature of 40° C. to 45° C. With agitation, the mixture was maintained at 40° C. to 60° C. for a minimum of 30 minutes.

A 5 kg portion of the mixture in the tank was transferred into the reactor starting at a temperature of 40° C. to 45° C. With agitation, the mixture was maintained at 40° C. to 60° C. for a minimum of 30 minutes.

The tank was charged with 1,3-dimethyl-4-piperidone (7.9 kg) and the transfer equipment was rinsed forward with tetrahydroftiran (5 kg).

A 15 kg portion of the mixture in the tank was transferred into the reactor over a minimum of 1 hour, starting at a temperature of 40° C. to 45° C. With agitation, the mixture was maintained at 40° C. to 60° C. for 15 to 30 minutes. The reaction mixture was cooled to 40° C. to 45° C.

A second 15 kg portion of the mixture in the tank was transferred into the reactor over a minimum of 1 hour, starting at a temperature of 40° C. to 45° C. With agitation, the mixture was maintained at 40° C. to 60° C. for 15 to 30 minutes. The reaction mixture was cooled to 40° C. to 45° C.

A third 15 kg portion of the mixture in the tank was transferred into the reactor over a minimum of 1 hour, starting at a temperature of 40 to 45° C. With agitation, the mixture was maintained at 40° C. to 60° C. for 15 to 30 minutes. The reaction mixture was cooled to 40° C. to 45° C.

The remainder of the mixture in the tank was transferred into the reactor over a minimum of 1 hour, starting at a temperature of 40° C. to 45° C. The transfer equipment was rinsed forward with THF (5 kg). With agitation, the mixture was maintained at 40° C. to 60° C. for 15 to 30 minutes. The mixture was cooled to 40° C. to 45° C.

After the reaction was complete, the mixture was cooled to 20° C. to 25° C.

A second reactor was charged with water (40 L) and ammonium chloride (6.6 kg). With moderate agitation, the mixture was maintained at 20° C. to 25° C. for a minimum of 20 minutes.

Once the solids have dissolved, Hyflo supercel (4 kg) was charged into the second reactor. The aqueous mixture was cooled to 0° C. to 5° C.

With agitation, the organic mixture in the first reactor was transferred through to the second reactor. The transfer equipment was rinsed forward with THF (5 kg). The mixture was warmed to 20° C. to 25° C. and maintained for a minimum of 15 minutes.

The mixture was filtered into the first reactor, rinsed forward with heptanes (2×6 kg), and maintained at 20° C. to 25° C. for a minimum of 20 minutes.

The biphasic solution was separated and the organic layer was washed with water (16 L). The organic solution was reduced to a concentrate volume of 30 to 34 L via atmospheric distillation and cooled to 45° C. to 50° C.

Heptanes (54 kg) was charged to the reactor and the solution was reduced to a concentrate volume of 69 to 73 L via atmospheric distillation. The solution was cooled to 30° C. to 35° C. The reaction mixture was verified for residual tetrahydrofuran and water content. Reaction was seeded with crystals of the product and the mixture was cooled to 0° C. to 5° C. over a minimum of 1 hour and maintained for a minimum of 3 hours.

The solid product was isolated via filtration, washed with cold heptanes (2×10 kg) and dried. The product was sampled for dryness and packaged. The packaged product (Compound 2) was sampled, tested: HPLC purity not less than 97% a/a and released prior to use in the next step.

Purification of cis-(±)-1,3-dimethyl-4-[3-(1-methylethoxy)phenyl]-4-piperidinol (Compound 2)

Synthesis of carbonic acid, ethyl (3S,4R)-1,3-dimethyl-4-[3-(1-methylethoxy) phenyl]-4-piperidinyl ester compound with (+)-D-2,3-bwas[(4-methylbenzoyl) oxy]butanedioic acid (1:1) (Compound 3)

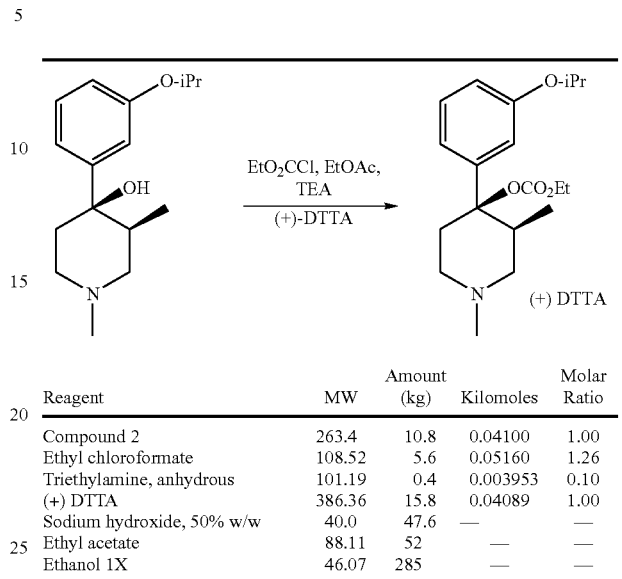

| Reagent | MW | Amount (kg) | Kilomoles | Molar Ratio |
|---|---|---|---|---|
| Compound 2 | 263.4 | 10.8 | 0.04100 | 1.00 |
| Ethyl chloroformate | 108.52 | 5.6 | 0.05160 | 1.26 |
| Triethylamine, anhydrous | 101.19 | 0.4 | 0.003953 | 0.10 |
| (+) DTTA | 386.36 | 15.8 | 0.04089 | 1.00 |
| Sodium hydroxide, 50% w/w | 40.0 | 47.6 | — | — |
| Ethyl acetate | 88.11 | 52 | — | — |
| Ethanol 1X | 46.07 | 285 | — | — |

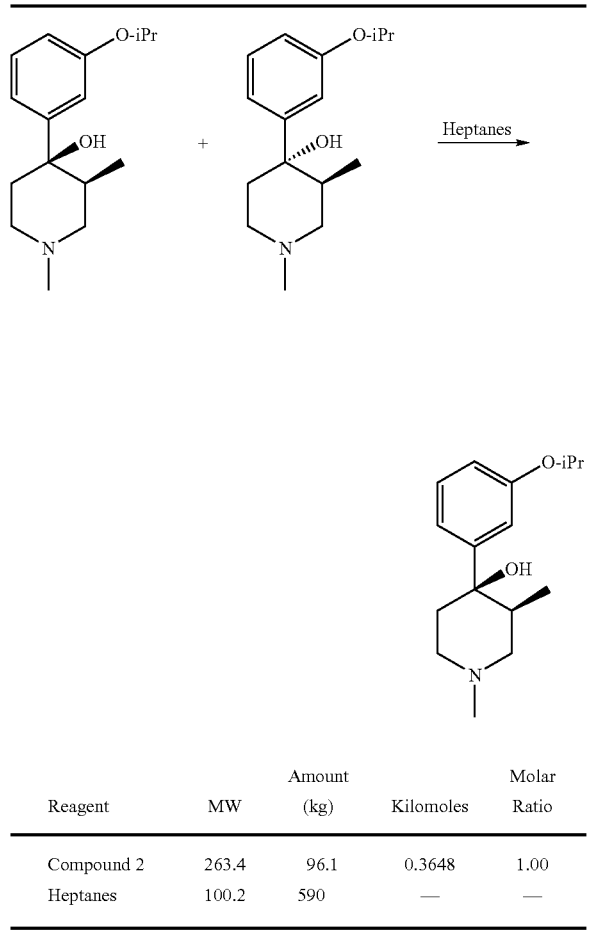

| Reagent | MW | Amount (kg) | Kilomoles | Molar Ratio |
|---|---|---|---|---|
| Compound 2 | 263.4 | 96.1 | 0.3648 | 1.00 |
| Heptanes | 100.2 | 590 | — | — |

A reactor was charged with compound 2 (96.1 kg) and heptanes (328 L). The mixture was heated to 55 to 60° C. and maintained for a minimum of 1 hour. The mixture was verified to ensure that all of the solids have dissolved The solution was cooled to 30 to 35° C. over a minimum of 1 hour and maintained for a minimum of 1 hour. The mixture was verified to ensure that precipitation has occurred. The mixture was cooled to 0° C. to 5° C. over a minimum of two hours and maintained for a minimum of 4 hours.

The solid purified compound 2 was isolated via filtration, washed with cold heptanes (2×131 kg) and dried. The product was sampled for dryness and packaged. The packaged product was sampled, tested for HPLC purity, not less than 97% a/a and released prior to use in the next step.

A reactor was charged with compound 2 (10.8 kg) and ethyl acetate (48 kg). The mixture was maintained at 20° C. to 25° C. for a minimum of 30 minutes until all of the solids have dissolved. The solution was cooled to 0° C. to 5° C.

Triethylamine (0.4 kg) was charged to the reactor and the transfer equipment was rinsed forward with ethyl acetate (1 kg).

Ethyl chloroformate (5.6 kg) was charged to the reactor while maintaining a temperature of 0° C. to 15° C. The transfer equipment was rinsed forward with ethyl acetate (3 kg). The mixture was maintained at 20° C. to 25° C. for a minimum of 3 hours.

Sodium hydroxide, 50% (7.6 kg) was charged to the reactor while maintaining a temperature of 0° C. to 38° C. The transfer equipment was rinsed forward with water (17 L). The solution was maintained at 20° C. to 25° C. for a minimum of 20 minutes and the pH of the solution was checked to ensure it was above 10.

The biphasic solution was separated and the organic layer was washed twice with water (22 L). The organic solution was dried via azeotropic distillation, and then reduced to a concentrate volume of 20 to 24 L via atmospheric distillation. The solution was cooled to 40° C. to 50° C.

Ethanol 1× (60 kg) was charged to the reactor. The solution was reduced to a concentrate volume of 30 to 34 L via atmospheric distillation and cooled to 55° C. to 60° C.

A glass-lined reactor was charged with (+)-di-p-toluoyl-D-tartaric acid (15.8 kg) and ethanol 1× (51 kg). With moderate agitation, the temperature was adjusted to 60° C. to 65° C.

The reaction mixture was transferred into the acid solution while maintaining a temperature of 60° C. to 70° C. The transfer equipment was rinsed forward with ethanol 1× (17 kg). The solution was maintained at 60° C. to 65° C. for a period of 1 to 1.5 hours. The suspension was cooled to 50° C. to 55° C. and maintained for a period of 2 to 2.5 hours. The suspension was cooled to 20° C. to 25° C. over a minimum of 3 hours and maintained for a minimum of 10 hours.

The solid was isolated by filtration, washed with ethanol 1× (17 kg), dried and packaged. The packaged crude product was sampled and tested for chiral purity of compound 3.

A reactor was charged with the crude product and ethanol 1× (as per calculation). The mixture was adjusted to 60° C. to 65° C. and maintained for a period of 2 to 2.5 hours. The suspension was cooled to 20° C. to 25° C. over a minimum of 2 hours. The suspension was cooled to 0° C. to 5° C. and maintained for a minimum of 3 hours.

The solid compound 3 was isolated via filtration, washed with cold ethanol 1× (17 kg), dried and packaged. The packaged product was sampled, tested, HPLC purity not less than 99.0% a/a; Chiral HPLC, not less than 99.5% and released prior to use in the next step.

Synthesis of (3R,4R)-3-(3,4-dimethyl-4-piperidinyl)phenol (Compound 4)

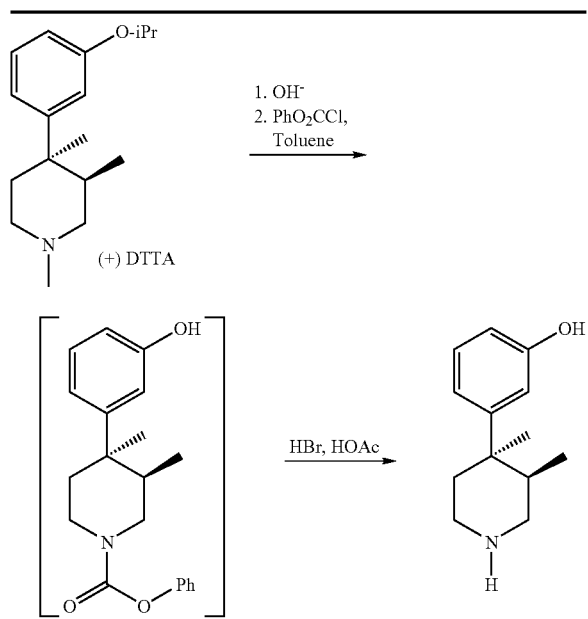

| Reagent | MW | Amount (kg) | Kilomoles | Molar Ratio |
| --- | --- | --- | --- | --- |
| Compound 3 | 647.8 | 18.3 | 0.02825 | 1.00 |
| Toluene | 92.14 | 50 | — | — |
| Water | 18.02 | 434 | — | — |
| Sodium hydroxide, 50% w/w | 40.0 | 110.7 | — | — |
| Phenyl chloroformate | 156.57 | 5.3 | 0.03385 | 1.20 |
| Hydrochloric acid, 31% | 36.46 | 2.8 | — | — |
| Acetic acid, glacial | 60.05 | 17.6 | 0.2931 | 10.38 |
| Hydrobromic acid | 80.92 | 19 | 0.1127 | 4.00 |
| t-Butyl methyl ether | 88.15 | 56 | — | — |
| Methanol | 32.04 | 8.7 | — | — |

A reactor was charged with compound 3 (18.3 kg), toluene (48 kg), and water (32 L). The mixture was adjusted to 20° C. to 25° C.

Sodium hydroxide, 50% (9.2 kg) was charged to the reactor while maintaining a temperature of 20° C. to 30° C. The transfer equipment was rinsed forward with water (4 L). With agitation, the mixture was cooled to 20° C. to 25° C. and maintained for 1 hour. The pH of the aqueous layer was checked to ensure that it was above 12.

The biphasic solution was separated and the organic layer was washed with a solution of water (14 L) and sodium hydroxide, 50% (0.7 kg). The organic layer was washed twice with water (15 L) and dried via azeotropic distillation. The solution was cooled to 80° C. to 85° C.

Phenyl chloroformate (5.3 kg) was charged to the reactor over a minimum of 1.5 hours while maintaining a temperature of 80° C. to 85° C. The transfer equipment was rinsed forward with toluene (2 kg). The solution was heated to reflux and maintained for a minimum of 3 hours, then cooled to 50° C. to 55° C. The mixture was maintained at reflux while awaiting the results.

The mixture was cooled to 20° C. to 25° C. and water (14 L) was charged to the reactor. Sodium hydroxide, 50% (2.3 kg) was charged to the reactor over a minimum of 1 hour while maintaining a temperature of 20° C. to 30° C. The transfer equipment was rinsed forward with water (4 L). The solution was maintained at 20° C. to 25° C. for a minimum of 1 hour.

The biphasic solution was separated and the organic layer was washed with a solution of water (15 L) and hydrochloric acid, 31% (1.9 kg). The organic solution was reduced to a concentrate volume of 23 to 26 L via atmospheric distillation and cooled to 65° C. to 70° C.

Water (7 L) and acetic acid (13.6 kg) were charged to the reactor. The transfer equipment was rinsed forward with water (2 L). The solution was reduced to a concentrate volume of 26 to 29 L via atmospheric distillation and cooled to 50° C. to 60° C.

Hydrobromic acid (19 kg) was charged to the reactor, followed by acetic acid (4 kg). The solution was heated to reflux and maintained for a minimum of 18 hours. The solution was cooled to 55° C. to 60° C. The solution was cooled to 10° C. to 15° C.

Sodium hydroxide, 50% (6 kg) was charged to the reactor over a minimum of 1 hour while maintaining a temperature of 10° C. to 30° C. The transfer equipment was rinsed forward with water (5 L). The temperature was adjusted to 20° C. to 25° C. and the pH was checked to ensure it was less than 1.7.

To the reactor, t-butyl methyl ether (16 kg) was charged while maintaining a temperature of 20° C. to 25° C. Water (27 L) was charged to the reactor and the solution was maintained at 20° C. to 25° C. for a minimum of 30 minutes.

The biphasic solution was separated and the aqueous solution was transferred to a reactor. The organic solution was transferred to a 200 L glass receiver. The aqueous solution was washed twice with t-butyl methyl ether (16 kg).

The organic layers were transferred from the glass receiver to a reactor. Water (5 L) was charged to the reactor, followed by hydrochloric acid, 31% (0.9 kg) while maintaining a temperature of 20° C. to 25° C. The transfer equipment was rinsed forward with water (2 L). The biphasic solution was maintained at 20° C. to 25° C. for a minimum of 20 minutes.

The biphasic solution was separated and the aqueous solution was washed twice with t-butyl methyl ether (4 kg).

The acidic solution from the new polyethylene drum was transferred to the 200 L reactor. The transfer equipment was rinsed forward with water (2 L).

Methanol (8.7 kg) was charged to the reactor over a minimum of 30 minutes while maintaining a temperature of 20° C. to 25° C.

A portable agitation stainless steel tank was charged with water (41 L) and sodium hydroxide, 50% (12.5 kg). The transfer equipment was rinsed forward with water (4 L). The solution was transferred to the reactor to achieve a pH of 10.0 to 10.5 while maintaining a temperature of 20° C. to 35° C.

The suspension was cooled to 0° C. to 5° C. and maintained for a minimum of 4 hours.

The compound 4 was isolated via filtration, washed with cold water (2×9 L), dried, and packaged. The packaged product was sampled, tested: HPLC Purity, not less than 98.5% a/a; Chiral Purity, not less than 99.0% and HPLC Assay, not less than 95% w/w and released prior to use in the next step.

Synthesis of methyl (αS, 3R, 4R)-4-(3-hydroxyphenyl)-3,4-dimethyl-α-(phenylmethyl)-1-piperidinepropanoate hydrochloride (Compound 6)

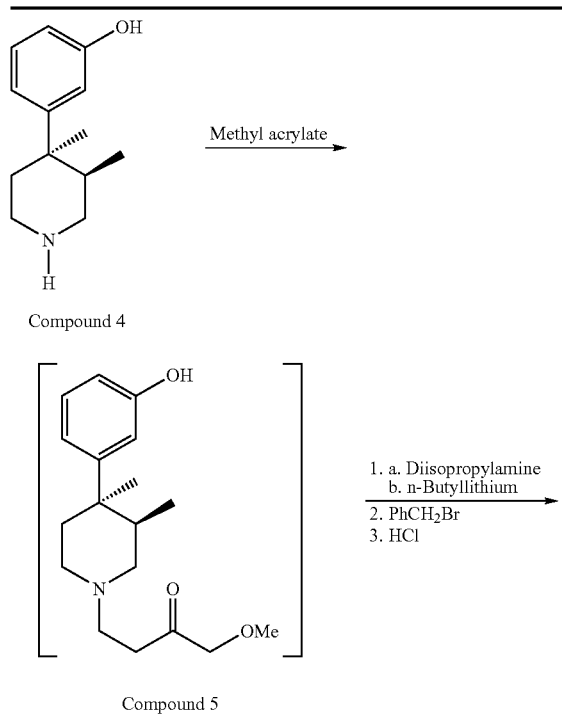

| Reagent | MW | Amount (kg) | Kilomoles | Molar Ratio |
|---|---|---|---|---|
| Compound 4 | 205.3 | 19.2 | 0.09352 | 1.00 |
| Methyl acrylate | 86.09 | 8.5 | 0.09875 | 1.05 |
| Tetrahydrofuran | 72.11 | 692 | — | — |
| n-Butyllithium | 64.06 | 87.4 | 0.2056 | 2.20 |
| Diisopropylamine | 101.19 | 21.8 | 0.2154 | 2.30 |
| Benzyl bromide | 171.04 | 32.0 | 0.1871 | 2.00 |
| Heptanes | 100.21 | 209 | — | — |
| Methanol | 32.04 | 659 | — | — |
| Hydrochloric acid, 31% | 36.46 | 36.2 | 0.3078 | 3.29 |
| Sodium hydroxide, 50% w/w | 40.0 | 4.9 | 0.06125 | 0.65 |
| Hydrogen chloride gas | 36.46 | 14.4 | 0.3950 | 4.23 |
| Hyflo supercel | — | 1.9 | — | — |
| Water | 18.02 | 566 | — | — |

A reactor was charged with compound 4 (19.2 kg) and tetrahydrofuran (222 kg). The mixture was heated to 40° C. to 45° C. with 50% agitation.

Methyl acrylate (8.5 kg) was charged to the reactor over a minimum of 30 minutes while maintaining a temperature of 40° C. to 45° C. The transfer equipment was rinsed forward with THF (17 kg). The reaction mixture was maintained at 40° C. to 45° C. for a period of 18 to 19 hours. The reaction mixture was cooled to 20° C. to 25° C.

A portable agitation stainless steel tank was charged with hyflo supercel (1.9 kg) and heptanes (13 kg). The mixture was agitated for a minimum of five minutes. The mixture was transferred to the reactor and rinsed forward with heptanes (5 kg). The mixture was maintained at 20° C. to 25° C. for a minimum of 20 minutes.

The mixture was filtered into a reactor for clarification, rinsed forward with heptanes (26 kg) and cooled to −5° C. to 0° C. The solution was reduced to a concentrate volume of 29 to 48 L via vacuum distillation to give a solution of compound 5.

Heptanes (26 kg) was charged to the reactor at 30° C. or less. The solution was cooled to −5° C. to 0° C. and reduced to a concentrate volume of 29 to 48 L via vacuum distillation.

Tetrahydrofuran (333 kg) was charged to the reactor, followed by diisopropylamine (21.8 kg). The transfer equipment was rinsed forward with tetrahydrofuran (12 kg). The solution was cooled to −15 to −10° C.

The reactor was charged with n-butyllithium in hexanes (87.4 kg) over a minimum of 1 hour while maintaining a temperature of −15° C. to −5° C. The transfer equipment was rinsed forward with THF (2×5 kg). The solution was maintained at −10° C. to −5° C. for a period of 1 to 3 hours, then cooled to −25° C. to −20° C.

The acrylate solution in the reactor was transferred to this reactor while maintaining a temperature of −25 to −15° C. The transfer equipment was rinsed forward with THF (8 kg). The suspension was maintained at −25 to −20° C. for a period of 30 to 60 minutes.

Benzyl bromide (32.0 kg) was charged to the reactor over a minimum of 2 hours while maintaining a temperature of −25 to −20° C. The transfer equipment was rinsed forward with THF (8 kg). The mixture was maintained at −25 to −20° C. for a minimum of 16 hours.

A portable storage tank was charged with water (61 L) and hydrochloric acid, 31% (18.1 kg), and then agitated for a minimum of two minutes to form a solution. A second portable storage tank was charged with water (61 L) and hydrochloric acid, 31% (18.1 kg), and then agitated for a minimum of two minutes to form a solution. Both acid solutions were transferred to the reactor over a minimum of two hours while maintaining a temperature of −25 to −15° C. The solution was warmed to 20 to 25° C. over a minimum of three hours.

A portable storage tank was charged with water (29 L) and sodium hydroxide, 50% (4.9 kg). The transfer equipment was rinsed forward with water (15 L) and the mixture was agitated for a minimum of two minutes to form a solution.

The basic solution (29 kg) was transferred to the reactor while maintaining a temperature of 20 to 25° C. until a pH of 9.0 to 9.5 was obtained. The biphasic solution was separated and the aqueous solution was transferred to the 600 L reactor.

The aqueous solution was washed with heptanes (26 kg). The resulting organic solution was transferred to the 1500 L reactor and the transfer equipment was rinsed forward with heptanes (17 kg). The solution was cooled to −30 to −20° C.

A reactor was charged with methanol (113 kg) and cooled to −30 to −20° C. Hydrogen chloride gas (14.4 kg) was charged to the reactor while maintaining a temperature of −30 to −10° C.

The acid solution was charged to above reactor while maintaining a temperature of −30 to −5° C. The transfer equipment was rinsed forward with methanol (19 kg). The solution temperature was adjusted to −10 to −5° C. The solution was reduced to a concentrate volume of 168 to 216 L via vacuum distillation.

The solution was transferred to the 600 L reactor and rinsed forward with methanol (48 kg). The solution was cooled to −10 to −5° C. and reduced to a concentrate volume of 48 to 68 L via vacuum distillation.

Methanol (77 kg) was charged to the 1500 L reactor and rinsed into the reactor. The solution was then cooled to −10 to −5° C. and reduced to a concentrate volume of 48 to 68 L via vacuum distillation.

Methanol (106 kg) was charged to the reactor at a temperature of 30° C. or less, and then heated to 40 to 45° C. The solution was maintained at 40 to 45° C. for a period of 1 to 2 hours. The solution was cooled to 20 to 25° C. over a minimum of 3 hours and maintained in the range for a minimum of 1 hour. The solution was cooled to 2 to 7° C. over a minimum of 1 hour and maintained in the range for a minimum of 1 hour.

The crude product, compound 6, was isolated by filtration, washed with cold methanol (2×15 kg), and tested for purity. The filtrate was kept for further processing.

A reactor was charged with the wet filter cake and methanol (60 kg). The mixture was heated to reflux and maintained at reflux for a period of 1 to 2 hours. The solution was cooled to 2 to 7° C. over a minimum of 4 hours and maintained in the range for a minimum of 1 hour.

The crude product was isolated by filtration, washed with cold methanol (2×15 kg), and tested for purity. The filtrate was kept for further processing.

The reactor was charged with the wet filter cake and methanol (60 kg). The mixture was heated to reflux and maintained at reflux for a minimum of 1 hour. The solution was cooled to 2 to 7° C. over a minimum of 4 hours and maintained in the range for a minimum of 1 hour.

The crude product was isolated by filtration, washed with cold methanol (2×15 kg), and tested for purity and chiral HPLC The reactor was charged with the wet filter cake and methanol (60 kg). The mixture was heated to reflux and maintained at reflux for a minimum of 1 hour. The solution was cooled to 2 to 7° C. over a minimum of 4 hours and maintained in the range for a minimum of 1 hour.

The product compound 6 was isolated by filtration, washed with cold methanol (2×15 kg), sampled for HPLC purity, Chiral HPLC, and isomers and packaged. The packaged product was sampled, tested: HPLC purity; >99.0% a/a and Chiral HPLC, 3.0% and released before use in the next step.

Synthesis of (αS, 3R, 4R)-4-(3-hydroxyphenyl)-3,4-dimethyl-α-(phenylmethyl)-1-piperidinepropanoic acid monohydrate (Compound 7)

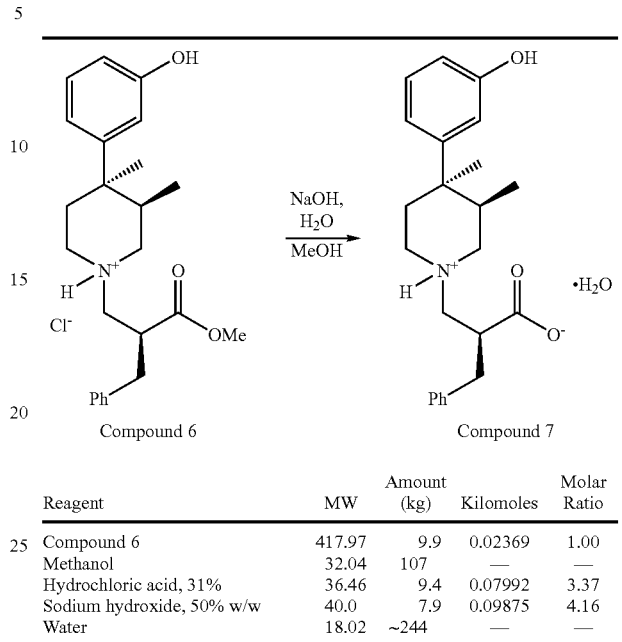

| Reagent | MW | Amount (kg) | Kilomoles | Molar Ratio |
|---|---|---|---|---|
| Compound 6 | 417.97 | 9.9 | 0.02369 | 1.00 |
| Methanol | 32.04 | 107 | — | — |
| Hydrochloric acid, 31% | 36.46 | 9.4 | 0.07992 | 3.37 |
| Sodium hydroxide, 50% w/w | 40.0 | 7.9 | 0.09875 | 4.16 |
| Water | 18.02 | ~244 | — | — |

A reactor was charged with compound 6 (9.9 kg) and water (74 L). The mixture was adjusted to 20 to 25° C.

Sodium hydroxide, 50% (7.9 kg) was charged to the reactor over a minimum of 10 minutes. The transfer equipment was rinsed forward with water (10 L). The pH of the mixture was checked to ensure it was above 12.

The solution was maintained and agitated at a temperature of 20 to 25° C. for a minimum of 4 hours. The reaction mixture was then filtered into a reactor for clarification. The product was rinsed forward with water (8 L).

Methanol (84 kg) was charged to the reactor and adjusted to 20 to 25° C.

Hydrochloric acid, 31% (6.9 kg) was charged to the reactor in portions until a pH of 9.0 to 10.0 was reached.

A new PE drum was charged with water (7.6 L) and hydrochloric acid, 31% (2.5 kg). The transfer equipment was rinsed forward with water (4.0 L) and the solution was agitated for a minimum of two minutes to mix.

A beaker was charged with methanol (0.4 kg), water (0.5 L), and Compound 7 (100 g). The mixture was charged to the reactor and rinsed forward with a solution of water (0.3 L) and methanol (0.2 kg) to seed the reaction mixture.

The pH of the reaction mixture was adjusted with the prepared acidic solution (10.4 kg) until a pH of 5.8 to 6.2 was obtained. The mixture was maintained at 20 to 25° C. for a minimum of 1 hour and verified to ensure crystallization has occurred. The suspension was cooled to 0 to 5° C. and reduced to a concentrate volume of 107 to 124 L via vacuum distillation. The suspension was adjusted to 20 to 25° C. and the pH was checked to ensure it was between 5.8 and 6.2.

The suspension was cooled to 2 to 7° C. and agitated for a minimum of 4 hours.

The product was isolated by filtration, washed with cold water (2×30 L), dried, sampled for water content and packaged. The packaged product was sampled, tested: HPLC purity, 98.% a/a, Chiral HPLC, 98%, and HPLC assay, 98.0% w/w and released prior to use in the next step.

Synthesis of [[2(S)-[[4(R)-(3-hydroxyphenyl)-3(R),4-dimethyl-1-piperidinyl]methyl]-1-oxo-3-phenylpropyl]amino]acetic acid dihydrate (Alvimopan)

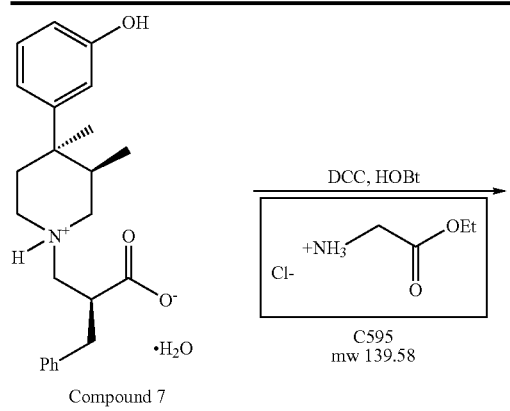

Compound 7

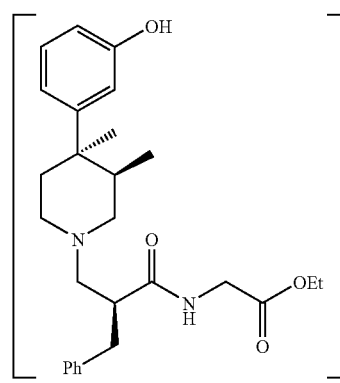

Compound 8

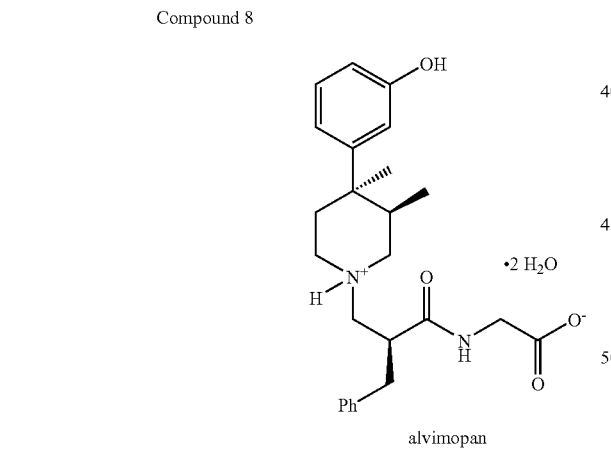

alvimopan

| Reagent | MW | Amount (kg) | Kilomoles | Molar Ratio |
|---|---|---|---|---|
| Compound 7 | 385.5 | 17.9 | 2.02049 | 1.00 |
| Glycine ethyl ester hydrochloride | 139.58 | 3.1 | 0.02254 | 1.10 |
| 1-Hydroxybenzotriazole hydrate | 135.13 | 3.5 | 0.02562 | 1.25 |
| Triethylamine | 101.2 | 2.3 | 0.02254 | 1.10 |
| 1,3-Dicyclohexylcarbodiimide | 206.33 | 4.7 | 0.02254 | 1.10 |
| Tetrahydrofuran | 72.11 | 156 | — | — |
| Ethyl acetate | 88.11 | 858 | — | — |
| Soda ash (Sodium carbonate) | 105.99 | 4.8 | — | — |
| Sodium bicarbonate | 84.00 | 3.1 | — | — |
| Brine | — | 112 | — | — |

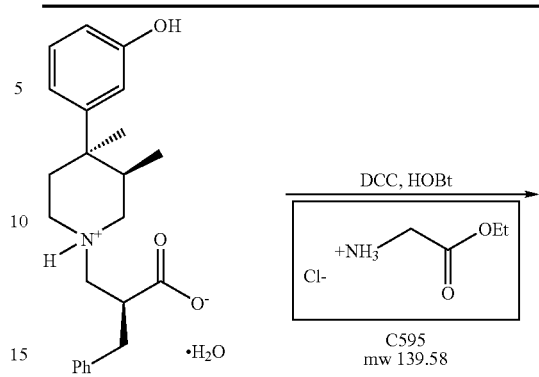

Compound 7

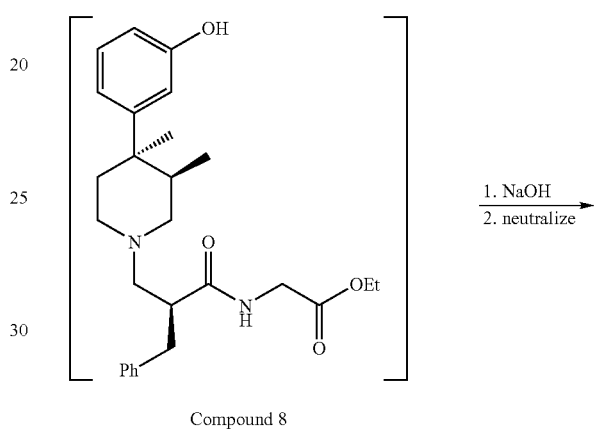

Compound 8

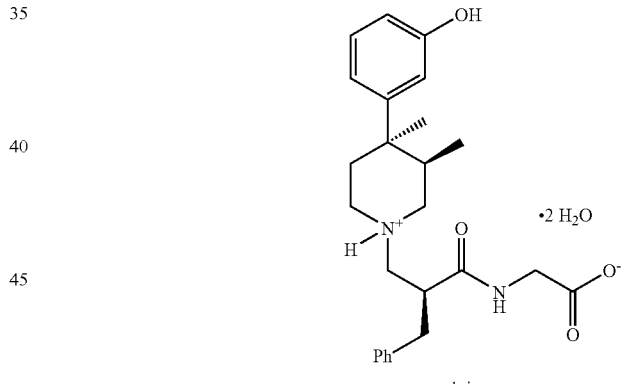

alvimopan

| Reagent | MW | Amount (kg) | Kilomoles | Molar Ratio |
|---|---|---|---|---|
| Ethanol 1X | 46.07 | 743 | — | — |
| Purified water | 18.02 | 1196 | — | — |
| Sodium hydroxide, 50% w/w | 40.0 | 16.8 | — | — |
| Hydrochloric acid, 31% | 36.46 | 30.0 | — | — |

A portable agitation stainless steel tank (PAST) was charged with tetrahydrofuran (15 kg) and 1,3-dicyclohexylcarbodiimide (4.7 kg). The transfer equipment was rinsed forward with THF (16 kg).

A reactor was charged with compound 7 (7.9 kg), glycine ethyl ester hydrochloride (3.1 kg), 1-hydroxybenzotriazole hydrate (3.5 kg), tetrahydrofuran (99 kg) and purified water (3.3 kg). With 60% agitation, the mixture was adjusted to 20 to 25° C.

Triethylamine (2.3 kg) was charged to the reactor. The transfer equipment was rinsed forward with tetrahydrofuran (3 kg). The solution was maintained at 20 to 25° C. for a period of 20 to 60 minutes.

The 1,3-dicyclohexylcarbodiimide solution was transferred to the reactor while maintaining a temperature of 20 to 25° C. The transfer equipment was rinsed forward with tetrahydrofuran (23 kg).

The reaction mixture was maintained at 20 to 25° C. for a period of 36 to 38 hours with 100% agitation.

The reaction mixture was cooled to 0 to 5° C. The mixture was maintained in range for a period of 1 to 2 hours then filtered into another reactor. The reaction mixture was rinsed forward with ethyl acetate (20 kg). The mixture was cooled to 0 to 5° C. and reduced to a concentrate volume of 140 to 149 L via vacuum distillation.

Ethyl acetate (731 kg) was charged to the reactor and cooled to 0 to 5° C. The solution was reduced to a concentrate volume of 140 to 149 L via vacuum distillation. The mixture was verified for residual tetrahydrofuran.

A portable agitation stainless steel tank was charged with purified water (94 kg), soda ash (4.8 kg) and sodium bicarbonate (3.1 kg). The mixture was agitated for a minimum of two minutes until the solids dissolved.

The basic solution was charged to the reactor and the temperature was adjusted to 20 to 25° C. The agitation was maintained at 60% for a period of 20 to 60 minutes. The pH of the solution was checked to ensure it was between 9.5 and 10, and adjusted as necessary. The biphasic solution was separated and the organic solution was washed with brine (112 kg).

The reactor was charged with ethyl acetate (87 kg) and cooled to 0 to 5° C. The solution was reduced to a concentrate volume of 140 to 149 L via vacuum distillation, and cooled to −25 to −20° C. The temperature was maintained for a period of 10 to 11 hours.

The suspension was filtered into a reactor, rinsed forward with ethyl acetate (20 kg) and warmed to 0 to 5° C. The filtrate was reduced to a concentrate volume of 39 to 51 L via vacuum distillation.

Ethanol 1× (199 kg) was charged to the reactor and cooled to 0 to 5° C. The solution was reduced to a concentrate volume of 136 to 161 L via vacuum distillation. The reactor was charged with ethanol 1× (93 kg) and the mixture was verified for residual ethyl acetate.

A portable storage tank was charged with purified water (83 kg) and sodium hydroxide, 50% (5.6 kg). The transfer equipment was rinsed forward with purified water (19 kg). The mixture was agitated for a minimum of two minutes to form a solution. The basic solution was transferred to the reactor and maintained at 20 to 25° C. for a period of 1.5 to 3.5 hours. The suspension was filtered into a reactor and adjusted to 20 to 25° C. The 600 L reactor was rinsed forward with purified water (13 kg).

A portable storage tank was charged with purified water (15 kg) and hydrochloric acid, 31% (11.2 kg). The transfer equipment was rinsed forward with purified water (5 kg). The mixture was agitated for a minimum of two minutes to form a solution. The acidic solution was charged to the reactor in portions until a pH of 5.8 to 6.2 was achieved.

The crude product was isolated by filtration, washed with purified water (2×26 kg), washed with ethanol 1× (13 kg), dried and packaged.

The crude product was charged to a reactor with purified water (as per calculation).

A new PE pail was charged with purified water (1.9 kg) and sodium hydroxide, 50% (5.3 kg). The transfer equipment was rinsed forward with purified water (1.0 kg). The mixture was agitated for a minimum of two minutes to form a solution.

The reaction mixture was adjusted to a minimum pH of 13 using the basic solution (7.5 kg). The mixture was maintained at 20 to 25° C. for a period of 20 to 60 minutes.

The mixture was filtered for clarification into a reactor. The reactor was rinsed forward with purified water (10 kg) and was charged with ethanol 1× (as per calculation).

A portable storage tank was charged with purified water (14 kg) and hydrochloric acid, 31% (9.6 kg). The transfer equipment was rinsed forward with purified water (4 kg). The mixture was agitated for a minimum of two minutes to form a solution. The acidic solution was charged to the reactor in portions until a pH of 4.0 to 4.5 was obtained.

A new PE pail was charged with purified water (1.9 kg) and sodium hydroxide, 50% (0.3 kg). The transfer equipment was rinsed forward with purified water (1.0 kg). The mixture was agitated for a minimum of two minutes to form a solution. The basic solution was charged to the reactor in portions until a pH of 5.8 to 6.2 was obtained.

The mixture was verified for the presence of solids and the suspension was maintained at 20 to 25° C. for a minimum of 12 hours.

The product was isolated by filtration, washed first with purified water (as per calculation), next with ethanol 1× (as per calculation) and washed again with purified water (as per calculation). The filter cake was dried and packaged.

The crude product was charged to a reactor with purified water (as per calculation).

A new PE pail was charged with purified water (1.9 kg) and sodium hydroxide, 50kg). The transfer equipment was rinsed forward with purified water (1.0 kg). The mixture was agitated for a minimum of two minutes to form a solution. The basic solution was charged to the reactor in portions until a minimum pH of 13 was obtained.

The mixture was agitated at 20 to 25° C. for a period of 20 to 60 minutes. The mixture was filtered for clarification into another reactor. The reactor was rinsed forward with purified water (10 kg). The reactor was charged with ethanol 1× (as per calculation).

A portable storage tank was charged with purified water (13.5 kg) and hydrochloric acid, 31% (9.2 kg). The transfer equipment was rinsed forward with purified water (3.9 kg). The mixture was agitated for a minimum of two minutes to form a solution. The acidic solution was charged to the reactor in portions until a pH of 4.0 to 4.5 was obtained.

A new PE pail was charged with purified water (1.9 kg) and sodium hydroxide, 50% (0.3 kg). The transfer equipment was rinsed forward with purified water (1.0 kg). The mixture was agitated for a minimum of two minutes to form a solution. The basic solution was charged to the reactor in portions until a pH of 5.8 to 6.2 was obtained.

The mixture was verified for the presence of solids and the suspension was maintained at 20 to 25° C. for a minimum of 12 hours.

The product was isolated by filtration, washed first with purified water (as per calculation), next with ethanol 1× (as per calculation) and washed again with purified water (as per calculation). The filter cake was sampled for chloride, dried and packaged.

The dryer was charged with the over-dried product and purified water (2.0 kg), flushed with nitrogen and left at room temperature until the specified hydration level was achieved.

The hydrated product was then packaged and charged to a 50 L product blender. The product was blended for a period of twenty to thirty minutes and sampled for dryness. The product was blended for a further twenty to thirty minutes and resampled.

The alvimopan was then packaged, sampled, tested: HPLC purity, not less than 99.2% w/w; Chiral HPLC, not less than 99.0%; HPLC assay, 98.0 to 102.0%w/w and Residual solvents, not more than 1.2% w/w total and released.

Crystallization Techniques to Prepare Amorphous Solids a. Lyophilization

Solutions were prepared in 1,4-dioxane:t-butanol:water (1:1:1) solvent mixtures or water. The solutions were stirred at ambient conditions to dissolve the material(s). Once all the solids dissolved, the solutions were filtered through a 0.2 µm nylon filter into round bottom flasks. The flasks were submerged into liquid nitrogen and swirled to freeze the solution to the sides of the flasks. The samples were placed on a lyophilizer chilled to approximately −50° C. under vacuum. The samples were removed from the lyophilizer once all of the solvent was evaporated.

b. Rotary Evaporation

Solutions were prepared in ethanol ethanol:water, or 1,4-dioxane:water mixtures. The solutions were sonicated to assist in dissolution. Once the drug compound dissolved, the solutions were filtered through a 0.2 µm nylon filter into round bottom flasks. The flasks were placed on a rotoevaporator and submerged into a temperature bath set at approximately 30° C. The solvent was rapidly evaporated and the generated solids were collected.

Preparation of Amorphous [[2(S)-[[4(R)-(3-hydroxyphenyl)-3(R),4-dimethyl-piperidinyl]methyl]-1-oxo-3-phenylpropyl]amino]acetic acid Amorphous [[2(S)-[[4(R)-(3-hydroxyphenyl)-3(R),4-dimethyl-piperidinyl]methyl]-1-oxo-3-phenylpropyl]amino] acetic acid was prepared by dissolving the drug compound in ethanol at a concentration of approximately 3 mg/mL. The solution was filtered using a 0.2 µm nylon filter and rotary evaporated. Amorphous solids were also generated by dissolving alvimopan into 1,4-dioxane:t-butanol:water (1:1:1) solvent mixtures followed. by lyophilization. The solid materials were collected and placed into a vacuum oven heated at ambient, 60° C., or 100° C. for up to two days to remove any residual solvent. The resulting solids were collected and stored in a desiccator until time for analysis.

Amorphous [[2(S)-[[4(R)-(3-hydroxyphenyl)-3(R),4-dimethyl-piperidinyl]methyl]-1-oxo-3-phenylpropyl]amino] acetic acid sodium salt was prepared by dissolving alvimopan and the counter ion into ethanol or 1,4-dioxane:r-butanol:water (1:1:1) solvent mixtures with a counter ion: [[2(S)-[[4(R)-(3-hydroxyphenyl)-3(R),4-dimethyl-piperidinyl]methyl]-1-oxo-3-phenylpropyl]amino]acetic acid ratio of 1:1 or 2:1. The solutions were filtered using a 0.2 µm nylon filter and rotary evaporated or lyophilized. The solid material was collected and placed into a vacuum oven heated at ambient, 60° C., or 100° C. for up to two days to remove any residual solvent. The resulting solids were collected and stored in a desiccator until time for analysis.

Preparation of [[2(S)-[[4(R)-(3-Hydroxyphenyl))-3(R),4-dimethyl-piperidinyl]methyl]-1-oxo-3-phenylpropyl]amino] acetic Acid Solid Dispersions Solid dispersions of [[2(S)-[[4(R)-(3-hydroxyphenyl)-3 (R),4-dimethyl-piperidinyl]methyl]-1-oxo-3-phenylpropyl] amino]acetic acid with HPMC, mannitol, PVP, or PVP/VAc were prepared by dissolving the components in ethanol or 1,4-dioxane:t-butanol:water (1:1:1) solvent mixtures with a drug:excipient weight fraction of 70:30. The solutions were filtered using a 0.2 µm nylon filter and rotary evaporated or lyophilized. The solid material was collected and placed into a vacuum oven heated at ambient, 60° C., or 100° C. for up to two days to remove any residual solvent. The resulting solids were collected and stored in a desiccator until time for analysis.

Solid dispersions of amorphous [[2(S)-[[4(R)-(3-hydroxyphenyl)-3(R),4-dimethyl-piperidinyl]methyl]-1-oxo-3-phenylpropyl]amino]acetic acid sodium salt with the above mentioned excipients were also prepared with a drug:excipient weight fraction of 70:30. Some samples were prepared to contain a mannitol: [[2(S)-[[4(R)-(3-hydroxyphenyl)-3(R),4-dimethyl-piperidinyl]methyl]-1-oxo-3-phenylpropyl]amino] acetic acid molar ratio of 0.125:1, 0.25:1, and 0.5:1. The solids were dissolved in 1,4-dioxane:/butanol:water (1:1:1) solvent mixtures containing a counter ion: [[2(S)-[[4(R)-(3-hydroxyphenyl)-3(R),4-dimethyl-piperidinyl]methyl]-1-oxo-3-phenylpropyl]amino]acetic acid molar ratio of 1:1 or 2:1. The solutions were filtered using a 0.2 jam nylon filter and lyophilized. The solid material was collected and placed into a vacuum oven heated at ambient, 60° C., or 100° C. for up to two days to remove any residual solvent. The resulting solids were collected and stored in a desiccator until time for analysis.

Relative Humidity Stress Studies

Amorphous samples were exposed to ambient, 53%, and 97% relative humidities at ambient temperature (about 10° C. to about 30° C.). The samples were also exposed to 75% relative humidity at 40° C. The samples were stressed for up to 60 days. Samples were taken periodically throughout the study and analyzed by x-ray powder diffraction (XRPD) for presence of crystallinity.

Instrumental

Differential Scanning Calorimetry

Differential scanning calorimetry (DSC) was performed using a TA Instruments differential scanning calorimeter 2920. The sample was placed into an aluminum DSC pan, and the weight accurately recorded. The pan was covered with a lid and then crimped or left uncrimped. The sample cell was equilibrated at 25° C. and heated under a nitrogen purge at a rate of 10° C./min, up to a final temperature of 350° C. Indium metal was used as the calibration standard.

For studies of the glass transition temperature (Tg) of the amorphous material, the sample cell was equilibrated at 25° C., then heated under nitrogen at a rate of 20° C./min, up to 130° C. The sample cell was allowed to cool and equilibrate at 30° C. It was again heated at a rate of 20° C./min up to 130° C., and then cooled and equilibrated at 30° C. The sample cell was then heated at 20° C./min up to a final temperature of 350° C. The Tg is reported from the onset point of the transition.

Modulated Differential Scanning Calorimetry

Modulated differential scanning calorimetry (MDSC) data were obtained on a TA Instruments differential scanning calorimeter 2920 equipped with a refrigerated cooling system (RCS). The sample was placed into an aluminum DSC pan, and the weight accurately recorded. The pan was covered with a lid and crimped. MDSC data were obtained using a modulation amplitude of +/−0.8° C. and a 60 second period with an underlying heating rate of 2° C./min from −20 to 180° C. The temperature and the heat capacity were calibrated using indium metal and sapphire as the calibration standards, respectively.

Thermogravimetric Analysis

Thermogravimetric (TG) analyses were performed using a TA Instruments 2950 thermogravimetric analyzer. Each sample was placed in an aluminum sample pan and inserted into the TG furnace. The furnace was heated under nitrogen at a rate of 10° C./min, up to a final temperature of 350° C. Nickel and Alumel™ were used as the calibration standards.

Thermogravimetric Infrared Analysis

Thermogravimetric infrared (TG-IR) analyses were acquired on a TA Instruments thermogravimetric (TG) analyzer model 2050 interfaced to a Magna 560® Fourier transform infrared (FT-IR) spectrophotometer (Thermo Nicolet) equipped with a Ever-Glo mid/far IR source, a potassium bromide (KBr) beamsplitter, and a deuterated triglycine sulfate (DTGS) detector. The TG instrument was operated under a flow of helium at 90 and 10 cc/min for the purge and balance, respectively. Each sample was placed in a aluminum sample pan, inserted into the TG furnace, accurately weighed by the instrument, and the furnace was heated from ambient temperature to 150° C. at a rate of 20° C./min. The TG instrument was started first, immediately followed by the FT-IR instrument. Each IR spectrum represents 32 co-added scans collected at a spectral resolution of 4.0 cm$^{-1}$. IR spectra were collected every 15 seconds for 8 minutes. A background scan was collected before the beginning of the experiment. Wavelength calibration was performed using polystyrene. The TG calibration standards were nickel and Alumel™. Volatiles were identified from a search of the High Resolution Nicolet TGA Vapor Phase spectral library.

X-ray Powder Diffraction (Inel)

X-ray powder diffraction (XRPD) analyses were performed using an Inel XRG-3000 diffractometer equipped with a CPS (Curved Position Sensitive) detector with a 2θ range of 120°. Real time data were collected using Cu-Kα radiation starting at approximately 4° 2θ at a resolution of 0.03° 2θ. The tube voltage and amperage were set to 40 kV and 30 mA, respectively. The patterns are displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for approximately five minutes. Instrument calibration was performed using a silicon reference standard.

X-ray Powder Diffraction (Shimadzu)

X-ray powder diffraction (XRPD) analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.020 step) from 2.5 to 40° 2θ was used. A silicon standard was analyzed to check the instrument alignment. Data were collected and analyzed using XRD-6000 v. 4.1. Samples were prepared for analysis by placing them in an aluminum holder with silicon insert.

Results and Discussion

XRPD analysis indicated that the starting material was crystalline and was identified as [[2(S)-[[4(R)-(3-hydroxyphenyl)-3(R),4-dimethyl-piperidinyl]methyl]-1-oxo-3-phenyl propyl]amino]acetic acid dihydrate (alvimopan). Amorphous [[2(S)-[[4(R)-(3-hydroxyphenyl)-3(R),4-dimethyl-piperidinyl]methyl]-1-oxo-3-phenylpropyl]amino] acetic acid was prepared by two primary techniques:rotary evaporation and lyophilization. Generated amorphous samples are listed in Table 1. Characterization data of representative amorphous [[2(S)-[[4(R)-(3-hydroxyphenyl)-3(R), 4-dimethyl-piperidinyl]methyl]-1-oxo-3-phenylpropyl] amino]acetic acid samples prepared by rotary evaporation and lyophilization are listed in Table 2 through Table 4. Based on the thermal behavior of the amorphous materials and the selected excipients (Table 5), predicted glass transition temperatures (Tg) were obtained by fitting the Gordon-Taylor equation to the data (Table 6). The predicted values were obtained using a drug:excipient ratio of 70:30 for the calculations. Amorphous [[2(S)-[[4(R)-(3-hydroxyphenyl)-3(R), 4-dimethyl-piperidinyl]methyl]-1-oxo-3-phenyl propyl] amino]acetic acid solid dispersions were prepared using HPMC, mannitol, PVP, and PVP/VAc as the carrier excipients (Table 7). Characterization data of representative solid dispersions are listed in Table 8 through Table 11.

TABLE 1

Preparation of Amorphous [[2(S)-[[4(R)-(3-hydroxyphenyl)-3(R),4-dimethyl-piperidinyl]methyl]-1-oxo-3-phenylpropyl]amino]acetic acid

| Solvent[a] | Conditions[b] | Habit/Description |
|---|---|---|
| ethanol | roto evap at 40° C.; ambient vac oven | white flakes; not birefringent |
|  |  | white solids and flakes; not birefringent |
|  | sub sample of 1739-93-01; 100° C. vac oven | white solids; not birefringent |
|  | roto evap at 30° C.; 60° C. vac oven | white solids and flakes; not birefringent |
|  | sub sample of 1833-11-01; 100° C. vac oven | white solids and flakes; not birefringent |
|  |  | white solids; not birefringent |
|  | roto evap at 30° C.; 100° C. vac oven | white flakes; not birefringent |
|  |  | white solids and flakes; not birefringent |
| ethanol/water (1:1) | roto evap at ambient | — |
| 1,4-dioxane/t-BuOH/water, (1:1:1) | lyophilize; ambient vac oven | white fluffy solid; not birefringent |
|  | post SSCI LIMS No. 53134 TGA sample (File 91606) | — |
|  | lyophilize; 60° C. vac oven | white fluffy solid; not birefringent |
|  | lyophilize; 100° C. vac oven | white fluffy solid; not birefringent |

[a]t-BuOH = tert-butanol
[b]roto evap = Rotary evaporation; vac = vacuum
[c]IS = insufficient sample amount for analysis

TABLE 2

Characterization Data of Amorphous Alvimopan Prepared by Rotary Evaporation with 100° C. Vacuum Oven Heat Treatment

| Analytical Technique | Results[a] |
|---|---|
| XRPD | amorphous |
| DSC | endo at max temp 68° C. |
| | endo at max temp 138° C. |
| Cycling DSC | 1st heating: broad endo at max temp 141° C. |
| | 2nd heating: $T_g$ onset = 125° C., inflection = 128° C., offset = 129° C. |
| | 3rd heating: $T_g$ onset = 125° C., inflection = 128° C., offset = 129° C. |
| TGA | 0.5% weight loss between 25° C. and 200° C. |
| Karl Fisher | 0.98% water content |
| Moisture Sorption | 0.6% lost upon equilibration at 5% RH |
| | 13.8% weight gain between 5% and 95% RH |
| | 12.2% weight lost upon desorption |
| XRPD after Moisture Sorption | low crystalline; amorphous, Form A, or Form B |

[a]endo = endotherm; exo = exotherm; max = maximum; temp = temperature; $T_g$ = glass transition temperature; RH = relative humidity

TABLE 3

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid Prepared by Lyophilization with 100° C. Vacuum Oven Heat Treatment

| Analytical Technique | Results[a] |
|---|---|
| XRPD | amorphous |
| DSC | endo at max temp 72° C. |
| | endo at max temp 123° C. |
| Cycling DSC | 1st heating: broad endo at max temp 94° C., endo at max temp 125° C. |
| | 2nd heating: $T_g$ onset = 112° C., inflection = 117° C., offset = 117° C. |
| | 3rd heating: $T_g$ onset = 112° C., inflection = 117° C., offset = 117° C. |
| TGA | 0.5% weight loss between 25° C. and 200° C. |
| Moisture Sorption | 0.2% lost upon equilibration at 5% RH |
| | 13.0% weight gain between 5% and 95% RH |
| | 10.8% weight lost upon desorption |
| XRPD after Moisture Sorption | amorphous |

[a]endo = endotherm; exo = exotherm; max = maximum; temp = temperature; $T_g$ = glass transition temperature; RH = relative humidity

TABLE 4

Summary of Hot Stage Microscopy Data for Amorphous [[2(S)-[[4(R)-(3-hydroxy phenyl)-3(R),4-dimethyl-piperidinyl]methyl]-1-oxo-3-phenylpropyl]amino]acetic Acid

| Description[a] | Conditions | Observations |
|---|---|---|
| 1,4-dioxane/ t-BuOH/water, (1:1:1) lyophilize; ambient vac oven | 40x, crossed polars | 25.7° C. = sample isotropic (amorphous) |
| | | 50.9° C. = no change |
| | | 73.5° C. = no change |
| | | 99.8° C. = no change |
| | | 121.8° C. = sample begin flowing; isotropic sample remained isotropic upon cooling to ambient |

[a]t-BuOH = tert-butanol

TABLE 5

DSC Data of Excipients used to Prepare [[2(S)-[[4(R)-(3-hydroxyphenyl)-3(R),4-dimethyl-piperidinyl]methyl]-1-oxo-3-phenylpropyl]amino]acetic Acid Solid Dispersions

| Excipient[a] | DSC Results[b] |
|---|---|
| HPMC | endo at 52° C., 134° C., and 179° C. |
| | endo at 91° C., 188° C. |
| | $T_g$ onset = 155° C., inflection = 165° C., offset = 166° C. |
| Mannitol | endo at 167° C. |
| PVP | endo at 86° C., 185° C. |
| | endo at 101° C. |
| | $T_g$ onset = 179° C., inflection = 183° C., offset = 184° C. |
| PVP/VA$_c$ | endo at 86° C. |
| | endo at 96° C. |
| | $T_g$ onset = 108° C., inflection = 110° C., offset = 111° C. |

[a]HPMC = hydroxypropylmethyl cellulose; PVP = polyvinylpyrrolidone; PVP/VA$_c$ = poly(1-vinylpyrrolidone-co-vinyl acetate)
[b]endo = endotherm, $T_g$ = glass transition temperature

TABLE 6

Predicted Glass Transition Temperatures of [[2(S)-[[4(R)-(3-hydroxyphenyl)-3(R),4-dimethyl-piperidinyl]methyl]-1-oxo-3-phenylpropyl]amino]acetic Acid:Excipient (70:30) Solid Dispersion

| Excipient[a] | Average Molecular Weight (g/mol)[b,c] | Density (g/cm$^3$) | Glass Transition Temperature of Excipient (° C.)[c] | Experimental Glass Transition Temperature of Alvimopan:Excipient (70:30) Solid Dispersion (° C.)[d] | Predicted Glass Transition Temperature of Solid Dispersion (° C.)[e] |
|---|---|---|---|---|---|
| HPMC | 50,000 | 1.19 | 155 | 117 | 134 |
| Mannitol | 182 | 1.49 | 11[g] | 106 | 85 |
| PVP | 1,300,000 | 1.25 | 179 | 123 | 140 |
| PVP/VA$_c$ | 50,000 | 1.18 | 108 | 117 | 119 |

[a]HPMC = hydroxypropylmethyl cellulose; PVP = polyvinylpyrrolidone; PVP/VA$_c$ = poly(1-vinylpyrrolidone-co-vinyl acetate)
[b]Molecular weights obtained from supplier. Rounded to the nearest whole number.
[c]Glass transition temperatures are experimental values and are reported at the onset. Temperatures rounded to the nearest degree.
[d]Values obtained from DSC studies. Temperatures are onset values and rounded to the nearest degree.
[e]Predicted values determined based on Gordon-Taylor equation. Used amorphous alvimopan experimentally determined glass transition temperature for the analysis. Calculations based on a 0.7 weight fraction of alvimopan and 0.3 weight fraction of excipient. Temperatures rounded to the nearest degree.

TABLE 7

Preparation of [[2(S)-[[4(R)-(3-hydroxyphenyl)-3(R),4-dimethyl-piperidinyl]methyl]-1-oxo-3-phenylpropyl]amino]acetic Acid Solid Dispersions

| Excipient[a] (wt fraction) | Conditions[b] | Description | XRPD Result |
|---|---|---|---|
| HPMC (0.3) | lyophilized; 1,4-dioxane/t-BuOH/water, (1:1:1); 100° C. vac oven | fluffy white solids; not birefringent | amorphous |
|  | ethanol roto evap | clear film and white flakes; not birefringent | Form B; poorly crystalline |
| Mannitol (0.3) | roto evap at 30° C.; ethanol; 100° C. vac oven | — | Form B Alvimopan + Form II Mannitol |
|  | lyophilized; 1,4-dioxane/t-BuOH/water, (1:1:1); 100° C. vac oven | off-white solid; not birefringent | Form I and II Mannitol |
|  | sub-sample of 1833-39-01; before vac oven drying | — | Form I and II Mannitol |
| PVP (0.3) | roto evap at 30° C.; ethanol; 60° C. vac oven | clear film | amorphous |
|  | lyophilized; 1,4-dioxane/t-BuOH/water, (1:1:1); 100° C. vac oven | white solid; not birefringent | amorphous |
|  | sub-sample of 1833-39-02; before vac oven drying | — | amorphous |
|  | roto evap at 30° C.; ethanol; 100° C. vac oven | white solids and flakes; not birefringent | amorphous |
| PVP/VA$_c$ (0.3) | roto evap at 30° C.; ethanol; 100° C. vac oven | off-white solids and flakes; not birefringent | amorphous |

[a]HPMC = hydroxypropylmethyl cellulose; PVP = polyvinylpyrrolidone; PVP/VA$_c$ = poly(1-vinylpyrrolidone-co-vinyl acetate)
[b]roto evap = Rotary evaporation; vac = vacuum; t-BuOH = tert-butanol

TABLE 8

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid:HPMC (70:30) Solid Dispersion Prepared by Lyophilization with 100° C. Vacuum Oven Heat Treatment

| Analytical Technique | Results[a] |
|---|---|
| XRPD | amorphous |
| DSC | endo at max temp 72° C. |
|  | endo at max temp 126° C. |
| Cycling DSC | 1$^{st}$ heating: broad endo at max temp 79° C., endo at max temp 127° C. |
|  | 2$^{nd}$ heating: T$_g$ onset = 115° C., inflection = 120° C., offset = 120° C. |
|  | 3$^{rd}$ heating: T$_g$ onset = 117° C., inflection = 121° C., offset = 121° C. |
| TGA | 0.5% weight loss between 25° C. and 200° C. |
| Moisture Sorption | 0.8% lost upon equilibration at 5% RH |
|  | 22.2% weight gain between 5% and 95% RH |
|  | 20.5% weight lost upon desorption |
| XRPD after Moisture Sorption | amorphous |

[a]endo = endotherm; exo = exotherm; max = maximum; temp = temperature; T$_g$ = glass transition temperature; RH = relative humidity

TABLE 9

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid:Mannitol (70:30) Mixture Prepared by Lyophilization with 100° C. Vacuum Oven Heat Treatment

| Analytical Technique | Results[a] |
|---|---|
| XRPD | poorly crystalline: Forms II and III of Mannitol |
| DSC | endo at max temp = 150° C. |
|  | endo at onset 161° C. and max 165° C. |
|  | endo at onset 293° C. and max 294° C. |
| Cycling DSC | 1$^{st}$ heating: broad endo at max temp 88 |
|  | 2$^{nd}$ heating: T$_g$ onset = 106° C., inflection = 110° C., offset = 112° C. |
|  | 3$^{rd}$ heating: T$_g$ onset = 106° C., inflection = 112° C., offset = 112, endo at max temp 152° C., endo at max temp 165° C. |
| TGA | 0.7% weight loss between 25° C. and 190° C. |
| Moisture Sorption | 0.2% lost upon equilibration at 5% RH |
|  | 13.0% weight gain between 5% and 95% RH |
|  | 11.7% weight lost upon desorption |
| XRPD after Moisture Sorption | poorly crystalline: Forms II and III of Mannitol |

[a]endo = endotherm; exo = exotherm; max = maximum; temp = temperature; T$_g$ = glass transition temperature; RH = relative humidity

TABLE 10

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid:PVP (70:30) Solid Dispersion Prepared by Ethanol Rotary Evaporation with 100° C. Vacuum Oven Heat Treatment

| Analytical Technique | Results[a] |
|---|---|
| XRPD | amorphous |
| DSC | endo at max temp 136° C. |
| Cycling DSC | 1$^{st}$ heating: endo at max temp 138° C. |
|  | 2$^{nd}$ heating: T$_g$ onset = 123° C., inflection = 128° C., offset = 128° C. |
|  | 3$^{rd}$ heating: T$_g$ onset = 122° C., inflection = 128° C., offset = 128° C. |

TABLE 10-continued

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid:PVP (70:30) Solid Dispersion Prepared by Ethanol Rotary Evaporation with 100° C. Vacuum Oven Heat Treatment

| Analytical Technique | Results[a] |
|---|---|
| TGA | 0.5% weight loss between 25° C. and 200° C. |
| Moisture Sorption | 0.4% lost upon equilibration at 5% RH |
| | 30.4% weight gain between 5% and 95% RH |
| | 28.0% weight lost upon desorption |
| XRPD after Moisture Sorption | amorphous |

[a]endo = endotherm; exo = exotherm; max = maximum; temp = temperature; $T_g$ = glass transition temperature; RH = relative humidity

TABLE 11

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid:PVP/VA$_c$ (70:30) Solid Dispersion Prepared by Ethanol Rotary Evaporation with 100° C. Vacuum Oven Heat Treatment

| Analytical Technique | Results[a] |
|---|---|
| XRPD | amorphous |
| DSC | endo at max temp 125° C. |
| Cycling DSC | 1$^{st}$ heating: endo at max temp 128° C. |
| | 2$^{nd}$ heating: $T_g$ onset = 117° C., |
| | inflection = 121° C., offset = 121° C. |

TABLE 11-continued

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid:PVP/VA$_c$ (70:30) Solid Dispersion Prepared by Ethanol Rotary Evaporation with 100° C. Vacuum Oven Heat Treatment

| Analytical Technique | Results[a] |
|---|---|
| | 3$^{rd}$ heating: $T_g$ onset = 117° C., |
| | inflection = 121° C., offset = 121° C. |
| TGA | 0.2% weight loss between 25° C. and 200° C. |
| Moisture Sorption | 0.2% lost upon equilibration at 5% RH |
| | 23.4% weight gain between 5% and 95% RH |
| | 21.5% weight lost upon desorption |
| XRPD after Moisture Sorption | amorphous |

[a]endo = endotherm; exo = exotherm; max = maximum; temp = temperature; $T_g$ = glass transition temperature; RH = relative humidity The amorphous sodium salt of [[2(S)-[[4(R)-(3-hydroxyphenyl)-3(R),4-dimethyl-piperidinyl]methyl]-1-oxo-3-phenylpropyl]amino]acetic acid was also prepared (Table 12). A crystalline sodium salt was not obtained. Characterization data indicate that a 1:1 and 2:1 (sodium: [[2(S)-[[4(R)-(3-hydroxyphenyl)-3(R),4-dimethyl-piperidinyl]methyl]-1-oxo-3-phenylpropyl]amino]acetic acid) amorphous salts were prepared (Table 13, Table 14). Limited studies were conducted to prepare solid dispersions of amorphous [[2(S)-[[4(R)-(3-hydroxyphenyl)-3(R),4-dimethyl-piperidinyl]methyl]-1-oxo-3-phenylpropyl]amino]acetic acid sodium salt with HPMC, mannitol, PVP, and PVP/VAc. Characterization data of those materials are listed in Table 15 through Table 20.

TABLE 12

Preparation of [[2(S)-[[4(R)-(3-hydroxyphenyl)-3(R),4-dimethyl-piperidinyl]methyl]-1-oxo-3-phenylpropyl]amino]acetic Acid Sodium

| Counter Ion (theoretical counter ion: alvimopan) | Solvent | Condition[a] | Observation | XRPD Result[b] |
|---|---|---|---|---|
| sodium acetate (1:1) | ethanol | FE | small needle clusters; birefringent | Form A |
| sodium carbonate, (2:1) | ethanol | solvent addition; slurry | hazy solution | IS |
| | ethanol; counter ion dissolved in water | AS/S | white precipitate | IS |
| | water | slurry | — | Form B |
| | water | filtered solution of 1833-13-05; centrivap | off-white solid | poorly crystalline |
| | 1:1 dioxane:water | roto evap; dried in 100° C. vac oven | white solids and film; not birefringent | amorphous + peak |
| | 1:1:1 dioxane:t-BuOH:water | lyophilized; dried in 100° C. vac oven | white fluffy solids; not birefringent | amorphous |
| | 1:1 dioxane:water | roto evap; dried in 100° C. vac oven | off white solids; not birefringent | amorphous + Na$_2$CO$_3$ peaks |
| | 1:1:1 dioxane:t-BuOH:water | lyophilized; dried in 100° C. vac oven | white fluffy solids; not birefringent | amorphous |
| sodium hydroxide, (1:1) | ethanol | FE | clear film and white solids | amorphous |
| | ethanol | centrivap | white solids; no birefringence | amorphous |
| | ethanol | SE | clear film; not birefringent | — |
| | ethanol | vapor diffusion; ethyl acetate | no solids | — |
| | ethanol | roto evap; dried in 80° C. oven | white solids and flakes; not birefringent | amorphous + peak |
| | 1:1:1 dioxane:t-BuOH:water | lyophilized; dried in 100° C. vac oven | white fluffy solids; not birefringent | amorphous + peak |

TABLE 12-continued

Preparation of [[2(S)-[[4(R)-(3-hydroxyphenyl)-3(R),4-dimethyl-piperidinyl]methyl]-1-oxo-3-phenylpropyl]amino]acetic Acid Sodium

| Counter Ion (theoretical counter ion: alvimopan) | Solvent | Condition[a] | Observation | XRPD Result[b] |
|---|---|---|---|---|
| sodium hydroxide, (2:1) | ethanol | roto evap; dried in 80° C. oven | white solids and flakes; sample turned brown after drying; not birefringent | — |
|  | 1:1:1 dioxane:t-BuOH:water | lyophilized; dried in 100° C. vac oven | off-white to yellow solids; not birefringent | amorphous + peak |

[a]FE = fast evaporation; AS/S = antisolvent added to solution; centrivap = evaporation of solvent during centrifugation under vacuum; roto evap = rotary evaporation; vac = vacuum
[b]IS = insufficient sample for analysis

TABLE 13

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid Sodium Salt (1:1, Sodium Hydroxide) Prepared by Lyophilization with 100° C. Vacuum Oven Heat Treatment

| Analytical Technique | Results[a] |
|---|---|
| XRPD | amorphous |
| DSC | endo at max temp 82° C., endo at max temp 130° C. |
| Cycling DSC | 1st heating: endo at max temp 131° C. |
|  | 2nd heating: $T_g$ onset = 118° C., inflection = 123° C., offset = 123° C. |
|  | 3rd heating: $T_g$ onset = 118° C., inflection = 123° C., offset = 123° C. |
| TGA | 0.7% weight loss between 25° C. and 200° C. |
| Karl Fischer | 2.04% water content |
| 1H NMR | indicate salt formation |
| Elemental Analysis | 4% sodium present; 1:1 stoichiometry |
| Moisture Sorption | 2.8% lost upon equilibration at 5% RH |
|  | 62.2% weight gain between 5% and 95% RH |
|  | 58.2% weight lost upon desorption |
| XRPD after Moisture Sorption | peak + amorphous |

[a]endo = endotherm; exo = exotherm; max = maximum; temp = temperature; $T_g$ = glass transition temperature; RH = relative humidity

TABLE 14

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid Sodium Salt (2:1, Sodium Carbonate) Prepared by Lyophilization with 100° C. Vacuum Oven Heat Treatment

| Analytical Technique | Results[a] |
|---|---|
| XRPD | Amorphous |
| DSC | endo at max temp 132° C., endo at max temp 149° C. |
| Cycling DSC | 1st heating: endo at max temp 70° C., endo at max temp 133° C. |
|  | 2nd heating: $T_g$ onset = 121° C., inflection = 125° C., offset = 125° C. |
|  | 3rd heating: $T_g$ onset = 121° C., inflection = 125° C., offset = 126° C. |
| TGA | 0.8% weight loss between 25° C. and 200° C. |
| Karl Fischer | 3.76% water content |
| 1H NMR | indicate salt formation |
| Elemental Analysis | 9% sodium present; 2:1 stoichiometry |
| Moisture Sorption | 0.1% lost upon equilibration at 5% RH |
|  | 117.4% weight gain between 5% and 95% RH |
|  | 112.9% weight lost upon desorption |
| XRPD after Moisture Sorption | sample deliquesced |

[a]endo = endotherm; exo = exotherm; max = maximum; temp = temperature; $T_g$ = glass transition temperature; RH = relative humidity

TABLE 15

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid Sodium Salt:HPMC (70:30) Solid Dispersion Prepared by Lyophilization with 100° C. Vacuum Oven Heat Treatment

| Analytical Technique | Results[a] |
|---|---|
| XRPD | Amorphous |
| DSC | endo at max 69° C. and 134° C. |
| Cycling DSC | 1st heating: endo at 67° C., 2nd heating: no endo events, 3rd heating: endo at 136° C. |
| TGA | 0.5% weight loss between 25° C. and 150° C. |
| Moisture Sorption | 96% weight gain between 5% and 95% RH; 91% weight loss between 95% and 5% RH |
| XRPD after Moisture Sorption | Amorphous |
| 1H NMR | consistent with 2:1 sodium salt |

[a]endo = endotherm; max = maximum; RH = relative humidity

TABLE 16

Characterization Data of 0.125:1 Mannitol:Amorphous [[2(S)-[[4(R)-(3-hydroxyphenyl)-3(R),4-dimethyl-piperidinyl]methyl]-1-oxo-3-phenylpropyl]amino]acetic Acid Sodium Salt Solid Dispersion Prepared by Lyophilization with 100° C. Vacuum Oven Heat Treatment

| Analytical Technique | Results[a] |
|---|---|
| XRPD | amorphous + peak |
| DSC | endo at max 78° C., 117° C., and 156° C. |
| Cycling DSC | 1st heating: endo at 79° C. |
|  | 2nd heating: $T_g$ onset 108° C., inflection 112° C., offset 114° C. |
|  | 3rd heating: $T_g$ onset 107° C., inflection 112° C., offset 115° C. |

TABLE 16-continued

Characterization Data of 0.125:1 Mannitol:Amorphous [[2(S)-[[4(R)-(3-hydroxyphenyl)-3(R),4-dimethyl-piperidinyl]methyl]-1-oxo-3-phenylpropyl]amino]acetic Acid Sodium Salt Solid Dispersion Prepared by Lyophilization with 100° C. Vacuum Oven Heat Treatment

| Analytical Technique | Results[a] |
| --- | --- |
| TGA | 2.2% weight loss between 25° and 200° C. |
| $^1$H NMR | consistent with 2:1 sodium salt |

[a]endo = endotherm; max = maximum

TABLE 17

Characterization Data of 0.25:1 Mannitol:Amorphous [[2(S)-[[4(R)-(3-hydroxyphenyl)-3(R),4-dimethyl-piperidinyl]methyl]-1-oxo-3-phenylpropyl]amino]acetic Acid Sodium Salt Mixture Prepared by Lyophilization with 100° C. Vacuum Oven Heat Treatment

| Analytical Technique | Results[a] |
| --- | --- |
| XRPD | amorphous + peak |
| DSC | endo at max 104° C. and 181° C. |
| Cycling DSC | $1^{st}$ heating: endo at 67° C., 99° C. |
| | $2^{nd}$ heating: $T_g$ onset 91° C., inflection 102° C., offset 103° C. |
| | $3^{rd}$ heating: $T_g$ onset 93° C., inflection 102° C., offset 104° C. |
| TGA | 0.6% weight loss between 25° and 150° C. |
| $^1$H NMR | consistent with 2:1 sodium salt |

[a]endo endotherm; max = maximum

TABLE 18

Characterization Data of 0.5:1 Mannitol:Amorphous [[2(S)-[[4(R)-(3-hydroxyphenyl)-3(R),4-dimethyl-piperidinyl]methyl]-1-oxo-3-phenylpropyl]amino]acetic Acid Sodium Salt Mixture Prepared by Lyophilization with 100° C. Vacuum Oven Heat Treatment

| Analytical Technique | Results[a] |
| --- | --- |
| XRPD | amorphous + peak |
| DSC | broad, shallow endo between 75° and 125° C. |
| Cycling DSC | $1^{st}$ heating: endo at 62° C., 87° C. |
| | $2^{nd}$ heating: $T_g$ onset 78° C., inflection 83° C., offset 87° C. |
| | $3^{rd}$ heating: $T_g$ onset 78° C., inflection 84° C., offset 87° C. |
| TGA | 0.5% weight loss between 25° and 150° C. |
| $^1$H NMR | consistent with 2:1 sodium salt |

[a]endo = endotherm; max = maximum

TABLE 19

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid Sodium Salt:PVP (70:30) Solid Dispersion Prepared by Lyophilization with 100° C. Vacuum Oven Heat

| Analytical Technique | Results[a] |
| --- | --- |
| XRPD | amorphous |
| DSC | endo at max 69° C., 145° C., and 170° C. |
| Cycling DSC | $1^{st}$ heating: endo at 64° C., $2^{nd}$ heating: no endo events, $3^{rd}$ heating: endo at 142° C. |
| TGA | 2.3% weight loss between 25° C. and 200° C. |
| Moisture Sorption | 90% weight gain between 5% and 95% RH; 85% weight loss between 95% and 5% RH |
| XRPD after Moisture Sorption | IS[b] |
| $^1$H NMR | consistent with 2:1 sodium salt |

[a]endo = endotherm; max = maximum; RH = relative humidity
[b]IS = insufficient sample amount for analysis

TABLE 20

Characterization Data of Amorphous [[2(S)-[[4(R)-(3-hydroxyphenyl)-3(R),4-dimethyl-piperidinyl]methyl]-1-oxo-3-phenylpropyl]amino]acetic Acid Sodium Salt:PVP/VA$_c$ (70:30) Solid Dispersion Prepared by Lyophilization with 100° C. Vacuum Oven Heat Treatment (Sample ID 1910-06-02)

| Analytical Technique | Results[a] |
| --- | --- |
| XRPD | amorphous |
| DSC | endo at max 72° C. and 138° C. |
| Cycling DSC | $1^{st}$ heating: endo at 93° C., $2^{nd}$ heating: no endo events, $3^{rd}$ heating: endo at 141° C. |
| TGA | 0.9% weight loss between 25° C. and 200° C. |
| Moisture Sorption | 95% weight gain between 5% and 95% RH; 92% weight loss between 95% and 5% RH |
| XRPD after Moisture Sorption | amorphous |
| $^1$H NMR | consistent with 2:1 sodium salt |

[a]endo = endotherm; max = maximum; RH = relative humidity

Relative humidity stress studies were conducted on the amorphous materials. Physical mixtures of alvimopan and mannitol were prepared and analyzed by XRPD to ascertain the minimum amount of crystalline alvimopan needed for detection by XRPD (Table 21). The stress studies are summarized in Table 22 through Table 28.

TABLE 21

XRPD Approximate Detection Limit of [[2(S)-[[4(R)-(3-hydroxyphenyl)-3(R),4-dimethyl-piperidinyl]methyl]-1-oxo-3-phenylpropyl]amino]acetic Acid in Solid Dispersions

| Theoretical % Alvimopan[a] | XRPD File |
| --- | --- |
| 6 | Form I mannitol |
| 11 | Form I mannitol |
| 16 | Form I mannitol with minor Form A |
| 21 | Form I mannitol with minor Form A |

[a]Rounded to the nearest percent

TABLE 22

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under Ambient Conditions

| Description[a] | Days Stressed[b] | Observation | XRPD Result[c] |
|---|---|---|---|
| ethanol roto evap at 30° C.; 100° C. vac oven | 7 | white solids; not birefringent | amorphous |
| | 17 | white solids; not birefringent | amorphous |
| | 30 | white solids, flakes; not birefringent | amorphous |
| | 60 | white solids; not birefringent | amorphous |
| Mannitol (0.3 wt. fraction); lyophilized; 100° C. vac oven | 7 | off-white solids; not birefringent | PC; mannitol Form II + III |
| | 17 | off-white solids; not birefringent | PC; mannitol Form II + III |
| | 30 | off-white solids; not birefringent | PC; mannitol Form II + III |
| | 60 | off-white solids; not birefringent | PC; mannitol Form II + III |
| lyophilized; 100° C. vac oven | 7 | white solids; not birefringent | amorphous |
| | 17 | white solids; not birefringent | amorphous |
| | 30 | white solids; not birefringent | amorphous |
| | 60 | white solids; not birefringent | amorphous |
| HPMC (0.3 wt. fraction); lyophilized; 100° C. vac oven | 7 | white solids; not birefringent | amorphous |
| | 17 | white solids; not birefringent | amorphous |
| | 30 | white solids; not birefringent | amorphous |
| | 60 | white fluffy solids; not birefringent | amorphous |
| 2:1 sodium carbonate attempt; lyophilized; 100° C. vac oven | 7 | off-white, yellow solid; not birefringent | amorphous + peak |
| | 17 | yellow solid; not birefringent | amorphous + peak |
| | 30 | off-white, yellow solid; not birefringent | amorphous + peak; SS |
| 1:1 sodium hydroxide attempt; lyophilized; 100° C. vac oven | 7 | off-white solid; not birefringent | amorphous + peak |
| | 17 | off-white, yellow solid; not birefringent | amorphous + peak |
| | 30 | off-white, yellow solid; not birefringent | amorphous + peak |

[a]roto evap = rotary evaporation; wt. = weight; vac = vacuum; PVP = polyvinylpyrrolidone; PVP/VA$_c$ = poly(1-vinylpyrrolidone-co-vinyl acetate); HPMC = hydroxypropylmethyl cellulose
[b]Samples stresses under ambient conditions. Ambient conditions were approximately 24% relative humidity and 22° C.
[c]PC = poorly crystalline; SS = small sample amount

TABLE 23

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under Ambient Conditions, Continued

| Description[a] | Days Stressed[b] | Observation | XRPD Result[c] |
|---|---|---|---|
| 2:1 sodium carbonate attempt; lyophilized; 100° C. vac oven | 13 | white solids; not birefringent | amorphous + peak |
| | 43 | white and yellow solids; not birefringent | amorphous + peak |
| PVP/VA$_c$; (0.3 wt. fraction); ethanol roto evap at 30° C.; 100° C. vac oven | 7 | white solids; not birefringent | amorphous |
| | 17 | white flakes, solids; not birefringent | amorphous |
| | 30 | white flakes, solids; not birefringent | amorphous |
| | 60 | white flakes, solids; not birefringent | amorphous |

TABLE 23-continued

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under Ambient Conditions, Continued

| Description[a] | Days Stressed[b] | Observation | XRPD Result[c] |
|---|---|---|---|
| PVP (0.3 wt. fraction); ethanol roto evap at 30° C.; 100° C. vac oven | 7 | white solids; not birefringent | amorphous |
| | 17 | white flakes, solids; not birefringent | amorphous |
| | 30 | white flakes, solids; not birefringent | amorphous |
| | 60 | white flakes, solids; not birefringent | amorphous |

[a] roto evap = rotary evaporation; wt. = weight; vac = vacuum; PVP = polyvinylpyrrolidone; PVP/VA$_c$ = poly(1-vinylpyrrolidone-co-vinyl acetate); HPMC = hydroxypropylmethyl cellulose
[b] Samples stresses under ambient conditions. Ambient conditions were approximately 24% relative humidity and 22° C.
[c] PC = poorly crystalline; SS = small sample amount

TABLE 24

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under 53% Relative Humidity and Ambient Temperature

| Description[a] | Days Stressed | Observation[b] | XRPD Result[c] |
|---|---|---|---|
| ethanol roto evap at 30° C.; 100° C. vac oven | 7 | white solids; not birefringent | amorphous |
| | 17 | white solids; not birefringent | amorphous |
| | 30 | white solids; not birefringent | amorphous |
| | 60 | white solids, flakes; not birefringent | amorphous |
| Mannitol (0.3 wt. fraction); lyophilized; 100° C. vac oven | 7 | off-white solid; not birefringent | PC; mannitol Forms II + III |
| | 17 | off-white solid; not birefringent | PC; mannitol Forms II + III |
| | 30 | off-white, yellow solid; not birefringent | PC; mannitol Forms II + III |
| | 60 | off-white, solids; not birefringent | PC; mannitol Forms II + III |
| lyophilized; 100° C. vac oven | 7 | white solids; not birefringent | amorphous |
| | 17 | white solids; not birefringent | amorphous |
| | 30 | white solids; not birefringent | amorphous |
| | 60 | white solids; not birefringent | amorphous |
| HPMC (0.3 wt. fraction); lyophilized; 100° C. vac oven | 7 | white solids; not birefringent | amorphous |
| | 17 | white solids; not birefringent | amorphous |
| | 30 | white solids; not birefringent | amorphous |
| | 60 | white solids; not birefringent | amorphous |
| 2:1 sodium carbonate attempt; lyophilized; 100° C. vac oven | 7 | white solids; not birefringent | amorphous + peak |
| | 17 | white solids; not birefringent | amorphous + peak |
| | 30 | white solids; not birefringent | amorphous + peak |
| | 60 | white solids; not birefringent | amorphous + peak |

[a] roto evap = rotary evaporation; wt. = weight; vac = vacuum; PVP = polyvinylpyrrolidone; PVP/VA$_c$ = poly(1-vinylpyrrolidone-co-vinyl acetate); HPMC = hydroxypropylmethyl cellulose
[b] SS = small sample
[c] PC = poorly crystalline

TABLE 25

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under 53% Relative Humidity and Ambient Temperature

| Description[a] | Days Stressed | Observation[b] | XRPD Result[c] |
|---|---|---|---|
| 1:1 sodium hydroxide attempt; lyophilized; 100° C. vac oven | 7 | white solids; not birefringent | amorphous + peak |
| | 17 | white solids; not birefringent | amorphous + peak |
| | 30 | white solids; not birefringent | amorphous + peak |
| | 60 | white solids; not birefringent | amorphous + peak |
| 2:1 sodium carbonate attempt; lyophilized; 100° C. vac oven | 13 | white solids; not birefringent | amorphous |
| | 43 | white solids; not birefringent; SS | amorphous |
| PVP/VA$_c$; (0.3 wt. fraction); ethanol roto evap at 30° C.; 100° C. vac oven | 7 | white solids and flakes; not birefringent | amorphous |
| | 17 | white solids and flakes; not birefringent | amorphous |
| | 30 | white solids and flakes; not birefringent | amorphous |
| | 60 | white solids and flakes; not birefringent | amorphous |
| PVP (0.3 wt. fraction); ethanol roto evap at 30° C.; 100° C. vac oven | 7 | white solids and flakes; not birefringent | amorphous |
| | 17 | white solids and flakes; not birefringent | amorphous |
| | 30 | white solids and flakes; not birefringent | amorphous |
| | 60 | white solids and flakes; not birefringent | amorphous |

[a] roto evap = rotary evaporation; wt. = weight; vac = vacuum; PVP = polyvinylpyrrolidone; PVP/VA$_c$ = poly(1-vinylpyrrolidone-co-vinyl acetate); HPMC = hydroxypropylmethyl cellulose
[b] SS = small sample
[c] PC = poorly crystalline

TABLE 26

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under 97% Relative Humidity and Ambient Temperature

| Description[a] | Days Stressed | Observation | XRPD Result[b] |
|---|---|---|---|
| ethanol roto evap at 30° C.; 100° C. vac oven | 7 | white solids; some birefringence | Form A |
| Mannitol (0.3 wt. fraction); lyophilized; 100° C. vac oven | 7 | white solids; not birefringent | PC; Form A + mannitol Form I + II |
| lyophilized; 100° C. vac oven | 7 | off-white solids; some birefringence | Form A |
| HPMC (0.3 wt. fraction); lyophilized; 100° C. vac oven | 7 | white solids; slight birefringence | Form A |
| 2:1 sodium carbonate attempt; lyophilized; 100° C. vac oven | 3 | deliquescence; not birefringent | — |
| 1:1 sodium hydroxide attempt; lyophilized; 100° C. vac oven | 7 | white solids; slight birefringence | Form A |
| 2:1 sodium carbonate attempt; lyophilized; 100° C. vac oven | 1 | deliquescence; not birefringent | — |

TABLE 26-continued

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under 97% Relative Humidity and Ambient Temperature

| Description[a] | Days Stressed | Observation | XRPD Result[b] |
|---|---|---|---|
| PVP/VA$_c$; (0.3 wt. fraction); ethanol roto evap at 30° C.; 100° C. vac oven | 7 | white solids; birefringence | Form A |
| PVP (0.3 wt. fraction); ethanol roto evap at 30° C.; 100° C. vac oven | 7 | white solids; birefringence | Form A |

[a]roto evap = rotary evaporation; wt. = weight; vac vacuum; PVP = polyvinylpyrrolidone; PVP/VA$_c$ = poly(1-vinylpyrrolidone-co-vinyl acetate); HPMC = hydroxypropylmethyl cellulose
[b]PC = poorly crystalline

TABLE 27

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under 75% Relative Humidity and 40° C.

| Description[a] | Days Stressed | Observation | XRPD Result |
|---|---|---|---|
| ethanol roto evap at 30° C.; 100° C. vac oven | 7 | white solids; birefringence | PC; Form A |
| Mannitol (0.3 wt. fraction); lyophilized; 100° C. vac oven | 7 | off-white solids; not birefringent | PC; mannitol Forms II + III |
|  | 17 | off-white solids; not birefringent | PC; mannitol Forms II + III |
|  | 30 | off-white, yellow solids; not birefringent | PC; Form A; mannitol Forms II + III |
|  | 60 | off-white, yellow solids; not birefringent | PC; Form A; mannitol Forms II + III |
| lyophilized; 100° C. vac oven | 7 | white solids; not birefringent | amorphous |
|  | 17 | white solids; not birefringent | amorphous |
|  | 30 | white solids; not birefringent | amorphous |
|  | 60 | white solids; not birefringent | amorphous |
| HPMC (0.3 wt. fraction); lyophilized; 100° C. vac oven | 7 | white solids; not birefringent | amorphous |
|  | 17 | white solids; not birefringent | amorphous |
|  | 30 | white solids; not birefringent | amorphous |
|  | 60 | white solids; not birefringent | amorphous |
| 2:1 sodium carbonate attempt; lyophilized; 100° C. vac oven | 3 | deliquescence; droplets with birefringent needles | — |
| 1:1 sodium hydroxide attempt; lyophilized; 100° C. vac oven | 3 | deliquescence; not birefringent | — |
| 2:1 sodium carbonate attempt; lyophilized; 100° C. vac oven | 1 | deliquescence; not birefringent | — |
| PVP/VA$_c$; (0.3 wt. fraction); ethanol roto evap at 30° C.; 100° C. vac oven | 7 | white solids and flakes; not birefringent | amorphous |
|  | 17 | white solids and flakes; not birefringent | amorphous |
|  | 30 | white solids and flakes; not birefringent | amorphous |
|  | 60 | white solids and flakes; not birefringent | amorphous |
| PVP (0.3 wt. fraction); ethanol roto evap at 30° C.; 100° C. vac oven | 7 | white solids and flakes; not birefringent | amorphous |
|  | 17 | white solids and flakes; not birefringent | amorphous |

TABLE 27-continued

Stability Studies of Amorphous [[2(S)-[[4(R)-(3-hydroxyphenyl)-3(R),4-dimethyl-piperidinyl]methyl]-1-oxo-3-phenylpropyl]amino]acetic Acid Samples Stressed under 75% Relative Humidity and 40° C.

| Description[a] | Days Stressed | Observation | XRPD Result |
|---|---|---|---|
| | 30 | white solids and flakes; not birefringent | amorphous |
| | 60 | white solids and flakes; not birefringent | amorphous |
| PVP (0.3 wt. fraction); amorphous sodium salt; lyophilization; 100° C. vac oven; sub-sample of 1910-24-03 | 5 | yellow solids; some birefringence | amorphous |
| | 18 | off white to light brown solids; birefringent | amorphous + peak |
| HPMC (0.3 wt. fraction); amorphous sodium salt; lyophilization; 100° C. vac oven; sub-sample of 1910-24-01 | 5 | white, off-white solids; not birefringence | amorphous + peak |
| | 18 | white to off white solids; not birefringent | amorphous + peak |
| PVP/VA$_c$ (0.3 wt. fraction); amorphous sodium salt; lyophilization; 100° C. vac oven; sub-sample of 1910-24-02 | 5 | yellow globules; slight birefringence | amorphous + peak |
| | 18 | deliquescence; yellow solid | — |
| 0.5:1 mannitol:alvimopan; lyophilized; 100° C. vac oven | 5 | deliquescence; yellow solid | — |
| 0.25:1 mannitol:alvimopan; lyophilized; 100° C. vac oven | 5 | deliquescence; yellow/brown solid | — |
| 0.125:1 mannitol:alvimopan; lyophilized; 100° C. vac oven | 5 | deliquescence; yellow solid | — |

[a] roto evap = rotary evaporation; wt. = weight; vac = vacuum; PVP = polyvinylpyrrolidone; PVP/VA$_c$ = poly(1-vinylpyrrolidone-co-vinyl acetate); HPMC = hydroxypropylmethyl cellulose
[b] PC = poorly crystalline Table 28 to Table 31 summarize the characterization data of alvimopan lyophilized drug product and samples containing increase loading of alvimopan.

TABLE 28

Characterization Data of Alvimopan Drug Product

| Analytical Technique | Results[a] |
|---|---|
| XRPD | Mannitol Forms I + III; alvimopan not detected |
| DSC | endo at 137° C., shoulder at 146° C., endo at 152° C. endo at 78° C., 139° C., 153° C. |
| Modulated DSC | endo at 125° C., 133° C., 143° C., 149° C. |
| TGA | 4.9% weight loss between 25° C. and 200° C. |
| $^1$H NMR | consistent with 2:1 sodium salt |

[a] endo = endotherm

TABLE 29

Characterization Data of Alvimopan Drug Product with 10% Alvimopan Drug Load

| Analytical Technique | Results[a] |
|---|---|
| XRPD | amorphous + minor mannitol Form III amorphous + minor mannitol Form III |
| DSC | endo at 88° C., 141° C., 150° C. |
| Cycling DSC | 1$^{st}$ heating: endo at 70° C. and 96° C. 2$^{nd}$ heating: T$_g$ onset 101.6° C., inflection 102.0° C., offset 102.4° C. 3$^{rd}$ heating: T$_g$ onset 101.7° C., inflection 102.3° C., offset 102.4° C., shoulder at 143° C., endo at 152° C. |
| TGA | 3.2% weight loss between 25° C. and 150° C. |
| $^1$H NMR | consistent with 2:1 sodium salt |

[a] endo = endotherm

TABLE 30

Characterization Data of Alvimopan Drug Product with 20% Alvimopan Drug Load

| Analytical Technique | Results[a] |
|---|---|
| XRPD | amorphous + peak |
| DSC | endo at 92° C. and 150° C. |
| Cycling DSC | 1$^{st}$ heating: endo at 73° C. and 97° C. 2$^{nd}$ heating: T$_g$ onset 102.2° C., inflection 102.6° C., offset 102.9° C. 3$^{rd}$ heating: T$_g$ onset 101.9° C., inflection 102.3° C., offset 102.6° C., shoulder at 140° C., endo at 152° C. |
| TGA | 3.4% weight loss between 25° C. and 150° C. |
| $^1$H NMR | consistent with 2:1 sodium salt |

[a] endo = endotherm

TABLE 31

Characterization Data of Alvimopan Drug Product with 30% Alvimopan Drug Load

| Analytical Technique | Results[a] |
|---|---|
| XRPD | amorphous + mannitol Forms I and III |
| DSC | endo at 73° C. and 149° C. |
| Cycling DSC | 1st heating: endo at 79° C. and 103° C. |
| | 2nd heating: $T_g$ onset 101.5° C., inflection 101.9° C., offset 102.3° C. |
| | 3rd heating: $T_g$ onset 101.7° C., inflection 102.1° C., offset 102.4° C., shoulder at 140° C., endo at 150° C. |
| TGA | 3.5% weight loss between 25° C. and 150° C. |
| $^1$H NMR | consistent with 2:1 sodium salt |

[a]endo = endotherm

Characterization of Amorphous [[2(S)-[[4(R)-(3-hydroxyphenyl)-3(R),4-dimethyl-piperidinyl]methyl]-1-oxo-3-phenylpropyl]amino]acetic acid and Solid Dispersions Amorphous [[2(S)-[[4(R)-(3-hydroxyphenyl)-3(R),4-dimethyl-piperidinyl]methyl]-1-oxo-3-phenylpropyl]amino]acetic acid and solid dispersions of [[2(S)-[[4(R)-(3-hydroxyphenyl)-3(R),4-dimethyl-piperidinyl]methyl]-1-oxo-3-phenylpropyl]amino]acetic acid were prepared by rotary evaporation and lyophilization (Table 1, Table 7). The initial amorphous solids were found to lose between 2% and 5% of weight upon TGA analysis. TG-IR analysis indicated that the weight loss was due to the solvents of preparation:ethanol and residual water for rotary evaporation and 1,4-dioxane, t-butanol, and water for lyophilization All amorphous samples were dried at 100° C. under vacuum for approximately two days to remove residual solvent. Criteria for acceptable amorphous materials were that the samples had to be amorphous by XRPD and contain <1% solvent content as observed by TGA and/or Karl Fisher analysis.

Pharmaceutically acceptable excipients were selected for stabilizing amorphous alvimopan: HPMC, mannitol, PVP, and PVP/VAc. The Gordon-Taylor equation was also used to predict $T_g$ values for [[2(S)-[[4(R)-(3-hydroxyphenyl)-3(R),4-dimethyl-piperidinyl]methyl]-1-oxo-3-phenylpropyl]amino]acetic acid:excipient solid dispersions with a weight fraction of 70:30. Thermal behavior of the excipients used in this study is summarized in Table 5 and was determined experimentally. The glass transition temperature of mannitol was obtained from a literature source. Glass transition temperatures were predicted for comparison to experimentally determined $T_g$ values (Table 6).

1. Amorphous [[2(S)-[[4(R)-(3-hydroxyphenyl)-3(R),4-dimethyl-piperidinyl]methyl-1-oxo-3-phenylpropyl]amino]acetic acid Amorphous [[2(S)-[[4(R)-(3-hydroxyphenyl)-3(R),4-dimethyl-piperidinyl]methyl]-1-oxo-3-phenylpropyl]amino]acetic acid was prepared by rotary evaporation of ethanol solutions or lyophilization of 1,4-dioxane:t-butanol:water (1:1:1) solutions (Table 1). [[2(S)-[[4(R)-(3-Hydroxyphenyl)-3(R),4-dimethyl-piperidinyl]methyl]-1-oxo-3-phenylpropyl]amino]acetic acid from both methods of preparation were amorphous by XRPD. Characterization data are summarized in Table 2 and Table 3.

DSC analysis of the sample prepared by rotary evaporation exhibits two endothermic events at maximum temperatures of 68° C. and 138° C. The lyophilized sample has endothermic events at maximum temperatures of 72° C. and 123° C. A previous lyophilized sample of alvimopan showed an exothermic event upon DSC analysis. Hot stage microscopy analysis was performed to investigate this thermal event (Table 4). However, thermal behavior that may indicate an exothermic event was not observed. The exothermic event was not observed in subsequently prepared lyophilized materials. The nature of the exothermic event was not determined and is likely an artifact of that particular sample.

Evaluation of the glass transition temperature (Tg) indicates different values for the two materials. Cycling DSC analysis of the rotary evaporation sample has a Tg with an onset temperature of approximately 125° C. The lyophilized sample has a Tg with an onset temperature of approximately 112° C. The difference in Tg values may be a result of the effects that the residual solvents had on the amorphous solids. TGA analysis of the two samples show a weight loss of approximately 0.5% between 25° C. and 200° C.

Moisture sorption analysis for both the rotary evaporated and lyophilized samples show an approximate weight gain of 13% between 5% and 95% relative humidity that is lost during desorption with hysteresis. XRPD analysis of the solid material remaining after the moisture sorption analysis shows that the rotary evaporated sample crystallized to low crystalline material that may consist of amorphous, Form A (dihydrate), and/or Form B (anhydrous) of alvimopan. The lyophilized sample appears to have remained amorphous after moisture sorption analysis.

Since the two amorphous samples have different Tg values, both samples were used for subsequent stability studies.

2. [[2(S)-[[4(R)-(3-hydroxyphenyl)-3(R),4-dimethyl-piperidinyl]methyl]-1-oxo-3-phenylpropyl]amino]acetic acid: HPMC Solid Dispersion A solid dispersion of alvimopan:HPMC (70:30) was prepared by lyophilization of 1,4-dioxane:t-butanol:water (1:1:1). The solid material was amorphous by XRPD. Characterization data are summarized in Table 8.

DSC analysis shows two endothermic events at maximum temperatures of 72° C. and 126° C. A weight loss of approximately 0.5% was observed between 25° C. and 200° C. by TG analysis. Cycling DSC analysis shows that the amorphous material has a Tg with an onset temperature between approximately 115° C. to 117° C. This value is 17° C. lower than the predicted Tg.

Moisture sorption analysis shows an approximate weight gain of 22% between 5% and 95% relative humidity. The sample did not meet the weight criteria during the analysis suggesting that the material could possibly sorb more water at each humidity step. The weight gain is loss during desorption with some hysteresis. XRPD analysis indicates that the sample is amorphous after moisture sorption analysis.

3. [[2(S)-[[4(R)-(3-hydroxyphenyl)-3(R),4-dimethyl-piperidinyl]methyl]-1-oxo-3-phenylpropyl]amino]acetic acid: Mannitol (70:30) Non-Homogeneous Mixture A solid dispersion of alvimopan:mannitol (70:30) was prepared by lyophilization of 1,4-dioxane:r-butanol:water (1:1:1). The solid material shows diffraction peaks that are consistent with mannitol Forms II and III. Diffraction peaks representative of known alvimopan forms are not present. Characterization data are summarized in Table 9.

DSC analysis shows three endothermic events at maximum temperatures of 150° C., 165° C., and 294° C. The endothermic events at 150° C. and 165° C. are consistent with the melting of mannitol Forms III and II, respectively. The endothermic event at 294° C. may be due to decomposition. A weight loss of approximately 0.7% was observed between 25° C. and 190° C. by TG analysis.

Even though the solid dispersion shows some crystallinity by XRPD and DSC, cycling DSC analysis indicates that a solid dispersion is possibly formed. Cycling DSC analysis shows that the amorphous portion of the solid material has an apparent Tg with an onset temperature of approximately 106° C. This Tg value is 21° C. higher than the predicted value (Table 6). Since mannitol may behave as a plasticiser, increasing amounts of amorphous mannitol will result in a significant decrease in the glass transition of the mixture. In order to achieve a glass transition temperature of 106° C., approximately 0.10 (weight fraction) of mannitol may be needed to interact with amorphous alvimopan to form a solid dispersion.

Moisture sorption analysis shows an approximate weight gain of 13% between 5% and 95% relative humidity, which is lost during desorption with some hysteresis. XRPD analysis indicates that the sample has diffraction peaks consistent with mannitol Forms II and III with some amorphous content present. Crystalline alvimopan was not detected in the sample.

Even though the [[2(S)-[[4(R)-(3-hydroxyphenyl)-3(R),4-dimethyl-piperidinyl]methyl]-1-oxo-3-phenylpropyl]amino] acetic acid:mannitol material appears to be a non-homogeneous mixture (mixture of amorphous and crystalline material), this material was used in the stability stress studies since an apparent Tg was measured.

4. [[2(S)-[[4(R)-(3-hydroxyphenyl)-3(R),4-dimethyl-piperidinyl]methyl]-1-oxo-3-phenylpropyl]amino]acetic acid: PVP (70:30) Solid Dispersion A solid dispersion of [[2(S)-[[4(R)-(3-hydroxyphenyl)-3(R),4-dimethyl-piperidinyl]methyl]-1-oxo-3-phenylpropyl]amino]acetic acid:PVP (70:30) was prepared by rotary evaporation of ethanol. The solid material is amorphous by XRPD. Characterization data are summarized in Table 10.

DSC analysis shows one endothermic event at a maximum temperature of 136° C. A weight loss of approximately 0.5% was observed between 25° C. and 200° C. by TG analysis. Cycling DSC analysis shows that the solid dispersion has a Tg with an onset temperature of approximately 123° C. The measured Tg is 17° C. lower than the predicted value.

Moisture sorption analysis shows an approximate weight gain of 30% between 5% and 95% relative humidity. The sample did not meet the weight criteria during the analysis suggesting that the material could possibly sorb more water at each humidity step. The weight gain is loss during desorption with hysteresis. XRPD analysis indicates that the sample is amorphous.

5. [[2(S)-[[4(R)-(3-hydroxyphenyl)-3(R),4-dimethyl-piperidinyl]methyl]-1-oxo-3-phenylpropyl]amino]acetic acid: PVP/VAc (70:30) Solid Dispersion A solid dispersion of alvimopan:PVP/VAc (70:30) was prepared by rotary evaporation of ethanol. The solid material is amorphous by XRPD. Characterization data are summarized in Table 11.

DSC analysis shows one endothermic event at a maximum temperature of 125° C. A weight loss of approximately 0.2% was observed between 25° C. and 200° C. by TG analysis. Cycling DSC analysis shows that the solid dispersion has a Tg with an onset temperature of approximately 117° C. The measured Tg value is in good agreement with the predicted Tg (Table 6).

Moisture sorption analysis shows an approximate weight gain of 23% between 5% and 95% relative humidity. The sample did not meet the weight criteria at some of the relative humidities suggesting that the material could possibly sorb more water at those humidity steps. The weight gain is loss during desorption with some hysteresis. XRPD analysis indicates that the sample is amorphous.

Characterization of Amorphous [[2(S)-[[4(R)-(3-hydroxyphenyl)-3(R),4-dimethyl-piperidinyl]methyl]-1-oxo-3-phenylpropyl]amino]acetic acid Sodium Salt and Solid Dispersions Amorphous alvimopan sodium salt was prepared by rotary evaporation and lyophilization (Table 12). The amorphous salt was prepared with a 1:1 and 2:1 sodium ion:alvimopan molar ratio. Characterization data for the two amorphous solids are summarized in Table 14 and Table 15. Attempts were made to prepare solid dispersions of the amorphous salts using HPMC, mannitol, PVP, and PVP/VAc as the carrier excipients. Characterization data for those solid materials are summarized in Table 15 through Table 20. Detailed results are provided in the following sections.

1. Amorphous [[2(S)-[[4(R)-(3-hydroxyphenyl)-3(R),4-dimethyl-piperidinyl]methyl]-1-oxo-3-phenylpropyl]amino] acetic acid Sodium Salt (1:1)

Amorphous [[2(S)-[[4(R)-(3-hydroxyphenyl)-3(R),4-dimethyl-piperidinyl]methyl]-1-oxo-3-phenylpropyl]amino] acetic acid sodium salt (1:1) was prepared by lyophilization of 1,4-dioxane:butanol:water (1:1:1). The material was prepared using sodium hydroxide as the counter ion. The amorphous salt was also prepared using sodium carbonate as the counter ion (Table 12). Characterization data are summarized in Table 13. The solid material is amorphous by XRPD. A broad peak is observed at approximately 4.7° 2θ.

DSC analysis shows two endothermic events at maximum temperatures of 82° C. and 130° C. A weight loss of approximately 0.7% was observed between 25° C. and 200° C. by TG analysis. Cycling DSC analysis shows that the amorphous material has a Tg with an onset temperature of approximately 118° C.

The $^1$H NMR chemical shifts for the amorphous salt are different from the $^1$H NMR spectrum of alvimopan. The sodium salt displays a triplet of peaks at approximately 3.8 ppm, whereas the free acid displays a doublet in this region. Differences are also observed between 3.5 and 3.0 ppm and 2.9 and 2.5 ppm, which may indicate changes in the molecule consistent with a 1:1 sodium salt formation. Elemental analysis indicates the amorphous material contains approximately 5% of sodium, which is consistent with a 1:1 stoichiometry (Table 13).

Moisture sorption analysis shows an approximate weight gain of 62% between 5% and 95% relative humidity. The sample did not meet the weight criteria during the analysis suggesting that the material could possibly sorb more water at each humidity step. Approximately 58% of the weight is lost during desorption. XRPD analysis indicates that the sample is amorphous after moisture sorption analysis.

2. Amorphous [[2(S)-[[4(R)-(3-hydroxyphenyl)-3(R),4-dimethyl-piperidinyl]methyl]-1-oxo-3-phenylpropyl]amino] acetic acid Sodium Salt (2:1)

Amorphous [[2(S)-[[4(R)-(3-hydroxyphenyl)-3(R),4-dimethyl-piperidinyl]methyl]-1-oxo-3-phenylpropyl]amino] acetic acid sodium salt (2:1) was prepared by lyophilization of 1,4-dioxane:butanol:water (1:1:1). The material was prepared using sodium carbonate as the counter ion. The amorphous salt was also prepared using sodium hydroxide as the counter ion (Table 12). Characterization data are summarized in Table 14. The solid material was amorphous by XRPD. A broad peak is observed at approximately 4.7° 2θ.

DSC analysis shows two endothermic events at maximum temperatures of 132° C. and 148° C. A weight loss of approximately 0.8% was observed between 25° C. and 200° C. by TG analysis. Cycling DSC analysis shows that the amorphous material has a Tg with an onset temperature of approximately 121 ° C.

Solution ¹H NMR for the 2:1 amorphous salt shows chemical shifts associated with the phenol ring, which may suggest salt formation. A doublet of peaks is shifted from approximately 6.78 ppm to approximately 6.65 ppm in the 2:1 sodium salt. This chemical shift is not observed in the free acid or 1:1 amorphous sodium salt spectrum, which may indicate the formation of a 2:1 sodium salt. Elemental analysis indicates the amorphous material contains approximately 9% of sodium, which is consistent with a 2:1 stoichiometry (Table 14).

Moisture sorption analysis shows an approximate weight gain of 117% between 5% and 95% relative humidity. The sample did not meet the weight criteria during the analysis suggesting that the material could possibly sorb more water at each humidity step. Approximately 113% of the weight is lost during desorption with slight hysteresis. XRPD analysis was not performed post moisture sorption due to deliquescence of the material.

3. Amorphous [[2(S)-[[4(R)-(3-hydroxyphenyl)-3(R),4-dimethyl-piperidinyl]methyl]-1-oxo-3-phenylpropyl]amino] acetic acid Sodium Salt/HPMC (70:30) Mixture Attempts were made to prepare a solid dispersion with amorphous alvimopan sodium salt and HPMC. The amorphous material was prepared by lyophilization from 1,4-dioxane:f-butanol:water (1:1:1). Characterization data are summarized in Table 15. The material is amorphous by XRPD. DSC analysis exhibited two endothermic events at maximum temperatures 69° C. and 134° C., which may be due to the release of residual solvent. TG analysis showed a weight loss of approximately 0.5% between 25° C. and 150° C. Cycling DSC was performed to determine if the material has a measurable glass transition temperature. An endothermic event at approximately 67° C. was observed during the first heating, which may be due to the release of solvent from the material. No thermal events were observed during the second heating. An endothermic event was observed at approximately 136° C. during the third heating, which may be related to removal of residual solvent. Thermal events indicative of a glass transition temperature were not observed during the analysis. This may suggest that a solid dispersion was not formed between the amorphous salt and HPMC.

Moisture sorption indicates that the material gains approximately 96% weight between 5% and 95% relative humidity. Approximately 91% of the weight is loss during desorption with slight hysteresis. The material did not meet the weight requirement at each humidity step, which indicates that the material could absorb more water if left at each humidity step for longer durations. XRPD analysis indicates that the post moisture sorption sample is amorphous.

Solution ¹H NMR analysis shows chemical shifts that are consistent with the 2:1 amorphous sodium salt. The chemical shift of the doublet from 6.78 ppm to approximately 6.65 ppm is observed and suggest that the 2:1 salt was formed in the mixture. Chemical shifts associated with HPMC are also present.

Even though the material is amorphous and forms a 2:1 [[2(S)-[[4(R)-(3-hydroxyphenyl)-3(R),4-dimethyl-piperidinyl]methyl]-1-oxo-3-phenylpropyl]amino]acetic acid sodium salt, DSC analysis did not show a measurable glass transition temperature and suggest that a solid dispersion was not formed.

4. Amorphous [[2(S)-[[4(R)-(3-hydroxyphenyl)-3(R),4-dimethyl-piperidinyl]methyl]-1-oxo-3-phenylpropyl]amino] acetic acid Sodium Salt:Mannitol Mixtures Solid dispersions with amorphous [[2(S)-[[4(R)-(3-hydroxyphenyl)-3(R),4-dimethyl-piperidinyl]methyl]-1-oxo-3-phenylpropyl]amino]acetic acid sodium salt and mannitol at molar ratios of 0.125:1, 0.25:1 and 0.5:1 (mannitol: [[2(S)-[[4(R)-(3-hydroxyphenyl)-3(R),4-dimethyl-piperidinyl]methyl]-1-oxo-3-phenylpropyl]amino]acetic acid) were made. This was done to investigate the amount of mannitol needed to form a homogenous amorphous solid dispersion free of crystalline mannitol. These materials were prepared by lyophilization from 1,4-dioxane:t-butanol:water (1:1:1).

a. 0.125:1 Mannitol:Amorphous [[2(S)-[[4(R)-(3-hydroxyphenyl)-3(R),4-dimethyl-piperidinyl]methyl]-1-oxo-3-phenylpropyl]amino]acetic acid Sodium Salt Studies were conducted to prepare and characterize an amorphous [[2(S)-[[4(R)-(3-hydroxyphenyl)-3(R),4-dimethyl-piperidinyl]methyl]-1-oxo-3-phenylpropyl]amino] acetic acid sodium salt:mannitol solid dispersion. XRPD analysis indicates that the material is amorphous with a broad peak at approximately 4.6° 2θ. DSC analysis exhibits three endothermic events at maximum temperatures of approximately 78° C., 117° C., and 156° C. TG analysis showed a weight loss of approximately 2.2% between 25° C. and 200° C. Cycling DSC was performed to investigate the glass transition temperature. An apparent glass transition temperature with an approximate onset temperature of 107° C. was observed. This glass transition temperature is consistent with the amorphous [[2(S)-[[4(R)-(3-hydroxyphenyl)-3(R),4-dimethyl-piperidinyl]methyl]-1-oxo-3-phenylpropyl]amino] acetic acid:mannitol mixture, which may suggest that the presence of the sodium salt does not significantly affect the glass transition temperature. The measured glass transition temperature is also consistent with the predicted value of a [[2(S)-[[4(R)-(3-hydroxyphenyl)-3(R),4-dimethyl-piperidinyl]methyl]-1-oxo-3-phenylpropyl]amino]acetic acid solid dispersion containing a weight fraction of 0.10 mannitol.

Solution ¹H NMR analysis shows chemical shifts that are consistent with the 2:1 amorphous sodium salt. The chemical shift of the doublet from 6.78 ppm to approximately 6.65 ppm is observed and suggest that the 2:1 salt was formed in the mixture. Chemical shifts associated with mannitol are also present.

The data suggest that a solid dispersion consisting of the amorphous 2:1 [[2(S)-[[4(R)-(3-hydroxyphenyl)-3(R),4-dimethyl-piperidinyl]methyl]-1-oxo-3-phenylpropyl]amino] acetic acid sodium salt and mannitol was formed.

b. 0.25:1 Mannitol:Amorphous [[2(S)-[[4(R)-(3-hydroxyphenyl)-3(R),4-dimethyl-piperidinyl]methyl]-1-oxo-3-phenylpropyl]amino]acetic acid Sodium Salt Characterization data for this solid material is summarized in Table 17. The material is amorphous by XRPD with a broad peak at approximately 4.7° 2θ and additional peaks at high 2θ values, indicating that the material has some crystallinity. DSC analysis shows two endothermic events at approximately 104° C. and 181° C. TG analysis shows a weight loss of approximately 0.6% between 25° C. and 150° C. Cycling DSC analysis exhibits a glass transition with an onset temperature of approximately 92° C.

Solution ¹H NMR analysis shows chemical shifts that are consistent with the 2:1 amorphous sodium salt. The chemical shift of the doublet from 6.78 ppm to approximately 6.65 ppm is observed and suggest that the 2:1 salt was formed in the mixture. Chemical shifts associated with mannitol are also present.

Since the XRPD pattern indicates crystallinity, a homogeneous sample was not generated. However, the material does show an apparent glass transition temperature at approximately 92° C., which may indicate that a portion of the material formed a solid dispersion between the amorphous mannitol and amorphous 2:1 sodium salt.

c. 0.5:1 Mannitol:Amorphous [[2(S)-[[4(R)-(3-hydroxyphenyl)-3(R),4-dimethyl-piperidinyl]methyl]-1-oxo-3-phenylpropyl]amino]acetic Acid Sodium Salt Characterization data for this solid material is summarized in Table 18. The material is amorphous by XRPD with a broad peak at approximately 4.7°2# and additional peaks at high 2θ values, indicating that the material has some crystallinity. DSC analysis shows a broad, shallow endothermic event between 75° C. and 125° C. TG analysis shows a weight loss of approximately 0.5% between 25° C. and 150° C. Cycling DSC analysis exhibits a glass transition with an onset temperature of approximately 78° C. It appears that as the amount of amorphous mannitol present in the mixtures directly affects the glass transition temperature. The glass transition temperature decreases as the amount of amorphous mannitol increases in the solid dispersions. Since mannitol may be considered as a plasticiser, it follows that larger amounts of amorphous mannitol would result in a decrease in transition temperature. The decreasing glass transition temperatures observed with the mannitol:amorphous sodium salt mixtures are in agreement with theoretical predictions. The predicted values were obtained using the Gordon-Taylor equation (Equation 1) where the glass transition temperature of the 2:1 amorphous sodium salt was used. The 2:1 amorphous salt formed in sample and is discussed in the following paragraph.

Solution $^1$H NMR analysis shows chemical shifts that are consistent with the 2:1 amorphous sodium salt. The chemical shift of the doublet from 6.78 ppm to approximately 6.65 ppm is observed and suggests that the 2:1 salt was formed in the mixture. Chemical shifts associated with mannitol are also present.

Since the XRPD pattern indicates crystallinity, a homogeneous sample was not generated. However, the material does show an apparent glass transition temperature at approximately 78° C., which may indicate that a portion of the material formed a solid dispersion between the amorphous mannitol and amorphous 2:1 sodium salt.

5. Amorphous [[2(S)-[[4(R)-(3-hydroxyphenyl)-3(R),4-dimethyl-piperidinyl]methyl]-1-oxo-3-phenylpropyl]amino]acetic acid Sodium Salt:PVP (70:30) Mixture Attempts were made to prepare a solid dispersion with amorphous [[2(S)-[[4(R)-(3-hydroxyphenyl)-3(R),4-dimethyl-piperidinyl]methyl]-1-oxo-3-phenylpropyl]amino]acetic acid sodium salt and PVP. The amorphous material was prepared by lyophilization from 1,4-dioxane:2-butanol:water (1:1:1). Characterization data are summarized in Table 19. The material is amorphous by XRPD. DSC analysis exhibited three endothermic events at maximum temperatures 69° C., 145° C. and 170° C. TG analysis showed a weight loss of approximately 2.3% between 25° C. and 200° C. Cycling DSC was performed to determine if the material has a measurable glass transition temperature. An endothermic event at approximately 64° C. was observed during the first heating, which may be due to the release of solvent from the material. No thermal events were observed during the second heating. An endothermic event was observed at approximately 142° C. during the third heating, which may be related to removal of residual solvent. Thermal events indicative of a glass transition temperature were not observed during the analysis. This may suggest that a solid dispersion was not formed between the amorphous salt and PVP.

Moisture sorption indicates that the material gains approximately 90% weight between 5% and 95% relative humidity. Approximately 85% of the weight is loss during desorption with slight hysteresis. The material did not meet the weight requirement at some humidity steps, which indicates that the material could absorb more water if left at those humidity steps for longer durations. XRPD analysis of the post moisture sorption sample was not performed due to insufficient sample amount as a result of deliquescence.

Solution $^1$H NMR analysis shows chemical shifts that are consistent with the 2:1 amorphous sodium salt. The chemical shift of the doublet from 6.78 ppm to approximately 6.65 ppm is observed and suggests that the 2:1 salt was formed in the mixture. Chemical shifts associated with PVP are also present.

Even though the material is amorphous and forms a 2:1 alvimopan sodium salt, DSC analysis did not show a measurable glass transition temperature and suggest that a solid dispersion was not formed.

6. Amorphous [[2(S)-[[4(R)-(3-hydroxyphenyl)-3(R),4-dimethyl-piperidinyl]methyl]-1-oxo-3-phenylpropyl]amino]acetic acid Sodium Salt:PVP/VAc (70:30) Mixture Attempts were made to prepare a solid dispersion with amorphous alvimopan sodium salt and PVP/VAc. The amorphous material was prepared by lyophilization from 1,4-dioxane:t-butanol:water (1:1:1). Characterization data are summarized in Table 20. The material is amorphous by XRPD. DSC analysis exhibited two endothermic events at maximum temperatures 72° C. and 138° C. TG analysis showed a weight loss of approximately 0.9% between 25° C. and 200° C. Cycling DSC was performed to determine if the material has a measurable glass transition temperature. An endothermic event at approximately 93° C. was observed during the first heating, which may be due to the release of solvent from the material. No thermal events were observed during the second heating. An endothermic event was observed at approximately 141° C. during the third heating, which may be related to removal of residual solvent. Thermal events indicative of a glass transition temperature were not observed during the analysis. This may suggest that a solid dispersion was not formed between the amorphous salt and PVP/VAc.

Moisture sorption indicate that the material gains approximately 95% weight between 5% and 95% relative humidity. Approximately 92% of the weight is loss during desorption with slight hysteresis. The material did not meet the weight requirement at some humidity steps, which indicates that the material could absorb more water if left at those humidity steps for longer durations. XRPD analysis of the post moisture sorption sample indicated that the material was amorphous.

Solution $^1$H NMR analysis shows chemical shifts that are consistent with the 2:1 amorphous sodium salt. The chemical shift of the doublet from 6.78 ppm to approximately 6.65 ppm is observed and suggests that the 2:1 salt was formed in the mixture. Chemical shifts associated with PVP/VAc are also present.

Even though the material is amorphous and forms a 2:1 [[2(S)-[[4(R)-(3-hydroxyphenyl)-3(R),4-dimethyl-piperidinyl]methyl]-1-oxo-3-phenylpropyl]amino]acetic acid sodium salt, DSC analysis did not show a measurable glass transition temperature and suggest that a solid dispersion was not formed.

D. Relative Humidity Stability Stress Studies

Relative humidity stress studies were performed to assess the stability of amorphous alvimopan and solid dispersions. Studies were performed at ambient, 53%, and 97% relative humidity at ambient temperature. Ambient relative humidity and temperature was measured as approximately 24% and 22° C. Samples were also stressed at 75% relative humidity at 40° C. Samples were analyzed by XRPD for the presence of crystallinity.

Physical mixtures of alvimopan Form A (crystalline dihydrate) and mannitol were made in order to establish an approximate level of crystalline alvimopan needed for detection by XRPD in the prepared samples. It was determined that approximately 16% to 21% crystalline alvimopan was lowest amount detectable by XRPD (Table 21). Diffraction peaks associated with alvimopan Form A located at approximately 12.1 and 13.0° 2θ become visible between 16% and 21% alvimopan content. Therefore, the amorphous and solid dispersion samples may contain approximately 16% to 21% of undetectable crystalline alvimopan.

Crystallization of [[2(S)-[[4(R)-(3-hydroxyphenyl)-3(R),4-dimethyl-piperidinyl]methyl]-1-oxo-3-phenylpropyl] amino]acetic acid was not observed under ambient conditions after up to 60 days of exposure (Table 22). The [[2(S)-[[4(R)-(3-hydroxyphenyl)-3(R),4-dimethyl-piperidinyl]methyl]-1-oxo-3-phenylpropyl]amino]acetic acid:mannitol samples display diffraction peaks that are due to the partial crystallinity of mannitol Forms II and III. The amorphous sodium salts (1:1 and 2:1) show a broad peak at approximately 4.07 °2θ that was present in the freshly prepared samples. Crystallization of alvimopan was also not observed in any of the samples stressed at 53% relative humidity after 60 days of exposure (Table 23). Again, [[2(S)-[[4(R)-(3-hydroxyphenyl)-3(R),4-dimethyl-piperidinyl]methyl]-1-oxo-3-phenylpropyl]amino] acetic acid:mannitol samples show partial crystallinity of mannitol and the sodium salts have a broad diffraction peak at approximately 4.07°2θ.

All of the amorphous samples stressed at 97% relative humidity and ambient temperature crystallized to alvimopan Form A (crystalline dihydrate) after seven days of exposure (Table 24). The 1:1 amorphous alvimopan sodium salt likely crystallized to Form A due to breaking of the salt during the stress study. The 2:1 amorphous [[2(S)-[[4(R)-(3-hydroxyphenyl)-3(R),4-dimethyl-piperidinyl]methyl]-1-oxo-3-phenylpropyl]amino]acetic acid sodium salt deliquesced within three days of exposure.

Amorphous [[2(S)-[[4(R)-(3-hydroxyphenyl)-3(R),4-dimethyl-piperidinyl]methyl]-1-oxo-3-phenylpropyl]amino] acetic acid prepared by rotary evaporation crystallized to alvimopan Form A when stress at 75% RH and 40° C. for seven days (Table 25). Crystallization was not observed in the amorphous alvimopan sample prepared by lyophilization. The [[2(S)-[[4(R)-(3-hydroxyphenyl)-3(R),4-dimethyl-piperidinyl]methyl]-1-oxo-3-phenylpropyl]amino]acetic acid: mannitol samples exhibited crystallinity of alvimopan after 30 days of exposure. Solid dispersions prepared with HPMC, PVP, and PVP/VAC did not show any crystallinity due to alvimopan after 60 days of exposure. The amorphous sodium salts (1:1 and 2:1) deliquesced after three days of exposure. The amorphous salt solid dispersions prepared with PVP/VAc also deliquesced within 18 days of exposure at the stress conditions. Slight crystallization was observed in the amorphous sodium salt solid mixtures prepared with HPMC and PVP, which may be due to alvimopan.

Amorphous [[2(S)-[[4(R)-(3-hydroxyphenyl)-3(R),4-dimethyl-piperidinyl]methyl]-1-oxo-3-phenylpropyl]amino] acetic acid was stable under stress conditions except at 97% relative humidity. Amorphous [[2(S)-[[4(R)-(3-hydroxyphenyl)-3(R),4-dimethyl-piperidinyl]methyl]-1-oxo-3-phenylpropyl]amino]acetic acid prepared by lyophilization was stable at 75% relative humidity and 40° C., while rotary evaporation prepared amorphous [[2(S)-[[4(R)-(3-hydroxyphenyl)-3(R),4-dimethyl-piperidinyl]methyl]-1-oxo-3-phenyl propyl]amino]acetic acid showed crystallization under this same stress condition. With the exception of the [[2(S)-[[4(R)-(3-hydroxyphenyl)-3(R),4-dimethyl-piperidinyl]methyl]-1-oxo-3-phenylpropyl]amino]acetic acid:mannitol, the [[2(S)-[[4(R)-(3-hydroxyphenyl)-3(R),4-dimethyl-piperidinyl]methyl]-1-oxo-3-phenylpropyl]amino]acetic acid solid dispersions were amorphous within the detection limits of XRPD and appear to be stable to crystallization under the various stress conditions, not including 97% relative humidity, for at least 60 days. Amorphous [[2(S)-[[4(R)-(3-hydroxyphenyl)-3(R),4-dimethyl-piperidinyl]methyl]-1-oxo-3-phenylpropyl]amino]acetic acid sodium salts and solid dispersions containing the amorphous sodium salt do not appear to be stable and deliquesced when stressed above 53% relative humidity.

E. Intrinsic Dissolution Studies

Intrinsic dissolution studies were carried out for an amorphous solid dispersion of [[2(S)-[[4(R)-(3-hydroxyphenyl)-3(R),4-dimethyl-piperidinyl]methyl]-1-oxo-3-phenylpropyl] amino]acetic acid in PVP (70:30 w:w), amorphous [[2(S)-[[4(R)-(3-hydroxyphenyl)-3(R),4-dimethyl-piperidinyl] methyl]-1-oxo-3-phenylpropyl]amino]acetic acid, and crystalline [[2(S)-[[4(R)-(3-hydroxyphenyl)-3(R),4-dimethyl-piperidinyl]methyl]-1-oxo-3-phenylpropyl]amino] acetic acid dihydrate.

Methods

Preparation of Alvimopan:PVP (70:30) Amorphous Dispersion

Approximately 2.0 grams of PVP was dissolved in approximately 1000 mL of ethanol. Approximately 5.0 grams of alvimopan Form A (Lot 204007, SSCI LIMS No.

was added to the PVP solution and stirred until all of the material dissolved. The solution was filtered by vacuum filtration through a 0.2 μm nylon filter. The solution was rotary evaporated at ambient temperature. The solids were collected and dried at approximately 100° C. under vacuum for one day. The solid material was analyzed by XRPD for form identification.

Intrinsic Dissolution Experiments

Intrinsic dissolution experiments were conducted in a VanKel VK7010 dissolution apparatus equipped with a VK750A heater/circulator. An intrinsic dissolution apparatus (Woods apparatus) and hydraulic press were used to press samples of approximately 200 mg at approximately 1000 psi for 1 minute, giving a sample surface of 0.50 cm². Experiments were conducted in media of pH=1.2 HCl solution and pH =4.5 phosphate solution. 900 mL of medium was used for each experiment and the medium was maintained at approximately 37° C. The apparatus was rotated at 75 rpm. The Cary 50 UV/Vis spectrophotometer was utilized to sample automatically throughout the duration of the experiments.

Samples were analyzed with a Cary 50 UV-VIS double-beam spectrophotometer, and were analyzed in 1.000-cm quartz cuvettes at a wavelength of 271 nm. The detector was zeroed with a cuvette filled with dissolution medium prior to sample analysis. Wavelength calibration was performed using holmium oxide. The photometric accuracy was verified by measuring the intensity of the light at the detector when filters of known optical density were placed in the path of the beam. The results are shown in Table 32.

TABLE 32

Summary of Intrinsic Dissolution Studies

| Sample Description | XRPD Result | Intrinsic Dissolution Rate, mg/min/cm² (SD), pH 1.2 HCl |
|---|---|---|
| crystalline alvimopan | Form A | 0.148 (0.025) |
| amorphous preparation | amorphous | 0.217 (0.017) |
| ([[2(S)-[[4(R)-(3-hydroxyphenyl)-3(R),4-dimethyl-piperidinyl]methyl]-1-oxo-3-phenylpropyl] amino]acetic acid:PVP (70:30, w:w)) | amorphous | 1.48 (0.149) |

Intrinsic dissolution experiments were performed on alvimopan samples. The data indicate that the amorphous solid dispersion of [[2(S)-[[4(R)-(3-hydroxyphenyl)-3(R),4-dimethyl-piperidinyl]methyl]-1-oxo-3-phenylpropyl]amino] acetic acid:PVP (70:30, w:w) appears to have better dissolution behavior than the other alvimopan samples in pH 1.2 HCl solution.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A solid dispersion, which is at least a two-phase solid system of which one phase consists of finely divided solid particles distributed throughout a bulk solid substance, comprising:
   at least one pharmaceutically-acceptable excipient selected from the group consisting of hydroxypropyl methylcellulose (HPMC), polyvinylpyrrolidone homopolymer (PVP), polyvinylpyrrolidone copolymer, and mixtures thereof; and
   the compound of formula II:

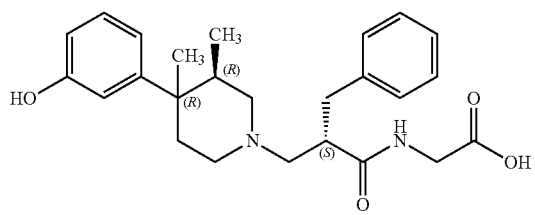

wherein said compound is in a solid amorphous form; and wherein said amorphous form is stable.

2. A solid dispersion according to claim 1, wherein said pharmaceutically-acceptable excipient is a polyvinylpyrrolidone copolymer.

3. A solid dispersion according to claim 2, wherein said polyvinylpyrrolidone copolymer is poly(vinylpyrrolidone/vinyl acetate) (PVP/VAc).

4. A solid dispersion according to claim 1, wherein said compound of formula II is a solid dispersion in a matrix formed by said pharmaceutically-acceptable excipient.

5. A solid dispersion according to claim 1, wherein the weight ratio of said compound of formula II to said pharmaceutically-acceptable excipient is about 5:95 to about 75:25.

6. A solid dispersion according to claim 5, wherein the weight ratio of said compound of formula II to said pharmaceutically-acceptable excipient is at least about 10:90.

7. A solid dispersion according to claim 6, wherein the weight ratio of said compound of formula II to said pharmaceutically-acceptable excipient is at least about 15:85.

8. A solid dispersion according to claim 7, wherein the weight ratio of said compound of formula II to said pharmaceutically-acceptable excipient is at least about 20:80.

9. A solid dispersion according to claim 8, wherein the weight ratio of said compound of formula II to said pharmaceutically-acceptable excipient is at least about 25:75.

10. A solid dispersion according to claim 9, wherein the weight ratio of said compound of formula II to said pharmaceutically-acceptable excipient is at least about 30:70.

11. A solid dispersion according to claim 1, further comprising at least one opioid.

12. A solid dispersion according to claim 11, wherein said opioid is selected from the group consisting of alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, and tramadol.

13. A dosage form, comprising:
   a solid dispersion according to claim 1.

14. A dosage form according to claim 13, wherein said dosage form is a tablet, capsule, or lozenge.

15. A method of preventing or treating a side effect associated with an opioid in a patient, comprising the step of:
   administering to said patient an effective amount of the solid dispersion of claim 1.

16. A method according to claim 15, wherein said side effect is ileus, opioid bowel dysfunction, constipation, nausea, vomiting, or a combination thereof.

17. A method according to claim 16, wherein said side effect is postoperative ileus, postoperative nausea, or postoperative vomiting.

18. A method of treating pain in a patient, comprising the step of:
   administering to said patient in need thereof an effective amount of the solid dispersion of claim 1.

19. A method according to claim 18, further comprising:

administering to said patient in need thereof an effective amount of at least one opioid.

20. A method of treating ileus in a patient, comprising the step of:

administering to said patient in need thereof an effective amount of the solid dispersion of claim 1.

21. A method of treating opioid bowel dysfunction in a patient, comprising the step of:

administering to said patient in need thereof an effective amount of the solid dispersion of claim 1.

22. A solid dispersion according to claim 1, wherein said pharmaceutically-acceptable excipient is hydroxypropyl methylcellulose.

* * * * *